United States Patent
Krivoruchko et al.

(10) Patent No.: US 12,398,409 B2
(45) Date of Patent: *Aug. 26, 2025

(54) YEAST CELLS GENETICALLY MODIFIED FOR DOWNREGULATION OF PYRUVATE DECARBOXYLASE ACTIVITY AND FBP-SENSITIVE PYRUVATE KINASE

(71) Applicant: Melt&Marble AB, Gothenburg (SE)

(72) Inventors: Anastasia Krivoruchko, Gothenburg (SE); Jens Nielsen, Hellerup (DK); Florian David, Gothenburg (SE); Tao Yu, Shenzhen (CN)

(73) Assignee: Melt&Marble AB, Gothenburg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/330,457

(22) Filed: Jun. 7, 2023

(65) Prior Publication Data
US 2023/0313242 A1 Oct. 5, 2023

Related U.S. Application Data

(63) Continuation of application No. 16/830,854, filed on Mar. 26, 2020, now Pat. No. 11,692,209.

(60) Provisional application No. 62/824,398, filed on Mar. 27, 2019.

(51) Int. Cl.
*C12P 7/6409* (2022.01)
*C12N 1/16* (2006.01)
*C12N 9/00* (2006.01)

(52) U.S. Cl.
CPC .............. *C12P 7/6409* (2013.01); *C12N 1/16* (2013.01); *C12N 9/93* (2013.01); *C12Y 604/01001* (2013.01); *C12Y 604/01002* (2013.01)

(58) Field of Classification Search
None
See application file for complete search history.

(56) References Cited

U.S. PATENT DOCUMENTS

| | | |
|---|---|---|
| 10,533,198 B2 | 1/2020 | Nielsen et al. |
| 11,162,119 B2 | 11/2021 | Nielsen et al. |
| 11,692,209 B2 * | 7/2023 | Krivoruchko ............ C12N 9/93 435/134 |
| 2004/0214306 A1 * | 10/2004 | Bloom .................. C12N 1/205 435/252.33 |
| 2011/0125118 A1 * | 5/2011 | Lynch .................... C12N 15/52 435/243 |
| 2011/0223641 A1 * | 9/2011 | Stephanopoulos .... C12N 9/001 435/243 |
| 2016/0215308 A1 * | 7/2016 | Runguphan .......... C12N 9/1029 |
| 2016/0237441 A1 * | 8/2016 | Nielsen .................. C12N 15/52 |

FOREIGN PATENT DOCUMENTS

| | | |
|---|---|---|
| CN | 107164254 A | 9/2017 |
| WO | 2014/016328 A1 | 1/2014 |
| WO | 2016/159869 A1 | 10/2016 |
| WO | 2018/192572 A1 | 10/2018 |

OTHER PUBLICATIONS

Pfleger, Brian F. et al., Metabolic engineering strategies for microbial synthesis of oleochemicals, Metabolic Engineering, vol. 29, pp. 1-50 (2015).
Yu, Tao et al., Reprogramming Yeast Metabolism from Alcoholic Fermentation to Lipogenesis, Cell, vol. 174, pp. 1549-1558 (Sep. 6, 2018).
Singh, Raushan Kumar et al., Protein Engineering Approaches in the Post-Genomic Era, Current Protein and Peptide Science, vol. 18, pp. 1-11 (2017).
Jones, Krstala et al., De novo biosynthetic pathways: rational design of microbial chemical factories, Current Opinion In Biotechnology, vol. 19, pp. 468-474 (2008).
Chica Roberto A et al., Semi-rational approaches to engineering enzyme activity: combining the benefits of directed evolution and rational design, Current Opinion in Biotechnology, vol. 16, pp. 378-384 (2005).
Kizer, Lance et al., Application of Functional Genomics to Pathway Optimization for Increased Isoprenoid Production, Applied and Environmental Microbiology, vol. 74, No. 10, pp. 3229-3241 (2008).
Accession Q00955, Apr. 1, 1993.
Accession P11154. Jul. 1, 1989.
Accession Q5BAJ4 Apr. 26, 2005.
Accession P38225 Oct. 1, 1994.

* cited by examiner

*Primary Examiner* — Christian L Fronda
(74) *Attorney, Agent, or Firm* — Porter Wright Morris & Arthur LLP

(57) ABSTRACT

A fungal cell capable of producing high levels of fatty acids and fatty acid-derived products comprises at least one modification to the endogenous fatty acid metabolism.

13 Claims, 17 Drawing Sheets

Specification includes a Sequence Listing.

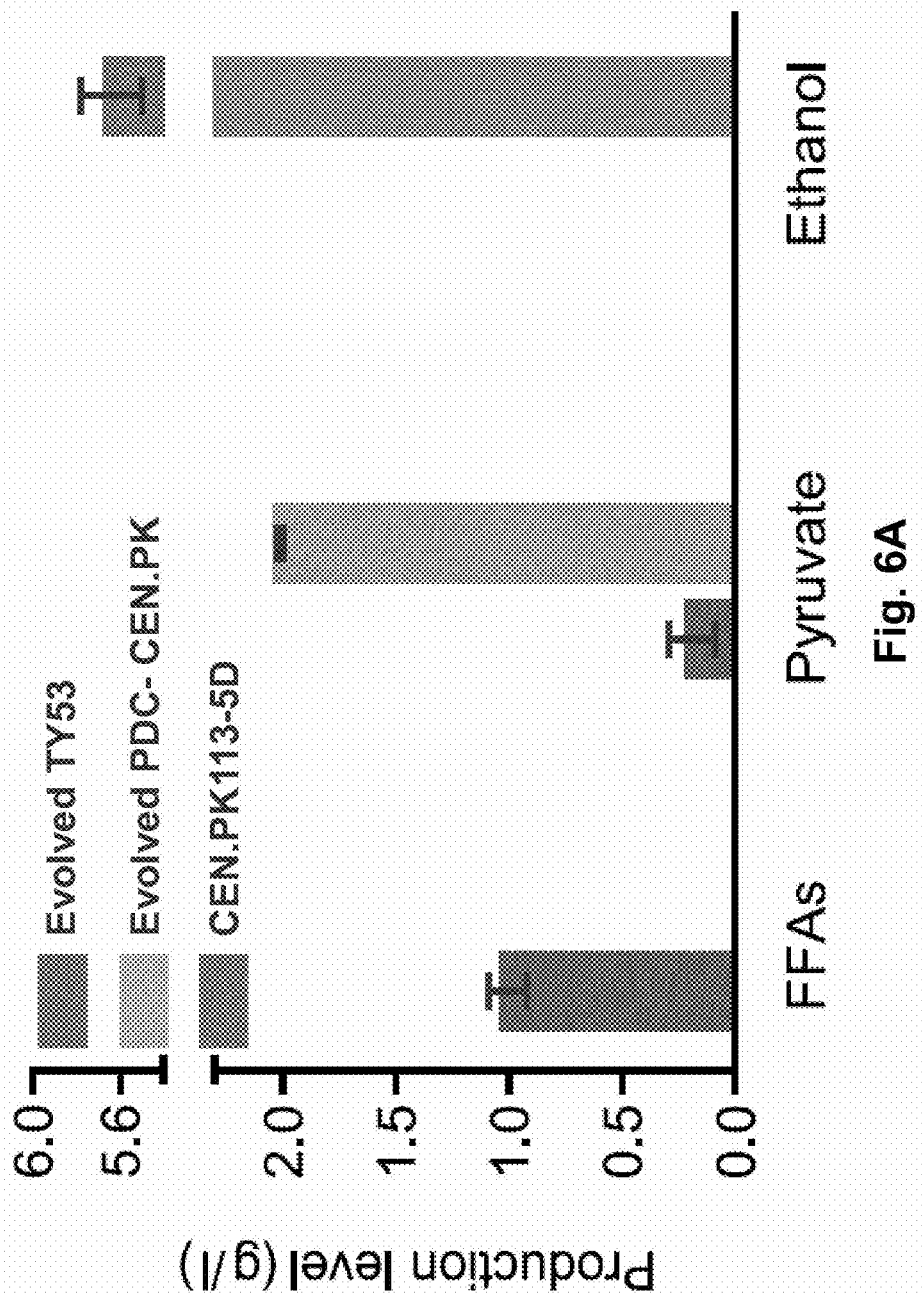

YEAST CELLS GENETICALLY MODIFIED FOR DOWNREGULATION OF PYRUVATE DECARBOXYLASE ACTIVITY AND FBP-SENSITIVE PYRUVATE KINASE

CROSS-REFERENCE TO RELATED APPLICATION

This application is based on and claims priority under 35 USC 119 to U.S. Provisional application No. 62/824,398, filed on Mar. 27, 2019, in the U.S. Patent and Trademark Office, the entire contents thereof are incorporated herein by reference. This application also claims prior under 35 USC 120 to U.S. application Ser. No. 16/830,854 filed Mar. 26, 2020, the entire contents thereof are incorporated herein by reference.

The Sequence Listing submitted herewith entitled June-7-2023-Sequence-Listing.XML, created Jun. 6, 2023 and having a size of 63,499 bytes, is incorporated herein by reference.

TECHNICAL FIELD

The present invention relates generally to the development of genetically engineered microorganisms. More specifically, the invention relates to fungal cells able to produce fatty acids and/or fatty acid-derived products in an economic fashion.

BACKGROUND

Fatty acids are carboxylic acids with a long aliphatic chain that is either saturated or unsaturated. Fatty acids and their derived products, e.g., fatty alcohols, fatty acid esters, etc., have numerous commercial applications including as surfactants, lubricants, plasticizers, solvents, emulsifiers, emollients, thickeners, flavors, pesticides, cosmetics, nutraceuticals and fuels. Current technologies for producing fatty acids and fatty acid-derived products are typically via extraction from plant or animal sources, such as coconut, palm, palm kernel, tallow and lard. However, due to concerns regarding the sustainability of these sources, as well as increasing demands for specialty fatty acids that cannot be easily derived from natural sources, alternative production methods are needed. For example, research efforts have focused on production of fatty acids via microbial fermentation (Pfleger et al., 2015). In addition, recent advances in genetic and metabolic engineering have allowed for precise manipulation of the microbial metabolism to produce tailor-made products. Other advantages of these production platforms include environmental friendliness, scalability, geographical independence, and cost effectiveness. Microbial fatty acid biosynthesis has attracted much attention for production of oleochemicals and biofuels. Engineering of central metabolism and fatty acid biosynthesis enabled fatty acid overproduction in *Escherichia coli, Saccharomyces cerevisiae*, and *Yarrowia lipolytica*. However, the production titer and yield need to be further enhanced to enable industrial production using new strategies.

There is therefore still a need for techniques for the production of fatty acids and/or fatty acid-derived products in yeast cells in an efficient way.

SUMMARY

It is a general objective to provide improved production of fatty acids and/or fatty acid-derived products in fungal cells.

The present invention provides a genetically engineered fungal cell, preferably a yeast cell, which comprises genetic modifications that allow increased production of fatty acids and/or fatty acid-derived products. The fungal cell is genetically modified for overexpression of an acetyl-CoA carboxylase and a pyruvate carboxylase.

The yeast *Saccharomyces cerevisiae* is a very important cell factory as it is already widely used for production of biofuels, chemicals and pharmaceuticals, and there is therefore much interest in developing platform strains of this yeast that can be used for production of a whole range of different products. It is, however, a problem that such a platform cell factory for efficient production of fatty acids and fatty acid-derived products is not as efficient as needed for good industrial application. This invention involves a multiple gene modification approach of the yeast to generate a stable and scalable platform for production fatty acids and fatty acid-derived products.

The present invention relates to a fungal cell and methods as defined in the independent claims. Further embodiments of the invention are defined in the dependent claims.

BRIEF DESCRIPTION OF THE DRAWINGS

The embodiments, together with further objects and advantages thereof, may best be understood by making reference to the following description taken together with the accompanying drawings, in which:

(FIG. 3A) Schematic illustration of metabolic connections between glycolysis, TCA cycle and PPP. Pushing carbon flux into PPP for improving FFA production by tuning PGI1 and IDH2 expression. Fine tuning of PGI1 (FIG. 3B) and IDH2 (FIG. 3C) improved FFA production up to 60%. The strains were cultivated in shake flasks for 80 h at 200 rpm, 30° C. with glucose feed beads corresponding to 30 g/L glucose. All data represent the mean±s.d. of biological triplicates.

FIGS. 6A-6C: Rewiring yeast from alcoholic fermentation to fatty acid production. (FIG. 6A) The production profile of wild-type *S. cerevisiae* (CEN.PK113-5D), an evolved wild-type pyruvate dexarboxylase (PDC)-negative strain and the evolved TY53 strain. Strains were cultured in shake flasks at 200 rpm, 30° C. on 30 g/L glucose. All data represent the mean±SD of biological triplicates. (FIG. 6B) Free fatty acid production in fed-batch cultures of the evolved PDC-negative yeast with glucose limitation and nitrogen restriction. Circle indicates overall free fatty acid production at the end of fermentation. (FIG. 6C) Time-course for glucose consumption and dry cell weight accumulation during fed-batch fermentation of evolved pyruvate decarboxylase-negative yeast.

DETAILED DESCRIPTION

Figure 1:
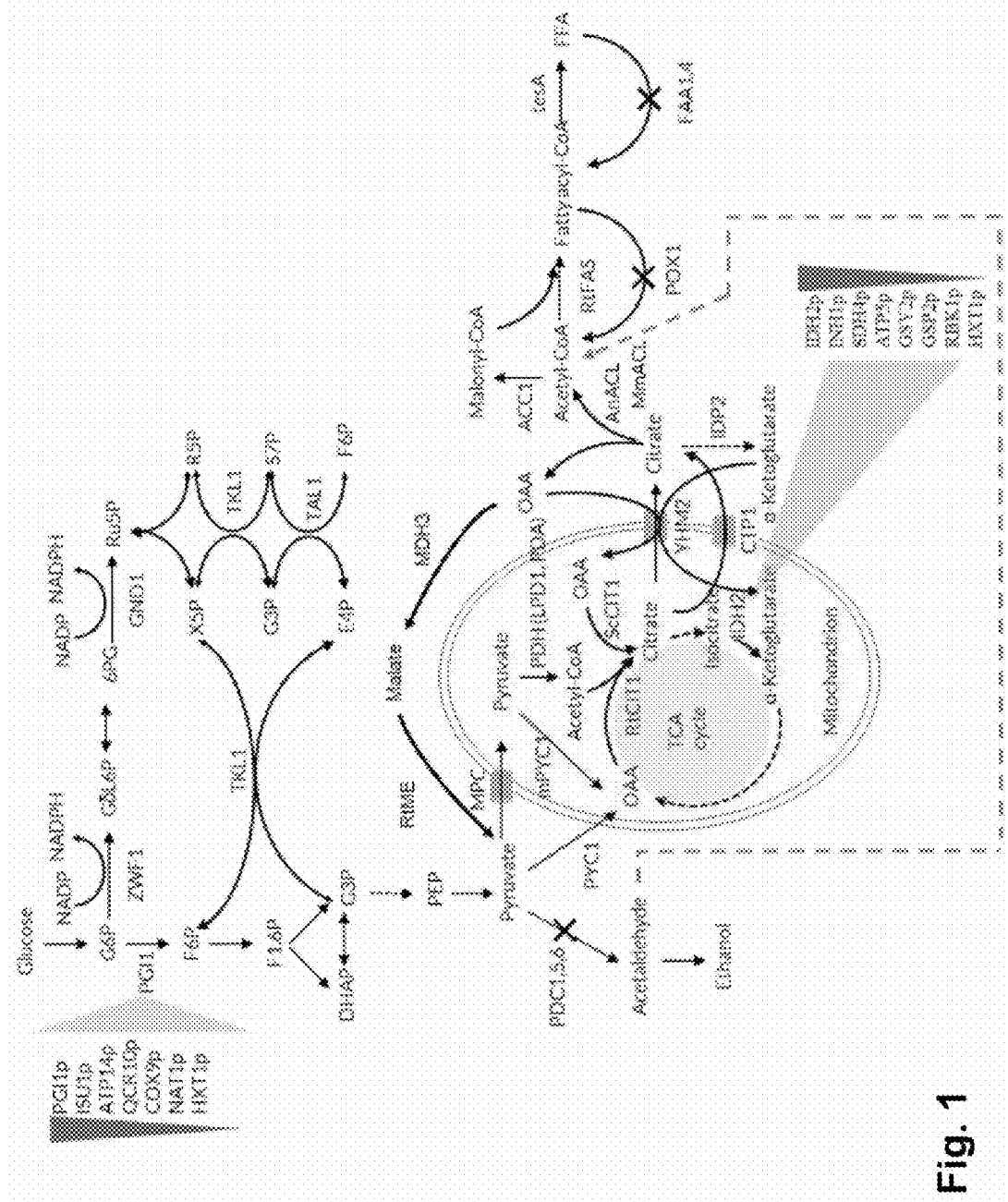
FIG. 1: Schematic illustration of various modifications for increased fatty acid production. Engineering targets include tesA, the truncated *E. coli* thioesterase; MmACL, ATP:citrate lyase from *Mus musculus*; RtME, cytosolic NADP+-dependent malic enzyme from *Rhodosporidium toruloides*; MDH3, endogenous malate dehydrogenase with removed peroxisomal signal; mPYC1, mitochondria-targeted pyruvate carboxylase; CTP1, citrate transporter and RtFAS, fatty acid synthase from *Rhodosporidium toruloides*. For free fatty acid (FFA) production, fatty acyl-CoA synthetase encoding genes FAA1 and FAA4, and fatty acyl-CoA oxidase encoding gene POX1 were disrupted. Additional engineering targets include MPCox, overexpressed endogenous mitochondrial pyruvate carrier (MPC1 and MPC3); RtCIT1, citrate synthase from *Rhodosporidium toruloides*; ScCIT1, citrate synthase from *Saccharomyces cerevisiae*; AnACL, ATP:citrate lyase from *Aspergillus nidulans*; PDA1, pyruvate dehydrogenase alpha; E3 (LPD1), dihydrolipoamide dehydrogenase; PGI1, phosphoglucose isomerase; ZWF1, cytoplasmic glucose-6-phosphate dehydrogenase; GND1, the isoform 1 of phosphogluconate dehydrogenase; TKL1, transketolase 1; TAL1, transaldolase 1 and IDH2, subunit 2 of mitochondrial NAD(+)-dependent isocitrate dehydrogenase. Native PYC1 (pyruvate carboxylase 1), YHM2 (citrate and oxoglutarate carrier protein 2), IDP2 (cytosolic NADP-specific isocitrate dehydrogenase 2) and ACC1 (acetyl-CoA carboxylase 1) were overexpressed. For the abolishment of ethanol production, pyruvate carboxylase encoding genes PDC1, PDC5 and PDC6 were disrupted. To fine tune gene expression, the promoter of PGI1 was replaced by the promoters of ISU1 (IScU homolog 1), ATP14 (ATP synthase 14), QCR10 (ubiQuinol-cytochrome C oxidoReductase 10), COX9 (Cytochrome c Oxidase 9), NAT1 (N-terminal AcetylTransferase 1), and HXT1 (Low-affinity glucose transporter 1), and the promoter of IDH2 was replaced by the promoters of INH1 (Protein that inhibits ATP hydrolysis by the F1F0-ATP synthase 1), SDH4 (Membrane anchor subunit of succinate dehydrogenase 4), ATP5 (ATP synthase 5), GSY2 (Glycogen synthase 2), GSP2 (GTP binding protein 2), RBK1 (RiBoKinase 1), and HXT1.

The present invention now will be described hereinafter with reference to the accompanying drawings and examples, in which embodiments of the invention are shown. This description is not intended to be a detailed catalogue of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined herein, scientific and technical terms used herein will have the meanings that are commonly understood by those of ordinary skill in the art.

Generally, nomenclatures used in connection with techniques of biochemistry, enzymology, molecular and cellular biology, microbiology, genetics and protein and nucleic acid chemistry and hybridization, described herein, are those well-known and commonly used in the art.

Conventional methods and techniques mentioned herein are explained in more detail, for example, in Molecular Cloning, a laboratory manual [second edition] Sambrook et al. Cold Spring Harbor Laboratory, 1989, for example in Sections 1.21 "Extraction And Purification Of Plasmid DNA", 1.53 "Strategies For Cloning In Plasmid Vectors", 1.85 "Identification Of Bacterial Colonies That Contain Recombinant Plasmids", 6 "Gel Electrophoresis Of DNA", 14 "In vitro Amplification Of DNA By The Polymerase Chain Reaction", and 17 "Expression Of Cloned Genes In *Escherichia coli*" thereof.

Enzyme Commission (EC) numbers (also called "classes" herein), referred to throughout this specification, are according to the Nomenclature Committee of the International Union of Biochemistry and Molecular Biology (NC-IUBMB) in its resource "Enzyme Nomenclature" (1992, including Supplements 6-17) available, for example, as "Enzyme nomenclature 1992: recommendations of the Nomenclature Committee of the International Union of Biochemistry and Molecular Biology on the nomenclature and classification of enzymes", Webb, E. C. (1992), San Diego: Published for the International Union of Biochemistry and Molecular Biology by Academic Press (ISBN 0-12-227164-5). This is a numerical classification scheme based on the chemical reactions catalyzed by each enzyme class.

The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

As used herein, the transitional phrase "consisting" essentially of means that the scope of a claim is to be interpreted to encompass the specified materials or steps recited in the claim and those that do not materially affect the basic and novel characteristic(s) of the claimed invention. Thus, the term "consisting essentially of when used in a claim of this invention is not intended to be interpreted to be equivalent to "comprising."

To facilitate understanding of the invention, a number of terms are defined below.

As used herein, the term "fatty acid" refers to a carboxylic acid with a long aliphatic chain, composed of 4 to 40 carbons, which is either saturated or unsaturated. An unsaturated fatty acid contains at least one double or triple bond within its aliphatic chain, which can occur at any position. To define the position of the double bond, the delta-x (delta(x) or Δ-x) nomenclature is used herein. In this nomenclature, each double bond is indicated by "delta(x)", where the double bond is located on the $x^{th}$ carbon-carbon bond, counting from the carboxylic acid end. A fatty acid can be either straight-chained or have branches, i.e., with one or more alkyl groups, such as methyl groups, on the carbon chain. Furthermore, a fatty acid can have additional modifications, such as hydroxylation, i.e., a hydroxy fatty acid, epoxidation, i.e., an epoxy fatty acid and/or comprise multiple, i.e., at least two, carboxylic groups, such as a dicarboxylic fatty acid. Within the cell, fatty acids can occur as free fatty acids (FFAs), fatty acyl-CoAs, fatty acyl-ACPs, fatty acids within triacylglycerols (TAGs), fatty acids within steryl esters, or fatty acids within phospholipids.

As used herein, the term "fatty acid-derived product" refers to any molecule that is created by further modification of a fatty acid in the fungal cell. Examples of fatty acid derived products include, but are not limited to fatty alcohols, fatty aldehydes, fatty acid esters, hydrocarbons, triacylglycerides, lactones and phospholipids.

The term "fatty acyl-CoA" refers to a fatty acid that is bound to a coenzyme A (CoA).

The term "fatty acyl-ACP" refers to a fatty acid that is found to an acyl carrier protein (ACP).

Also, as used herein, the terms "nucleotide sequence" "nucleic acid," "nucleic acid molecule," "oligonucleotide" and "polynucleotide" refer to RNA or DNA, including cDNA, a DNA fragment or portion, genomic DNA, synthetic DNA, plasmid DNA, mRNA, and anti-sense RNA, any of which can be single stranded or double stranded, linear or branched, or a hybrid thereof. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

As used herein the term "recombinant" when used means that a particular nucleic acid (DNA or RNA) is the product of various combinations of cloning, restriction, and/or ligation steps resulting in a construct having a structural coding or non-coding sequence distinguishable from endogenous nucleic acids found in natural systems.

As used herein, the term "gene" refers to a nucleic acid molecule capable of being used to produce mRNA, anti-sense RNA, miRNA, anti-microRNA antisense oligodeoxyribonucleotide (AMO) and the like. Genes may or may not be capable of being used to produce a functional protein or gene product. Genes can include both coding and non-coding regions, e.g., introns, regulatory elements, promoters, enhancers, termination sequences and/or 5' and 3' untranslated regions. A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

A "disrupted gene" as defined herein involves any mutation or modification to a gene resulting in a partial or fully non-functional gene and gene product. Such a mutation or modification includes, but is not limited to, a missense mutation, a nonsense mutation, a deletion, a substitution, an insertion, addition of a targeting sequence and the like. Furthermore, a disruption of a gene can be achieved also, or alternatively, by mutation or modification of control elements controlling the transcription of the gene, such as mutation or modification in a promoter, terminator and/or enhancement elements. In such a case, such a mutation or modification results in partially or fully loss of transcription of the gene, i.e., a lower or reduced transcription as compared to native and non-modified control elements. As a result a reduced, if any, amount of the gene product will be available following transcription and translation. Furthermore, disruption of a gene could also entail adding or removing a localization signal from the gene, resulting in decreased presence of the gene product in its native subcellular compartment.

The objective of gene disruption is to reduce the available amount of the gene product, including fully preventing any production of the gene product, or to express a gene product that lacks or having lower enzymatic activity as compared to the native or wild type gene product.

As used herein the term "deletion" or "knock-out" refers to a gene that is inoperative or knocked out.

The term "lowered activity" or "attenuated activity" when related to an enzyme refers to a decrease in the activity of the enzyme in its native compartment compared to a control or wild-type state. Manipulations that result in attenuated activity of an enzyme include, but are not limited to, a missense mutation, a nonsense mutation, a deletion, a substitution, an insertion, addition of a targeting sequence, removal of a targeting sequence, or the like. Furthermore, attenuation of enzyme activity can be achieved also, or alternatively, by mutation or modification of control elements controlling the transcription of the gene encoding the enzyme, such as mutation or modification in a promoter, terminator and/or enhancement elements. A cell that contains modifications that result in attenuated enzyme activity will have a lower activity of the enzyme compared to a cell that does not contain such modifications. Attenuated activity of an enzyme may be achieved by encoding a nonfunctional gene product, e.g., a polypeptide having essentially no activity, e.g., less than about 10% or even 5% as compared to the activity of the wild type polypeptide.

A "codon optimized" version of a gene refers to an exogenous gene introduced into a cell and where the codons of the gene have been optimized with regard to the particular cell. Generally, not all tRNAs are expressed equally or at the same level across species. Codon optimization of a gene sequence thereby involves changing codons to match the most prevalent tRNAs, i.e., to change a codon recognized by a low prevalent tRNA with a synonymous codon recognized by a tRNA that is comparatively more prevalent in the given cell. This way the mRNA from the codon optimized gene will be more efficiently translated. The codon and the synonymous codon preferably encode the same amino acid.

As used herein, the term "allele" refers to a variant form of a given gene. This can include a mutated form of a gene where one or more of the amino acids encoded by the gene have been removed or substituted by a different amino acid.

As used herein, the terms "peptide", "polypeptide", and "protein" are used interchangeably to indicate to a polymer of amino acid residues. The terms "peptide", "polypeptide" and "protein" also includes modifications including, but not limited to, lipid attachment, glycosylation, glycosylation, sulfation, hydroxylation, γ-carboxylation of L-glutamic acid residues and ADP-ribosylation.

As used herein, the term "enzyme" is defined as a protein which catalyzes a chemical or a biochemical reaction in a cell. Usually, according to the present invention, the nucleotide sequence encoding an enzyme is operably linked to a nucleotide sequence (promoter) that causes sufficient expression of the corresponding gene in the cell to confer to the cell the ability to produce fatty acids.

As used herein, the term "open reading frame (ORF)" refers to a region of RNA or DNA encoding polypeptide, a peptide, or protein.

As used herein, the term "genome" encompasses both the plasmids and chromosomes in a host cell. For instance, encoding nucleic acids of the present disclosure which are introduced into host cells can be portion of the genome whether they are chromosomally integrated or plasmids-localized.

As used herein, the term "promoter" refers to a nucleic acid sequence which has functions to control the transcription of one or more genes, which is located upstream with respect to the direction of transcription of the transcription initiation site of the gene. Suitable promoters in this context include both constitutive and inducible natural promoters as well as engineered promoters, which are well known to the person skilled in the art. In this application, promoters are designed with a "p" in front of the gene name (e.g., "pTEF1" is the promoter of the gene TEF1).

Suitable promoters for use in eukaryotic host cells, such as yeast cells, may be the promoters of PDC, GPD1, TEF1, PGK1 and TDH. Other suitable promoters include the promoters of GAL1, GAL2, GAL10, GAL7, CUP1, HIS3, CYC1, ADH1, PGL, GAPDH, ADC1, URA3, TRP1, LEU2, TPI, AOX1 and ENO1.

As used herein, the term "promoter activity" refers to the ability of a promoter to facilitate expression of the gene lying immediately downstream of said promoter. Typical indicators of a promoter's activity include the timing of expression and level of expression of its downstream gene relative to other genes. A promoter with high or strong activity will lead to high levels of transcription of the gene lying immediately downstream of said promoter, subsequently resulting in high mRNA (and subsequently protein) levels of said gene. A promoter with weak or low activity will lead to low levels of transcription of the gene lying immediately downstream of said promoter, subsequently resulting in low mRNA levels of said gene. Promoter activity can usually be assessed by measuring the mRNA expression of its downstream gene, or by placing a reporter gene immediately downstream of a promoter and observing e.g., fluorescence or colour formation upon respective protein formation. Factors influencing the strength and activity of a promoter can include transcription factor binding (dependent on binding sites in the promoter), efficiency of recruiting RNA polymerases, environmental conditions, etc.

As used herein, the term "terminator" refers to a "transcription termination signal" if not otherwise noted. Terminators are sequences that hinder or stop transcription of a polymerase.

As used herein, "recombinant eukaryotic cells" according to the present disclose is defined as cells which contain additional copies or copy of an endogenous nucleic acid sequence or are transformed or genetically modified with polypeptide or a nucleotide sequence that does not naturally occur in the eukaryotic cells. The wildtype eukaryotic cells are defined as the parental cells of the recombinant eukaryotic cells, as used herein.

As used herein, "recombinant prokaryotic cells" according to the present disclose is defined as cells which contain additional copies or copy of an endogenous nucleic acid sequence or are transformed or genetically modified with polypeptide or a nucleotide sequence that does not naturally occur in the prokaryotic cells. The wildtype prokaryotic cells are defined as the parental cells of the recombinant prokaryotic cells, as used herein.

As used herein, the terms "increase," "increases," "increased," "increasing," "enhance," "enhanced," "enhancing," and "enhancement" (and grammatical variations thereof) indicate an elevation of at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more, or any range therein, as compared to a control.

As used herein, the terms "reduce," "reduces," "reduced," "reduction," "diminish," "suppress," and "decrease" and similar terms mean a decrease of at least about, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more, or any range therein, as compared to a control.

A reduced expression of a gene as used herein involves a genetic modification that reduces the transcription of the gene, reduces the translation of the mRNA transcribed from the gene and/or reduces post-translational processing of the protein translated from the mRNA. Such genetic modification includes insertion(s), deletion(s), replacement s) or mutation(s) applied to the control sequence, such as a promoter and enhancer, of the gene. For instance, the promoter of the gene could be replaced by a less active or inducible promoter to thereby result in a reduced transcription of the gene. Also a knock-out of the promoter would result in reduced, typically zero, expression of the gene.

As used herein, the term "portion" or "fragment" of a nucleotide sequence of the invention will be understood to mean a nucleotide sequence of reduced length relative to a reference nucleic acid or nucleotide sequence and comprising, consisting essentially of and/or consisting of a nucleotide sequence of contiguous nucleotides identical or almost identical, e.g., 80%, 81%, 82%, 83%, 84%, 85%, 86%, 87%, 88%, 89%, 90%, 91%, 92%, 93%, 94%, 95%, 96%, 98%, 99% identical, to the reference nucleic acid or nucleotide sequence. Such a nucleic acid fragment or portion according to the invention may be, where appropriate, included in a larger polynucleotide of which it is a constituent.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity, i.e., sequence similarity or identity. Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity, e.g., at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, and/or 100%, to said nucleotide sequence.

The term "overexpress," "overexpresses", "overexpression" or "upregulation" as used herein refers to higher levels of activity of a gene, e.g., transcription of the gene; higher levels of translation of mRNA into protein; and/or higher levels of production of a gene product, e.g., polypeptide, than would be in the cell in its native or control, e.g., not transformed with the particular heterologous or recombinant polypeptides being overexpressed, state. A typical example of an overexpressed gene is a gene under transcription control of another promoter as compared to the native promoter of the gene. Also, or alternatively, other changes in the control elements of a gene, such as enhancers, could be used to overexpress the particular gene. Furthermore, modifications that affect, i.e., increase, the translation of the mRNA transcribed from the gene could, alternatively or in addition, be used to achieve an overexpressed gene as used herein. These terms can also refer to an increase in the number of copies of a gene and/or an increase in the amount of mRNA and/or gene product in the cell. Overexpression can also be achieved by introducing one or more exogenous versions of the gene from another species. Overexpression can result in levels that are 25%, 50%, 100%, 200%, 500%, 1000%, 2000% or higher in the cell, or any range therein, as compared to control levels.

The term "downregulation" or "down-regulation" as used herein refers to lower levels of activity of a gene, e.g., transcription of the gene; lower levels of translation of mRNA into protein; and/or lower levels of production of a gene product, e.g., polypeptide, than would be in the cell in its native or control, e.g., not transformed with the particular heterologous or recombinant polypeptides being overexpressed, state. A typical example of downregulated gene is a gene under transcription control of another promoter with lower activity as compared to the native promoter of the gene. Also, or alternatively, other changes in the control elements of a gene, such as silencer elements, could be used to downregulate the particular gene. Furthermore, modifications that affect, i.e., decrease, the translation of the mRNA transcribed from the gene could, alternatively or in addition, be used to achieve a downregulated gene as used herein. These terms can also refer to a decrease in the amount of mRNA and/or gene product in the cell. In addition, this term can be used to refer to a gene that is disrupted or completely deleted. Downregulation can result in levels that are 10%, 20%, 50% or 100% lower in the cell, or any range therein, as compared to control levels.

As used herein, the terms "exogenous" or "heterologous" when used with respect to a nucleic acid (RNA or DNA), protein or gene refer to a nucleic acid, protein or gene which occurs non-naturally as part of the cell, organism, genome, RNA or DNA sequence into which it is introduced, including non-naturally occurring multiple copies of a naturally occurring nucleotide sequence. Such an exogenous gene could be a gene from another species or strain, a modified, mutated or evolved version of a gene naturally occurring in the host cell or a chimeric version of a gene naturally occurring in the host cell or fusion genes. In these former cases, the modification, mutation or evolution causes a change in the nucleotide sequence of the gene to thereby obtain a modified, mutated or evolved gene with another nucleotide sequence as compared to the gene naturally occurring in the host cell. Evolved gene refers to genes encoding evolved genes and obtained by genetic modification, such as mutation or exposure to an evolutionary pressure, to derive a new gene with a different nucleotide sequence as compared to the wild type or native gene. A chimeric gene is formed through the combination of portions of one or more coding sequences to produce a new gene. These modifications are distinct from a fusion gene, which merges whole gene sequences into a single reading frame and often retain their original functions.

An "endogenous", "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism. A "homologous" nucleic acid sequence is a nucleotide sequence naturally associated with a host cell into which it is introduced.

As used herein, the term "modified", when it is used with respect to an organism, refers to a host organism that has been modified to increase production of fatty acids and/or derived products, as compared with an otherwise identical host organism that has not been so modified. In principle, such "modification" in accordance with the present disclosure may comprise any physiological, genetic, chemical, or other modification that appropriately alters production of fatty acids in a host organism as compared with such production in an otherwise identical organism which is not subject to the said modification. In most of the embodiments, however, the modification will comprise a genetic modification. In certain embodiments, as described herein, the modification comprises introducing genes into a host cell. In some embodiments, a modification comprises at least one physiological, chemical, genetic, or other modification; in other embodiments, a modification comprises more than one chemical, genetic, physiological, or other modification. In certain aspects where more than one modification is made use of, such modifications can include any combinations of physiological, genetic, chemical, or other modification (e.g., one or more genetic, chemical and/or physiological modification(s)). Genetic modifications which boost the activity of a polypeptide include, but are not limited to: introducing one or more copies of a gene encoding the polypeptide (which may distinguish from any gene already present in the host cell encoding a polypeptide having the same activity); altering a gene present in the cell to increase transcription or translation of the gene (e.g., altering, adding additional sequence to, replacement of one or more nucleotides, deleting sequence from, or swapping for example, regulatory, a promoter or other sequence); and altering the sequence (e.g., non-coding or coding) of a gene encoding the polypeptide to boost activity (e.g., by increasing enzyme activity, decrease feedback inhibition, targeting a specific subcellular location, boost mRNA stability, boost protein stability). Genetic modifications that reduce activity of a polypeptide include, but are not limited to: deleting a portion or all of a gene encoding the polypeptide; inserting a nucleic acid sequence which disrupts a gene encoding the polypeptide; changing a gene present in the cell to reduce transcription or translation of the gene or stability of the mRNA or polypeptide encoded by the gene (for example, by adding additional sequence to, altering, deleting sequence from, replacement of one or more nucleotides, or swapping for example, replacement of one or more nucleotides, a promoter, regulatory or other sequence).

The term "overproducing" is used herein in reference to the production of fatty acids or derived products in a host cell and indicates that the host cell is producing more fatty acids or derived products by virtue of the introduction of nucleic acid sequences which encode different polypeptides involved in the host cell's metabolic pathways or as a result of other modifications as compared with the unmodified host cell or wild-type cell.

As used herein, the term "flux", "metabolic flux" or "carbon flux" refers to the rate of turnover of molecules through a given reaction or a set of reactions. Flux in a metabolic pathway is regulated by the enzymes involved in the pathway. Pathways or reactions characterized by a state of increased flux compared to a control have an increased rate of generation of products from given substrates. Pathways or reactions characterized by a state of decreased flux compared to a control have a decreased rate of generation of products from given substrates. Flux towards products of interest can be increased by removing or decreasing competitive reactions or by increasing the activities of enzymes involved in generation of said products.

As used herein, the term "acetyl-CoA derived products" refers to molecules for which acetyl-Coenzyme A (acetyl-CoA) is a precursor. Acetyl-CoA serves as a key precursor metabolite for the production of important cellular constituents such as fatty acids, sterols, and amino acids as well as it is used for acetylation of proteins. Besides these important functions it is also precursor metabolite for many other biomolecules, such as polyketides, isoprenoids, 3-hydroxypropionic acid, 1-butanol and polyhydroxyalkanoids, which encompass many industrially relevant chemicals.

As used herein the term "vector" is defined as a linear or circular DNA molecule comprising a polynucleotide encoding a polypeptide of the invention, and which is operably linked to additional nucleotides that ensure its expression.

"Introducing" in the context of a yeast cell means contacting a nucleic acid molecule with the cell in such a manner that the nucleic acid molecule gains access to the interior of the cell. Accordingly, polynucleotides and/or nucleic acid molecules can be introduced yeast cells in a single transformation event, in separate transformation events. Thus, the term "transformation" as used herein refers to the introduction of a heterologous nucleic acid into a cell. Transformation of a yeast cell can be stable or transient.

"Transient transformation" in the context of a polynucleotide means that a polynucleotide is introduced into the cell and does not integrate into the genome of the cell.

By "stably introducing" or "stably introduced" in the context of a polynucleotide introduced into a cell, it is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. Stable transformation as used herein can also refer to a nucleic acid molecule that is maintained extrachromasomally, for example, as a minichromosome.

Embodiments of the present invention also encompass variants of the polypeptides as defined herein. As used herein, a "variant" means a polypeptide in which the amino acid sequence differs from the base sequence from which it is derived in that one or more amino acids within the sequence are substituted for other amino acids. For example, a variant of SEQ ID NO:1 may have an amino acid sequence at least about 50% identical to SEQ ID NO:1, for example, at least about 55%, 60%, 65%, 70%, 75%, 80%, 85%, 90%, 91%, 92%, 93%, 94%, 95%, 96%, 97%, 98%, 99% or about 100% identical. The variants and/or fragments are functional variants/fragments in that the variant sequence has similar or identical functional enzyme activity characteristics to the enzyme having the non-variant amino acid sequence specified herein (and this is the meaning of the term "functional variant" as used throughout this specification).

A "functional variant" or "functional fragment" of any of the presented amino acid sequences, therefore, is any amino acid sequence which remains within the same enzyme category (i.e., has the same EC number) as the non-variant sequences. Methods of determining whether an enzyme falls within a particular category are well known to the skilled person, who can determine the enzyme category without use of inventive skill. Suitable methods may, for example, be obtained from the International Union of Biochemistry and Molecular Biology.

Amino acid substitutions may be regarded as "conservative" where an amino acid is replaced with a different amino acid with broadly similar properties. Non-conservative substitutions are where amino acids are replaced with amino acids of a different type.

By "conservative substitution" is meant the substitution of an amino acid by another amino acid of the same class, in which the classes are defined as follows:
Class Amino Acid Examples
  Nonpolar: A, V, L, I, P, M, F, W
  Uncharged polar: G, S, T, C, Y, N, Q
  Acidic: D, E
  Basic: K, R, H.

As it is well known to those skilled in the art, altering the primary structure of a polypeptide by a conservative substitution may not significantly alter the activity of that polypeptide because the side-chain of the amino acid which is inserted into the sequence may be able to form similar bonds and contacts as the side chain of the amino acid which has been substituted out. This is so even when the substitution is in a region which is critical in determining the polypeptide's conformation.

In embodiments of the present invention, non-conservative substitutions are possible provided that these do not interrupt the enzyme activities of the polypeptides, as defined elsewhere herein. The substituted versions of the enzymes must retain characteristics such that they remain in the same enzyme class as the non-substituted enzyme, as determined using the NC-IUBMB nomenclature discussed above.

Broadly speaking, fewer non-conservative substitutions than conservative substitutions will be possible without altering the biological activity of the polypeptides. Determination of the effect of any substitution (and, indeed, of any amino acid deletion or insertion) is wholly within the routine capabilities of the skilled person, who can readily determine whether a variant polypeptide retains the enzyme activity according to aspects of the invention. For example, when determining whether a variant of the polypeptide falls within the scope of the invention (i.e., is a "functional variant or fragment" as defined above), the skilled person will determine whether the variant or fragment retains the substrate converting enzyme activity as defined with reference to the NC-IUBMB nomenclature mentioned elsewhere herein. All such variants are within the scope of the invention.

Using the standard genetic code, further nucleic acid sequences encoding the polypeptides may readily be conceived and manufactured by the skilled person, in addition to those disclosed herein. The nucleic acid sequence may be DNA or RNA, and where it is a DNA molecule, it may for example comprise a cDNA or genomic DNA. The nucleic acid may be contained within an expression vector, as described elsewhere herein.

Embodiments of the invention, therefore, encompass variant nucleic acid sequences encoding the polypeptides contemplated by embodiments of the invention. The term "variant" in relation to a nucleic acid sequence means any substitution of, variation of, modification of, replacement of, deletion of, or addition of one or more nucleotide(s) from or to a polynucleotide sequence, providing the resultant polypeptide sequence encoded by the polynucleotide exhibits at least the same or similar enzymatic properties as the polypeptide encoded by the basic sequence. The term includes allelic variants and also includes a polynucleotide (a "probe sequence") which substantially hybridizes to the polynucleotide sequence of embodiments of the present invention. Such hybridization may occur at or between low and high stringency conditions. In general terms, low stringency conditions can be defined as hybridization in which the washing step takes place in a 0.330-0.825 M NaCl buffer solution at a temperature of about 40-48° C. below the calculated or actual melting temperature (Tm) of the probe sequence (for example, about ambient laboratory temperature to about 55° C.), while high stringency conditions involve a wash in a 0.0165-0.0330 M NaCl buffer solution at a temperature of about 5-10° C. below the calculated or actual Tm of the probe sequence (for example, about 65° C.). The buffer solution may, for example, be SSC buffer (0.15M NaCl and 0.015M tri-sodium citrate), with the low stringency wash taking place in 3×SSC buffer and the high stringency wash taking place in 0.1×SSC buffer. Steps involved in hybridization of nucleic acid sequences have been described for example in Molecular Cloning, a laboratory manual [second edition] Sambrook et al. Cold Spring Harbor Laboratory, 1989, for example in Section 11 "Synthetic Oligonucleotide Probes" thereof (herein incorporated by reference)

Preferably, nucleic acid sequence variants have about 55% or more of the nucleotides in common with the nucleic acid sequence of embodiments of the present invention, more preferably at least 60%, 65%, 70%, 80%, 85%, or even 90%, 95%, 98% or 99% or greater sequence identity.

Variant nucleic acids of the invention may be codon-optimized for expression in a particular host cell.

As used herein, "sequence identity" refers to sequence similarity between two nucleotide sequences or two peptide or protein sequences. The similarity is determined by sequence alignment to determine the structural and/or functional relationships between the sequences.

Sequence identity between amino acid sequences can be determined by comparing an alignment of the sequences using the Needleman-Wunsch Global Sequence Alignment Tool available from the National Center for Biotechnology Information (NCBI), Bethesda, Md., USA, for example via http://blast.ncbi.nlm.nih.gov/Blast.cgi, using default parameter settings (for protein alignment, Gap costs Existence:11 Extension:1). Sequence comparisons and percentage identities mentioned in this specification have been determined using this software.

An aspect of the embodiments relates to a fungal cell suitable for the production of fatty acids and/or fatty acid-derived products. The fungal cell is, in this aspect, genetically modified for overexpression of an acetyl-CoA carboxylase (EC 6.4.1.2) and a pyruvate carboxylase (EC 6.4.1.1).

In the following, various embodiments of the present invention will be described in more detail.

In an embodiment, the fungal cell is a fungal cell selected from a group consisting of *Saccharomyces, Kluyveromyces, Zygosaccharomyces, Candida, Hansenula, Torulopsis, Kloeckera, Pichia, Schizosaccharomyces, Trigonopsis, Brettanomyces, Debaromyces, Nadsonia, Lipomyces, Cryptococcus, Aureobasidium, Trichosporon, Lipomyces, Rhodotomula, Yarrowia, Rhodosporidium, Phaffia, Schwanniomyces, Aspergillus* and *Ashbya*. In a particular embodiment, the fungal cell can be *Saccharomyces cerevisiae, Pichia pastoris, Ashbya gossypii, Saccharomyces boulardii, Zygosaccharomyces bailii, Kluyveromyces lactis, Rhodosporidium toruloides* and *Yarrowia lipolytica*. *Saccharomyces cerevisiae* and *Yarrowia lipolytica* are preferred yeast species.

According to the invention, the fungal cell is engineered for increased supply of acetyl-CoA and/or malonyl-CoA, precursors for fatty acids. This is achieved by upregulation of genes coding for pyruvate carboxylase (PYC) to increase oxaloacetate supply and acetyl-CoA carboxylase (ACC) to increase pull towards malonyl-CoA. For instance, production of the enzymes PYC1 (YGL062W) and ACC1 (YNR016C) could be upregulated in the fungal cell.

In an embodiment, the fungal cell is genetically modified for overexpression of a mitochondrial pyruvate carrier to increase pyruvate import into mitochondria under high glucose. For instance, production of the proteins MPC1 (YGL080W) and/or MPC3 (YGR243W) could be upregulated in the fungal cell. These modifications could be combined with the modifications above, or be completely independent.

In an embodiment, the fungal cell is further genetically modified for overexpression of a citrate and oxoglutarate carrier protein, which is an antiporter contributing to increased NADPH in the cytosol. For instance, production of the protein YHM2 (YMR241W) could be upregulated in the fungal cell.

In an embodiment, the fungal cell is further genetically modified for overexpression of a cytosolic isocitrate dehydrogenase (IDH) (EC 1.1.1.42). For instance, production of the enzyme IDP2 (YLR174W) could be upregulated in the fungal cell.

Any or all of the above mentioned embodiments could be combined in the fungal cell.

According to the invention, the fungal cell is genetically modified for enhanced activity of acetyl-CoA carboxylase, preferably ACC1 (SEQ ID NO: 1), or a variant of SEQ ID NO: 1. This may be achieved via overexpression of ACC1 and/or via expression or overexpression of a mutant ACC1 variant with higher activity. Illustrative, but non-limiting, example of such mutant ACC1 variants include ACC1 from *Saccharomyces cerevisiae*, in which serine 659 in SEQ ID NO: 1 and/or serine 1157 in SEQ ID NO: 1 is/are replaced with alanine.

According to the invention, the fungal cell is genetically modified for enhanced activity of pyruvate carboxylase, preferably PYC1 (SEQ ID NO: 2), or a variant of SEQ ID NO: 2. This can be achieved, for example, via overexpression of PYC1.

Another aspect of the embodiments relates to a fungal cell for the production of fatty acids and/or fatty acid-derived products. The fungal cell is genetically modified for overexpression of an acetyl-CoA carboxylase, preferably ACC1, and for overexpression of a mitochondrial pyruvate carrier, preferably MPC1 and/or MPC3. In another embodiment, the fungal cell is genetically modified for overexpression of a pyruvate carboxylase, preferably PYC1, and for overexpression of a mitochondrial pyruvate carrier, preferably MPC1 and/or MPC3.

In an embodiment, the fungal cell is genetically modified for:
  Overexpression or enhanced activity of an acetyl-CoA carboxylase, preferably ACC1, and
  Overexpression or enhanced activity of a pyruvate carboxylase, preferably PYC1, and
  Overexpression or enhanced activity of a mitochondrial pyruvate carrier, preferably MPC1 and/or MPC3

In an embodiment, the fungal cell also comprises modifications focusing on increasing the synthesis of citrate as precursor for acetyl-CoA in the fungal cell. This could be achieved by overexpression of a citrate synthase (EC 2.3.3.16), such as overexpression of *S. cerevisiae* citrate synthase ScCIT1 (YNR001C) and/or overexpression of citrate synthase RtCIT1 from *Rhodosporidium toruloides* (SEQ ID NO: 3), or a variant of SEQ ID NO: 3.

In another embodiment, the fungal cell instead or in addition comprises modifications to enhance mitochondrial oxaloacetate production required for citrate synthesis by targeting the cytosolic pyruvate carboxylase into the mitochondria (mPYC1) (SEQ ID NO: 4), or a variant of SEQ ID NO: 4.

In another embodiment, the fungal cell instead or in addition comprises modifications to enhance the flux from citrate to acetyl-CoA via expression, preferably overexpression, of an ATP-citrate-lyase (EC 2.3.3.8), preferably a heterologous ATP-citrate lyase, such as AnACL from *Aspergillus nidulans* (SEQ ID NO: 5), or a variant of SEQ ID NO: 5.

In another embodiment, the fungal cell instead or in addition comprises modifications to enhance export of citrate from the mitochondria to the cytosol by downregulation of the gene coding for the mitochondrial NAD+-dependent isocitrate dehydrogenase IDH2 (YOR136W, EC 1.1.1.41) (SEQ ID NO: 14). This modification could be combined with any of the modifications above or be completely independent. In the latter case, the invention relates to a fungal cell, preferably a fungal cell for the production of fatty acids and/or fatty acid-derived products, wherein the fungal cell is genetically modified for downregulation of the gene coding for the mitochondrial NAD+-dependent isocitrate dehydrogenase IDH2 (YOR136W, EC 1.1.1.41) (SEQ ID NO: 14).

The downregulation of the endogenous mitochondrial NAD+-dependent isocitrate dehydrogenase can be achieved by having a native promoter of the mitochondrial NAD+-dependent isocitrate dehydrogenase replaced by a comparatively weaker promoter. For instance, the native promoter can be replaced by a weaker promoter selected from the group consisting of pINH1, pSDH4, pATP5, pGSY2, pGSP2, and pRBK1.

Any of the above described modifications can be combined.

A further aspect of the embodiments relates to a fungal cell for the production of fatty acids and/or fatty acid-derived products. The fungal cell is genetically modified for overproduction of an acetyl-CoA carboxylase, preferably ACC1, and for overexpression of a citrate synthase, preferably CIT1 from *Rhodosporidium toruloides*. In another embodiment, the fungal cell is genetically modified for overexpression of a citrate synthase, preferably CIT1 from *Rhodosporidium toruloides*, and for overexpression of a pyruvate carboxylase, preferably PYC1.

In an embodiment, the fungal cell is genetically modified for:
- Overexpression or enhanced activity of an acetyl-CoA carboxylase, preferably ACC1, and
- Overexpression or enhanced activity of a pyruvate carboxylase, preferably PYC1, and
- Overexpression or enhanced activity of a citrate synthase, preferably CIT1 from *Rhodosporidium toruloides*.

In an embodiment, the fungal cell is genetically modified for overexpression of the citrate synthase, preferably CIT1 from *Rhodosporidium toruloides*, and for overexpression of a citrate and oxoglutarate carrier protein, preferably YHM2.

In an embodiment, the fungal cell is instead or in addition genetically modified for overexpression of the citrate synthase, preferably CIT1 from *Rhodosporidium toruloides*, and for overexpression of a cytosolic isocitrate dehydrogenase, preferably IDP2.

In an embodiment, the fungal cell is modified for overexpression of the citrate synthase, preferably CIT1 from *Rhodosporidium toruloides*, and for overexpression of an ATP-citrate-lyase, preferably AnACL from *Aspergillus nidulans*.

In an embodiment, the fungal cell with any of the above modifications is further genetically modified for downregulation of an endogenous mitochondrial NAD+-dependent isocitrate dehydrogenase, for example IDH2. Downregulation of the mitochondrial NAD+-dependent isocitrate dehydrogenase can be accomplished by replacement of the native promoter of the mitochondrial NAD+-dependent isocitrate dehydrogenase with a weaker promoter, preferably taken from the group consisting of pINH1, pSDH4, pATP5, pGSY2, pGSP2, pRBK1.

In a preferred embodiment, a fungal cell is modified for increased NADPH supply for elongation and reduction reactions. This could be achieved by downregulation of a gene encoding for an endogenous phosphoglucose isomerase (PGI) (YBR196C, EC 5.3.1.9), thereby directing the metabolic flux into the pentose phosphate pathway (PPP) for increased generation of NADPH. Thus, in an embodiment, the fungal cell with any of the above modifications is further genetically modified for downregulation of the endogenous phosphoglucose isomerase, for example PGI1. Downregulation of the endogenous phosphoglucose isomerase may be accomplished by replacement of the native promoter controlling the expression of the phosphoglucose isomerase by a weaker promoter, preferably selected from the group consisting of pISU1, pATP14, pQCR10, pCOX9, pNAT1 and pHXT1. This modification could be combined with any of the modifications above or be completely independent. In the latter case, the invention relates to a fungal cell, preferably a fungal cell for the production of fatty acids and/or fatty acid-derived products, wherein the fungal cell is genetically modified for downregulation of the endogenous phosphoglucose isomerase, for example PGI1 (YBR196C, EC 5.3.1.9).

In another preferred embodiment, NADPH supply in the fungal cell is further increased by overexpressing genes coding for a glucose-6-phosphate dehydrogenase (ZWF1; YNL241C, EC 1.1.1.49) catalyzing the irreversible and rate limiting first step of PPP and is responsible for the main NADPH regeneration from NADP+; GND1 (YHR183W, EC 1.1.1.44) encoding the major phosphogluconate dehydrogenase that catalyzes the second oxidative reduction of NADP+ to NADPH; TKL1 (YPR074C, EC 2.2.1.1) and TAL1 (YLR354C, EC 2.2.1.2) encoding a transketolase and a transaldolase of the non-oxidative PPP. Other ways to increase NADPH could include expression of a gene coding for a non-phosphorylating NADP+-dependent glyceraldehydes-3-phosphate dehydrogenase (GAPN; preferably from *Streptococcus mutans*), or a phosphoketolase pathway e.g., from *Aspergillus nidulans* (heterologous expression of xpkA and ack). In an embodiment, the fungal cell is a *Saccharomyces cerevisiae* cell genetically modified for overexpression of an endogenous GDH2 (YDL215C, EC 1.4.1.2) gene encoding a NAD-dependent glutamate dehydrogenase. These modifications could be combined with any of the modifications above, or be completely independent.

In a preferred embodiment, the fungal cell is genetically modified for overexpression of an acetyl-CoA carboxylase, preferably ACC1, and overexpression of a pyruvate carboxylase, preferably PYC1, and any of the following:
- Overexpression of a mitochondrial pyruvate carrier, preferably MPC1 and/or MPC3, and/or
- Overexpression of a citrate synthase, preferably CIT1 from *Rhodosporidium toruloides*, and/or
- Overexpression of a citrate and oxoglutarate carrier protein, preferably YHM2, and/or
- Overexpression of a cytosolic isocitrate dehydrogenase, preferably IDP2, and/or
- Overexpression of an ATP-citrate lyase, preferably from *Aspergillus nidulans*, and/or
- Downregulation of the endogenous mitochondrial NAD+-dependent isocitrate dehydrogenase, preferably IDH2, and/or
- Downregulation of the endogenous phosphoglucose isomerase, preferably PGI1.

In an embodiment, the fungal cell is a *S. cerevisiae* with the following modifications:
- Upregulation of genes coding for PYC1 (YGL062W, EC 6.4.1.1) (increasing oxaloacetate supply), ACC1 (YNR016C; EC 6.4.1.2) (increasing pull towards malonyl-CoA), IDP2 (YLR174W, EC 1.1.1.42), YHM2 (YMR241W) (antiporter contributing to increased NADPH in cytosol), MPC1 (YGL080W) and MPC3 (YGR243W) (increase pyruvate import into mitochondria under high glucose), and
- Downregulation of endogenous genes encoding for a phosphoglucose isomerase PGI1 (YBR196C, EC 5.3.1.9), thereby directing the metabolic flux into the pentose phosphate pathway for increased generation of NADPH;
- Increasing NADPH supply in the fungal cell by overexpressing genes coding for a glucose-6-phosphate dehydrogenase (ZWF1, YNL241C, EC 1.1.1.49), the major phosphogluconate dehydrogenase GND1 coded by GND1 (YHR183W, EC 1.1.1.44), a transketolase and a transaldolase coded by TKL1 (YPR074C, EC 2.2.1.1) and TAL1 (YLR354C, EC 2.2.1.2); and
- Enhanced export of citrate from the mitochondria to the cytosol by downregulation of the gene coding for the mitochondrial NAD+-dependent isocitrate dehydrogenases IDH2 (YOR136W, EC 1.1.1.41) and IDP1 (YDL066W, EC 1.1.1.42) (SEQ ID NO: 6), or a variant of SEQ ID NO: 6.

In an embodiment, the fatty acid production in the fungal cell could be increased by redirecting the flux from cell growth to fatty acid production by limiting cell growth through downregulation of essential genes by replacing a native promoter of the essential gene by a carbon-source dependent promoter. For example, the $P_{HX}T1$ promoter could be introduced to control the expression of the essential genes ERG9 (YHR190W, EC 2.5.1.21) and/or LEU2 (YCL018W, EC 1.1.1.85) in, for instance, *S. cerevisiae* or *Y. lipolytica* to limit cell growth at low glucose concentrations.

These modifications could be combined with any of the modifications above, or be completely independent.

In an embodiment, the fatty acid production in the fungal cell factory could be increased by redirecting the flux from cell growth to fatty acid production by limiting cell growth through limiting supply of an essential nutrient. For example the supply of nitrogen is limiting cell growth in *S. cerevisiae* and leads to increase of fatty acid production.

In an embodiment, any of the modifications above may be combined with genetic modifications in the fungal cell to abolish ethanol formation. This includes downregulating pyruvate decarboxylase activity in the fungal cell by deletion of one or more genes coding for pyruvate decarboxylases catalyzing the decarboxylation of pyruvate to acetaldehyde. For example, deletion of the genes PDC1, PDC5, and/or PDC6 (YLR044C, YLR134W, YGR087C, SEQ ID NO: 7-9), or variants of SEQ ID NI: 7-9, in the yeast *S. cerevisiae* leads to abolishment of ethanol formation (Zhang et al., 2015.) and all or some of these could be deleted or downregulated to decrease or completely abolish ethanol production.

In another embodiment, any of the modifications above are combined with genetic modifications to restore growth on glucose of fungal cells abolished for ethanol formation. This includes inserting specific mutations in the gene MTH1$^{81D}$ (YDR277C) or truncated versions of the MTH1 gene (SEQ ID NO: 10), coding for a version with higher activity.

In another embodiment any of the modifications above are combined with adaptive laboratory evolution (ALE) to restore growth on glucose of fungal cells abolished for ethanol formation. This includes e.g., exposing the engineered yeast cell stepwise to lower concentrations of ethanol with at the same time increasing the concentration of glucose in the cultivation medium.

In an embodiment, the fungal cell is modified to abolish ethanol formation as well as lower the activity of a fructose-1,6-bisphosphate (FBP)-sensitive pyruvate kinase, for example PYK1 (SEQ ID NO: 11), also known as CDC19, or a variant of SEQ ID NO: 11. In another embodiment, the fungal cell is alternatively, or in addition, modified for increased activity of a FBP-insensitive pyruvate kinase, such as PYK2 (SEQ ID NO: 12), or a variant of SEQ ID NO: 12. Downregulation of PYK1 activity can be accomplished by deletion, promoter replacement, or mutation, for example in the R68, K196, or R91 residues. Increased activity of PYK2 can be accomplished by overexpression, for example via promoter replacement or introduction of additional copies. For example, in a preferred embodiment a fungal cell with deletions in the genes PDC1 and PDC5 is further modified for downregulation of PYK1 and overexpression of PYK2. These modifications can be combined with the above modifications for fatty acid production, or be completely independent.

In an embodiment, the fungal cell is genetically modified for:
  Overexpression or enhanced activity of an acetyl-CoA carboxylase, preferably by overexpression of ACC1, and
  Overexpression or enhanced activity of a pyruvate carboxylase, preferably by overexpression of PYC1, and
  Downregulation or decreased activity of a pyruvate decarboxylase, preferably by deletion of PDC1, PDC5 and/or PDC6, and
  Downregulation or decreased activity of a FBP-sensitive pyruvate kinase, preferably by deletion or downregulation of PYK1.

In an embodiment, the fungal cell is genetically modified for:
  Overexpression or enhanced activity of an acetyl-CoA carboxylase, preferably by overexpression of ACC1, and
  Overexpression or enhanced activity of a pyruvate carboxylase, preferably by overexpression of PYC1, and
  Downregulation or decreased activity of a pyruvate decarboxylase, preferably by deletion of PDC1, PDC5 and/or PDC6, and
  Overexpression or enhanced activity of a FBP-insensitive pyruvate kinase, preferably by overexpression of PYK2.

In an embodiment, the fungal cell is a *Saccharomyces cerevisiae* yeast cell genetically modified for overproduction of an acetyl-CoA-derived product. The yeast cell is further modified for decreased ethanol production via deletion or downregulation of PDC1, PDC5 and/or PDC6. In a further embodiment the yeast cell is genetically modified for deletion or downregulation of PYK1. In a further embodiment the aforementioned yeast cell is further modified for overexpression of PYK2. These modifications can be combined with the above modifications for fatty acid production, or be completely independent.

In a preferred embodiment, the fungal cell is genetically modified for:
  Overexpression or enhanced activity of an acetyl-CoA carboxylase, preferably by overexpression of ACC1, and
  Overexpression or enhanced activity of a pyruvate carboxylase, preferably by overexpression of PYC1, and
  Downregulation or decreased activity of a pyruvate decarboxylase, preferably by deletion of PDC1, PDC5 and/or PDC6, and
  Downregulation or decreased activity of a FBP-sensitive pyruvate kinase, preferably by deletion or downregulation of PYK1, and
  Overexpression or enhanced activity of a FBP-insensitive pyruvate kinase, preferably by overexpression of PYK2.

In some embodiments, the fungal cell has increased production capacities for free fatty acids incorporating genetic modifications, including deletion of the genes coding for a fatty aldehyde dehydrogenase (HFD1, YMR110C. EC 1.2.1.3), a fatty-acyl coenzyme A oxidase (POX1, YGL205W, EC 1.3.3.6) and/or fatty acyl-CoA synthetases FAA1 (YOR317W, EC 6.2.1.3) and FAA4 (YMR246W, EC 6.2.1.3). In addition, or alternatively, the fungal cell is genetically modified for overexpression of heterologous genes including *Mus musculus* ATP-citrate-lyase (MmACL, EC 2.3.3.8), *R. toruloides* malic enzymes (RtME, EC 1.1.1.40), a truncated version of *E. coli* thioesterase (tesA, EC 3.1.2.2) and overexpression of *R. toruloides* FAS encoding genes (RtFAS1 and RtFAS2). In an embodiment, to further increase free fatty acid production endogenous genes coding for mitochondrial citrate transporter (CTP1, YBR291C) and malate dehydrogenase (MDH3, YDL078C, EC 1.1.1.37) may be overexpressed. These modifications could be combined with any of the modifications above, or be completely independent.

In an embodiment, the fungal cell is genetically modified for:
  Deletion in POX1, FAA1 and FAA4, and
  Overexpression of a thioesterase, preferably tesA from *Escherichia coli*, and
  Overexpression of endogenous ACC1 and PYC1, and
  Deletion of PDC1, PDC5 or PDC6, and Deletion of PYK1, and
Overexpression of PYK2.

In another embodiment, the fungal cell is *Saccharomyces cerevisiae* and is genetically modified for:
Deletion of HFD1, POX1, FAA1 and FAA4, and
Overexpression of an ATP-citrate lyase, preferably from *Mus Musculus* or *Aspergillus nidulans*, and
Overexpression of a cytosolic NADP+-dependent malic enzyme, preferably from *Rhodosporidium toruloides*, and
Overexpression of endogenous CTP1 and MDH3, and
Overexpression of a thioesterase, preferably tesA from *Escherichia coli*, and
Overexpression of FAS1 and/or FAS2, preferably from *Rhodosporidium toruloides*, and
Overexpression of endogenous ACC1 and PYC1, and
Overexpression of CIT1, preferably from *Rhodosporidium toruloides*, and
Overexpression of endogenous PDA1, IDP2 and YHM2, and
Downregulation of PGI1, and
Overexpression of endogenous GND1, TKL1, TAL1, and ZWF1, and
Downregulation of IDH2, and
Deletion of PDC1, PDC5 and PDC6, and
Deletion of PYK1, and
Overexpression of PYK2.

In an embodiment, increased production of fatty acids and/or fatty acid-derived products is, instead or in addition, achieved through overexpression of one or more endogenous yeast genes selected from the group consisting of M-Phase Phosphoprotein 6 homolog (MPP6) (SEQ ID NO: 27), or a variant of SEQ ID NO:27; Acyl Carrier Protein (ACP1) (SEQ ID NO: 28), or a variant of SEQ ID NO: 28; EthanolaminePhosphoTransferase (EPT1) (SEQ ID NO: 29), or a variant of SEQ ID NO: 29; Long chain fatty acyl-CoA synthetase (FAA1) (SEQ ID NO: 30), or a variant of SEQ ID NO: 30; Mitochondrial phosphatidylglycerophosphatase (GEP4) (SEQ ID NO: 31), or a variant of SEQ ID NO: 31; ADP-ribosylation factor-binding protein GGA2 (GGA2) (SEQ ID NO: 13), or a variant of SEQ ID NO: 13; NADP-dependent isocitrate dehydrogenase (IDP3) (SEQ ID NO: 32), or a variant of SEQ ID NO: 32; Phosphatidylinositol 4,5-bisphosphate 5-phosphatase (INP54) (SEQ ID NO: 33), or a variant of SEQ ID NO: 33; Lipid phosphate phosphatase (LPP1) (SEQ ID NO: 34), or a variant of SEQ ID NO: 34; Mitochondrial NADH-cytochrome b5 reductase (MCR1) (SEQ ID NO: 35), or a variant of SEQ ID NO: 35; sphingolipid homeostasis protein ORM1 (ORM1) (SEQ ID NO: 36), or a variant of SEQ ID NO: 36; Restriction of telomere capping protein 3 (RTC3) (SEQ ID NO: 37), or a variant of SEQ ID NO: 37; SP07 (SEQ ID NO: 38), or a variant of SEQ ID NO: 38; TriGlyceride Lipase (TGL1) (SEQ ID NO: 39), or a variant of SEQ ID NO: 39; YFT2 (SEQ ID NO: 40), or a variant of SEQ ID NO: 40. These modifications can be combined with any of the above modifications or be completely independent. In a preferred embodiment, the fungal cell overexpresses GGA2 (SEQ ID NO: 13), or a variant of SEQ ID NO: 13. This modification can be combined with any of the above modifications or be completely independent.

In an embodiment, the fungal cell overexpresses GGA2 and INP54. This modification can be combined with any of the above modifications or be completely independent.

In an embodiment, the fungal cell overexpresses GGA2 and IDP3. This modification can be combined with any of the above modifications or be completely independent.

In an embodiment, the fungal cell overexpresses GGA2 and TGL1. This modification can be combined with any of the above modifications or be completely independent.

In an embodiment, the fungal cell overexpresses INP54 and IDP3. This modification can be combined with any of the above modifications or be completely independent.

In an embodiment, the fungal cell overexpresses GGA2, INP54 and IDP3. This modification can be combined with any of the above modifications or be completely independent.

In an embodiment, the fungal cell overexpresses GGA2, INP54, IDP3 and TGL1. This modification can be combined with any of the above modifications or be completely independent.

In an embodiment, the fungal cell overexpresses GGA2 and is used for production of a fatty acid composed of 16 carbons, including, but not limited to, palmitic acid or palmitoleic acid. This modification can be combined with any of the above modifications or be completely independent.

In an embodiment, the fungal cell overexpresses EPT1 and is used for production of a fatty acid composed of 16 carbons, including, but not limited to, palmitic acid or palmitoleic acid. This modification can be combined with any of the above modifications or be completely independent.

In an embodiment, the fungal cell overexpresses IDP3 and is used for production of a fatty acid composed of 16 carbons, including, but not limited to, palmitic acid or palmitoleic acid. This modification can be combined with any of the above modifications or be completely independent.

In an embodiment, the fungal cell overexpresses TGL1 and is used for production of a fatty acid composed of 16 carbons, including, but not limited to, palmitic acid or palmitoleic acid. This modification can be combined with any of the above modifications or be completely independent.

In an embodiment, the fungal cell overexpresses RTC3 and is used for production of oleic acid. This modification can be combined with any of the above modifications or be completely independent.

In an embodiment, the fungal cell for production of fatty acids is genetically modified for:
Overexpression or enhanced activity of an acetyl-CoA carboxylase and/or a pyruvate carboxylase, and
Overexpression or enhanced activity of GGA2

In an embodiment, the fungal cell for production of fatty acids is genetically modified for:
Overexpression or enhanced activity of an acetyl-CoA carboxylase and/or a pyruvate carboxylase, and
Overexpression or enhanced activity of a citrate synthase and/or a mitochondrial pyruvate carrier, and
Overexpression or enhanced activity of GGA2.

In an embodiment, the fungal cell is genetically modified for:
Reduction in ethanol formation by downregulation or deletion of genes selected from the group consisting of PDC1, PDC5 and PDC6, and
Downregulation of PYK1 and/or overexpression of PYK2, and
Overexpression of GGA2.

In some embodiments, the fungal cell is further modified for reduced expression or knockout of pathways competing for fatty acids. This can include genes selected from a group consisting of acyl-CoA: sterol acyltransferase (ARE1, YCR048W, EC 2.3.1.26; ARE2, YNR019W, EC 2.3.1.26), diacylglycerol acyltransferase (DGA1, YOR245C, EC 2.3.1.20), lecithin cholesterol acyl transferase (LRO1, YNR008W, EC 2.3.1.158), fatty-acyl coenzyme A oxidase (POX1, YGL205W, EC 1.3.3.6).

In some embodiments, the fungal cell is further modified for reduced expression or knockout of genes involved in fatty acid activation in order to increase accumulation of free fatty acids. This can include, for example, fatty acyl-coA synthetases, such as the genes FAA1 (YOR317W, EC 6.2.1.3), FAA2 (YER015W, EC 6.2.1.3), FAA3 (YIL009W, EC 6.2.1.3), FAA4 (YMR246W, EC 6.2.1.3) and FAT1 YBR041W, EC 6.2.1.3).

In some embodiments, endogenous fatty acid genes are de-regulated. For example, the elongation genes, ELO1, ELO2 and/or ELO3, can be de-regulated if shorter-chain (less than 16 carbons) or longer-chain (more than 18 carbons) fatty acids are required so that a) their expression and/or activity is lower during the production phase than during the growth phase and (b) the expression and/or activity during the production phase is lower than the endogenous expression and/or activity during this phase as compared to a non-de-regulated control. Such de-regulation could be achieved via promoter replacement or via other means as described above.

In some embodiments, the fungal cell is modified for increased conversion of fatty acyl CoAs to free fatty acids with the overexpression of a thioesterase. This can be done via overexpression of endogenous thioesterases, or heterologous thioesterases, such as mammalian ACOT genes, for instance, *Homo sapiens* ACOT2 (GenBank: P 006812.3), *Homo sapiens* ACOT9 (Genbank: P_001028755.2), *Rattus norvegicus* ACOT2 (GenBank: P_620262.2) or *Rattus norvegicus* ACOT 1 (Genbank: P_112605.1).

In some embodiments, any of the modifications above can be combined with expression of acyl-CoA oxidases (EC 1.3.3.6) or acyl-CoA dehydrogenases (EC 1.3.8.7) to facilitate chain shortening of the fatty acid.

In an embodiment, the fungal cell is genetically modified for overexpression of at least one enzyme involved in fatty acid synthesis in the fungal cell and selected from the group consisting of a fatty acid synthase, such as FAS1 and/or FAS2; an acyl-CoA-binding protein, such as ACB1; a mitochondrial citrate transporter, such as CTP1; a malate dehydrogenase, such as MDH3; cytosolic isocitrate dehydrogenase, such as IDP2; a citrate and oxoglutarate carrier protein, such as YHM2; a mitochondrial pyruvate carrier, such as MPC1 and/or MPC3; a citrate synthase, such as CIT1; a glucose-6-phosphate dehydrogenase, such as ZWF1; a transketolase, such as TKL1; a transaldolase, such as TAL1; and a glutamate dehydrogenase, such as GDH2.

In an embodiment, the fungal cell is genetically modified for attenuated activity or downregulation of at least one enzyme involved in fatty acid biosynthesis in the fungal cell and selected from the group consisting of a fatty-acyl-CoA synthetase, such as FAA1, FAA2, FAA3, FAA4 and/or FAT1; a fatty aldehyde dehydrogenase, such as HFD1; a fatty-acyl-CoA oxidase, such as POX1; a mitochondrial isocitrate dehydrogenase, such as IDH2 and/or IDP1; a phosphoglucose isomerase, such as PGI1; an acyl-CoA-sterol acyltransferase, such as ARE1 and/or ARE2; a diacylglycerol acyltransferase, such as DGA1; and a lecithin cholesterol acyl transferase, such as LRO1.

In an embodiment, the fungal cell is a yeast cell.

In an embodiment, the fatty acid is selected from the group consisting of stearic acid, oleic acid, palmitic acid, palmitoleic acid and a mixture thereof.

In some embodiments, the fatty acids are further processed into fatty acid-derived products, such as fatty alcohols, fatty aldehydes, fatty esters, hydrocarbons, triacylglycerides, lactones, phospholipids, etc. Preferably hydroxy fatty acids, fatty alcohols or fatty aldehydes.

This can be achieved by introduction of additional genes encoding the appropriate fatty acid modification activity. For example, conversion of fatty acids to fatty alcohols can be facilitated by expression of a fatty acyl-CoA reductase (FAR; EC 1.2.1.84). Conversion of fatty acids to hydroxy fatty acids can be achieved by expression of a fatty acid hydratase (EC 4.2.1.53) or a fatty acid hydroxylase (EC 1.11.2.4, EC 1.14.14.1, EC 1.14.15.12 or EC 1.14.15.3). Conversion of fatty acids to branched-chain fatty acids can be achieved by expression of a fatty acid methyltransferase. Conversion of fatty acids to epoxy fatty acids can be achieved by expression of a peroxygenase (EC 1.11.2.3). Conversion of free fatty acids to fatty aldehydes can be achieved by expression of carboxylic acid reductase (CAR; EC 1.2.99.6), while conversion of fatty acyl-CoAs to fatty aldehydes can be achieved by expression of an aldehyde-forming fatty acyl-CoA reductase (EC 1.2.1.50).

In some embodiments the fungal cell is genetically modified to increase the production of unsaturated fatty acids. This can be achieved by overexpressing a desaturase, for example, a fatty acyl-CoA desaturase. Examples of desaturases can include: a delta 3 desaturase, delta 4 desaturase, delta 5 desaturase, delta 6 desaturase, delta 7 desaturase, delta 8 desaturase, delta 9 desaturase, delta 10 desaturase, delta 11 desaturase, delta 12 desaturase, delta 13 desaturase, delta 14 desaturase, delta 15 desaturase, delta 16 desaturase and delta 17 desaturase. In some embodiments the desaturase might have a bifunctional or trifunctional activity with any combination of the above.

In some embodiments, a fungal cell comprises of overexpression of at least one exogenous or endogenous gene encoding a transport protein to facilitate increased secretion of fatty acids or fatty acid derived products into the media. The transport protein can be selected from the group consisting of an ATP-binding cassette (ABC) protein, a lipid transfer protein (LTP), a fatty acid transporter protein (FATP) and a plant wax ester transporter, preferably selected from the group consisting of ABCG11, ABCG12, LTPG1 and/or LTPG2. For example, ABC transporters of *Arabidopsis* such as ABCG11 and/or ABCG12 as well as lipid transfer proteins (LTPs) such as LTPG1 and LTPG2 can be introduced into a host cell. In some embodiments, fatty acid transporter (FATP) genes from species including *Saccharomyces*, *Drosophila*, Mycobacteria, or mammalian species can be introduced into a host cell. In some embodiments, the transporter protein increases the amount of fatty acids or fatty acid derived products such as fatty alcohols, fatty aldehydes, fatty esters, hydrocarbons, triacylglycerides, hydroxy fatty acids, dicarboxylic fatty acids, branched chain fatty acids, epoxy fatty acids or lactones, released into the growth media of a microorganism. Preferred transport proteins include FATP1 from *Homo sapiens* (Genbank: NP_940982; XP_352252), FATP4 from *Homo sapiens* (Genbank; NP_005085), and FAT1 from *S. cerevisiae* (Genebank: NP_009597). Expression of a transporter protein can in some embodiments also increase production of fatty acids or fatty acid derived products by a host strain. In a preferred embodiment, expression of FATP1 from *Homo sapiens* (Genbank: NP_940982) or another mammalian source in *S. cerevisiae* or *Y. lipolytica* facilitates the export into the growth medium of fatty acids or fatty acid derived products such as fatty alcohols, fatty aldehydes, fatty esters, hydrocarbons, triacylglycerides, hydroxy fatty acids, dicarboxylic fatty acids, branched chain fatty acids, epoxy fatty acids or lactones. In another preferred embodiment, expression of FATP4 from *Homo sapiens* (Genbank; NP_005085) or another mammalian source in *S. cerevisiae* or *Y. lipolytica* facilitates the export into the growth medium of fatty acids or fatty acid derived products such as fatty alcohols, fatty aldehydes, fatty esters, hydrocarbons, triacylglycerides, hydroxy fatty acids, dicarboxylic fatty acids, branched chain fatty acids, epoxy fatty acids or lactones. In yet another preferred embodiment overexpression of FAT1 from *S. cerevisiae* Genebank: NP_009597) in *S. cerevisiae* or *Y. lipolytica* facilitates the export into the growth medium of fatty acids or fatty acid derived products such as fatty alcohols, fatty aldehydes, fatty esters, hydrocarbons, triacylglycerides, hydroxy fatty acids, dicarboxylic fatty acids, branched chain fatty acids, epoxy fatty acids or lactones. Expression/overexpression of transporter proteins to increase secretion/production of fatty acids or fatty acid derived products such as fatty alcohols, fatty aldehydes, fatty esters, hydrocarbons, triacylglycerides, hydroxy fatty acids, dicarboxylic fatty acids, branched chain fatty acids, epoxy fatty acids or lactones, can be combined with any of the embodiments outlines above, or be completely independent.

In an embodiment, the fungal cell is capable of producing more than 100 mg of fatty acids per L of culture medium, and/or more than 10 mg of fatty acids per g dry cell weight (DCW).

In a particular embodiment, the fungal cell is capable of producing more than 250 mg, preferably more than 500 mg, and more preferably more than 750 mg, such as more than 1 g of fatty acids per L of culture medium.

In an alternative or additional particular embodiment, the fungal cell is capable of producing more than 15 mg, preferably more than 25 mg, and more preferably more than 30 mg fatty acid per g CDW.

The above described embodiments may be combined.

Other aspects of the invention provide methods for the production of fatty acids and/or fatty acid-derived products. Such methods comprises culturing a fungal cell according to any of the embodiments in a culture medium and in culture conditions suitable for production of the fatty acid and/or fatty acid-derived product by the fungal cell. The method also comprises collecting the fatty acid and/or fatty acid-derived product from the culture medium and/or the fungal cell.

The fatty acid-derived product is preferably selected from the group consisting of fatty alcohols, fatty aldehydes, fatty esters, hydrocarbons, triacylglycerides, lactones, phospholipids and a mixture thereof, preferably from the group consisting of fatty alcohols, fatty aldehydes, fatty esters, and a mixture thereof, and more preferably from the group consisting of hydroxy fatty acids, fatty alcohols, fatty aldehydes, and a mixture thereof.

In an embodiment, the culture medium is nitrogen-limited.

In an embodiment, the production process is composed of a growth phase, where the fungal cell is cultivated in the presence of high levels of the carbon source, e.g., glucose, and a production phase, where the fungal cell is cultivated in limiting conditions of the carbon source. This can be achieved, for example in a fed-batch process.

EXAMPLES

Example 1: Metabolic Engineering of the Acetyl-CoA Supply Results in High Production of Free Fatty Acids (FFA) in Fungal Cells This example shows that fatty acid production in a fungal cell can be increased by improving the conversion of pyruvate to acetyl-CoA through novel modifications in the acetyl-CoA metabolism. In particular, mitochondrial citrate synthesis was enhanced. The resulting citrate could be used by the enzyme ATP:citrate lyase (ACL), which cleaves citrate to oxaloacetate and acetyl-CoA. Acetyl-CoA is in turn used for the production of fatty acids. Acetyl-CoA Carboxylase (ACC) catalyzes the first step in fatty acids formation from acetyl-CoA.

Genetic modifications in yeast were carried out via promoter replacement, deletion of genes and integration of expression cassettes. Standard molecular biology methods were used, including the use of integration cassettes, use of the selective markers Ura, His and Kanamycin and marker loop out as described in David and Siewers, 2015.

As background yeast strain the strain YJZ45 (CEN.PK 113-11C (MATa; MAL2-8c; SUC2; his3 Δ1; ura3-52; hfd1Δ; pox1Δ; faa1Δ; faa4Δ; ura3Δ::HIS3+MmACL+ RtME+CTP1+'MDH3+tTesA+'tesA; URA3Δ::RtFAS1+ RtFAS2+amdSym)) was used. Genetic modifications included promoter replacement in front of various genes including PYC1 (from −200 bp to 0 bp), ACC1 (from −481 bp to 0 bp), MP3, MP2, YHM2 replacing the native promoter with the constitutive active TEF1, PGK1 and TPI promoter, respectively. Heterologous expression of AnACL and RtCIT1 was facilitated via genomic integration of GAL1p-ACLa and GAL10p-ACLb, and HXT7p-RtCIT1 expression cassettes.

Yeast strains for preparation of competent cells were cultivated in YPD consisting of 10 g/L yeast extract (Merck Millipore, Billerica, MA, USA), 20 g/L peptone (Difco) and 20 g/L glucose (Merck Millipore). Constructed plasmids and integration cassettes were transformed into respective yeast strains via the Lithium acetate method as previously described (Gietz et al., 2007). Strains containing URA3-based plasmids or cassettes were selected on synthetic complete media without uracil (SC-URA), which consisted of 6.7 g/L yeast nitrogen base (YNB) without amino acids (Formedium, Hunstanton, UK), 0.77 g/L complete supplement mixture without uracil (CSM-URA, Formedium), 20 g/L glucose (Merck Millipore) and 20 g/L agar (Merck Millipore). The URA3 maker was removed and selected against on 5-FOA plates, which contained 6.7 g/L YNB, 0.77 g/L CSM-URA and 0.8 g/L 5-fluoorotic acid. Shake flask batch fermentations for production of free fatty acids were carried out in minimal medium containing 2.5 g/L $(NH4)_2SO_4$, 14.4 g/L $KH_2PO_4$, 0.5 g/L $MgSO_4·7H_2O$, 30 g/L glucose, trace metal and vitamin solutions supplemented with 60 mg/L uracil if needed. Cultures were inoculated, from 24 h precultures, at an initial $OD_{600}$ of 0.1 with 15 ml minimal medium in 100 mL unbaffled flask and cultivated at 200 rpm, 30° C. for 72 h. Glucose feed beads (SMFB63319, Kuhner Shaker, Basel, Switzerland) with a release rate of 0.25 g/L/h were added to the medium to replace the 30 g/L glucose if needed, and the culture time is 80 h for totally release the glucose. For nitrogen restricted culture, 1.4 g/L $(NH4)_2SO_4$ were used.

FFA titers in whole-cell culture (only FFA was measured in this study) were quantified following previously published methods (Zhou et al., 2016). Specifically, 0.2 ml of cell culture (or an appropriate volume of cell culture diluted to 0.2 ml) were transferred to glass vials from 72 h or 80 h incubated cultures, then 10 ml 40% tetrabutylammonium hydroxide (base catalyst) was added immediately followed by addition of 200 ml dichloromethane containing 200 mM methyl iodide as methyl donor and 100 mg/L pentadecanoic acid as an internal standard. The mixtures were shaken for 30 min at 1,200 rpm by using a vortex mixer, and then centrifuged at 4,000×g to promote phase separation. A 150 ml dichloromethane layer was transferred into a GC vial with glass insert, and evaporated 3 h to dryness. The extracted methyl esters were resuspended in 150 ml hexane and then analyzed by gas chromatography (Focus GC, Thermo Fisher Scientific) equipped with a Zebron ZB-5MS GUARDIAN capillary column (30m×0.25 mm×0.25 mm, Phenomenex) and a DSQII mass spectrometer (Thermo Fisher Scientific). The GC program was as follows: initial temperature of 40° C., hold for 2 min; ramp to 130° C. at a rate of 30° C. per minute, then raised to 280° C. at a rate of 10° C. per min and hold for 3 min. The temperatures of inlet, mass transfer line and ion source were kept at 280, 300 and 230° C., respectively. The injection volume was 1 µl. The flow rate of the carrier gas (helium) was set to 1.0 ml/min, and data were acquired at full-scan mode (50-650 m/z). Final quantification was performed using the Xcalibur software.

The extracellular glucose, glycerol, ethanol and organic acid concentrations were determined by high-performance liquid chromatography analysis. In detail, a 1.5 ml broth sample was filtered through a 0.2 mm syringe filter and analyzed on an Aminex HPX-87G column (Bio-Rad) on an Ultimate 3000 HPLC (Dionex Softron GmbH). The column was eluted with 5 mM $H_2SO_4$ at a flow rate of 0.6 ml/min at 45° C. for 26 min.

Figure 2:
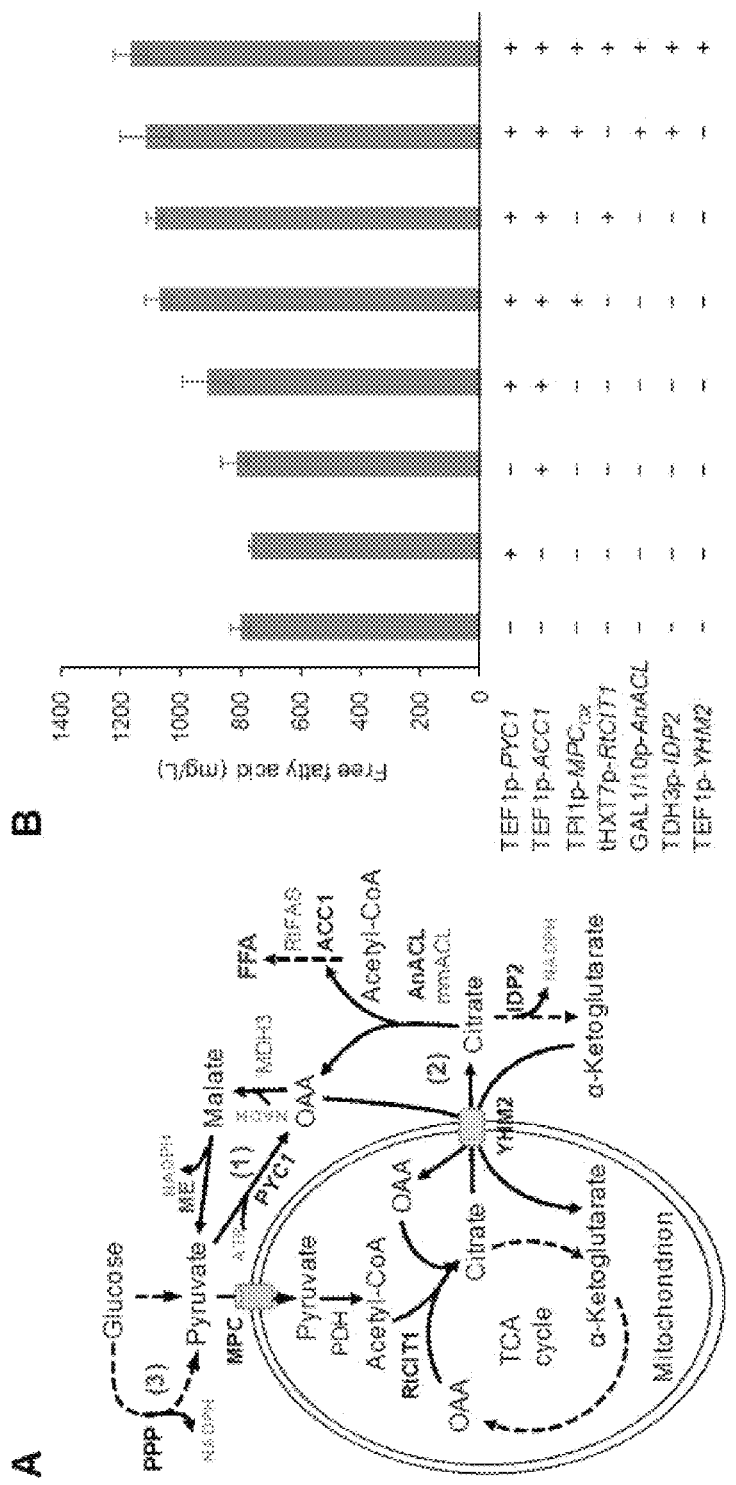
FIG. 2: Metabolic engineering for enhancing the supply of the cytosolic acetyl-CoA. (A) Schematic illustration of the subcellular flux trafficking and engineering targets. (B) FFA production obtained with engineered strains in shake flasks after 72 h cultivation at 200 rpm, 30° C. on 30 g/L glucose. All data is presented as mean±SD of biological triplicates.

Overexpression of pyruvate carboxylase (PYC1) to ensure efficient formation of oxaloacetate required for citrate production did not result in a significant increase in FFA production (FIG. 2B). Neither did overexpression of acetyl-CoA carboxylase (ACC1) (FIG. 2B). However, combination of both modifications surprisingly resulted in a 14% increase in production of free fatty acids (FIG. 2B). When MPC1 and MPC3 (which together form the MPCox pyruvate transport complex) were overexpressed in a strain overexpressing PYC1 and ACC1 in order to improve transport of pyruvate to the mitochondria, a further 17% improvement in production was observed (FIG. 2B). When citrate synthase from *Rhodosporidium toruloides* (RtCIT1) was overexpressed in a strain overexpressing PYC1 and ACC1, a further 18% improvement in fatty acid titers was observed compared to the parental strain (FIG. 2B). Combining overexpression of PYC1, ACC1, MPC1, MPC3 and YHM2 with heterologous expression of AnACL and RtCIT1 lead to a 256% increase in FFA production compared to a strain only overexpressing PYC1 and ACC1, and a 46% improvement compared to the starting strain (FIG. 2B).

Example 2: Further Fine-Tuning of Gene Expression Improves Free Fatty Acid (FFA) Production by Fungal Cells Additional engineering was done through fine tuning of gene expression of the gene PGI1 (from −405 bp to 0 bp) involved in glycolysis and IDH2 (from −456 bp to 0 bp) in TCA cycle through promoter replacement with promoters displaying lower activity. All genetic modifications, cultivations, and analysis were performed as described in Example 1.

For PGI1, the promoter replacement was done through integration cassettes with the promoters of ISU1 (SEQ ID NO: 15), ATP14 (SEQ ID NO: 16), QCR10 (SEQ ID NO: 17), COX9 (SEQ ID NO: 18), NAT1 (SEQ ID NO: 19) and HXT1 (SEQ ID NO: 20), which were amplified from CEN.PK113-5D genomic DNA. Additionally integration cassettes were constructed for overexpression of Pentose Phosphate Pathway associated genes, including: $P_{HXT1}$-TKL1, $P_{PGK1}$-TAL1, $P_{TEF1}$-ZWF1, $P_{TDH3}$-GND1.

Figure 3A:
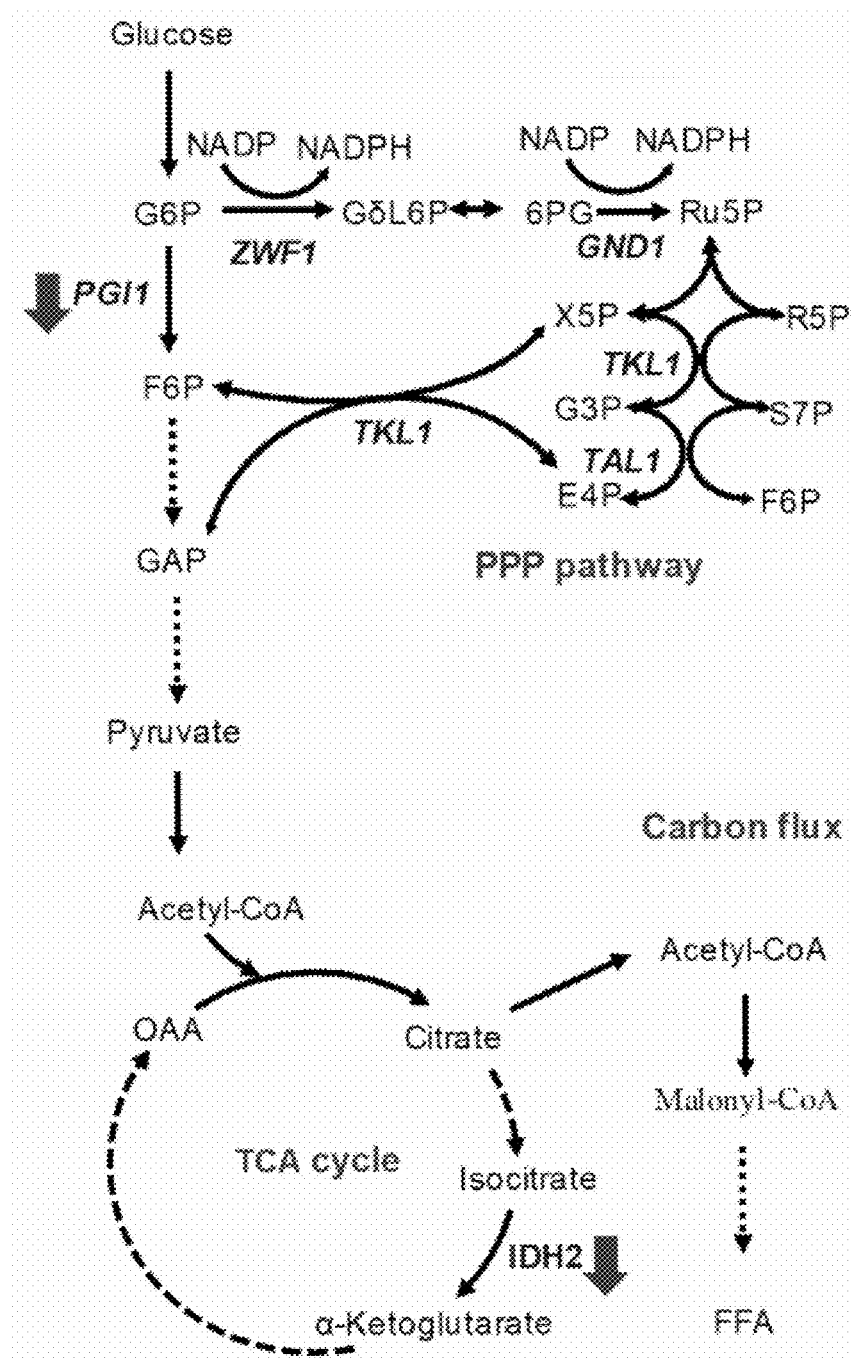
FIGS. 3A-3C: Fine-tuning the pentose phosphate pathway (PPP), tricarboxylic acid cycle (TCA) cycle and glycolysis for FFA production.
Figure 3B:
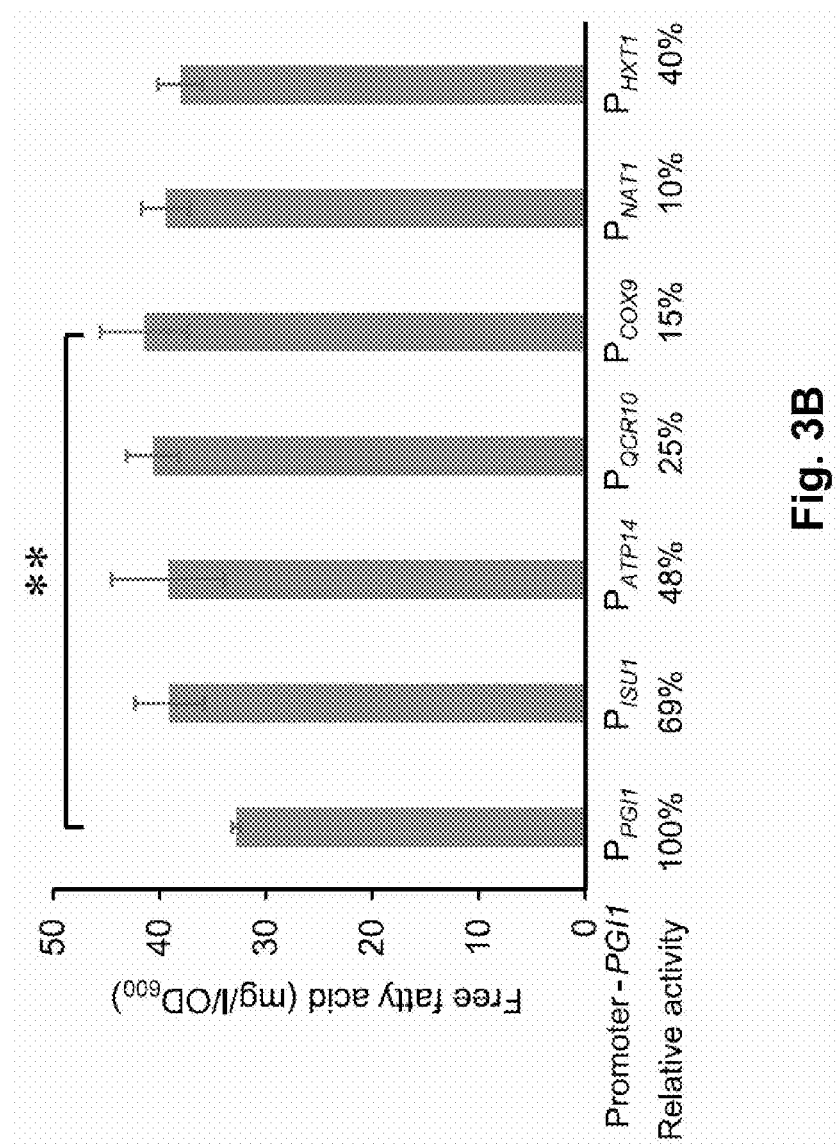

Replacing the native promoter of PGI1 with a weaker promoter increased FFA production by 20-27%, with the COX9 promoter displaying the best results (FIG. 3B).

Figure 3C:
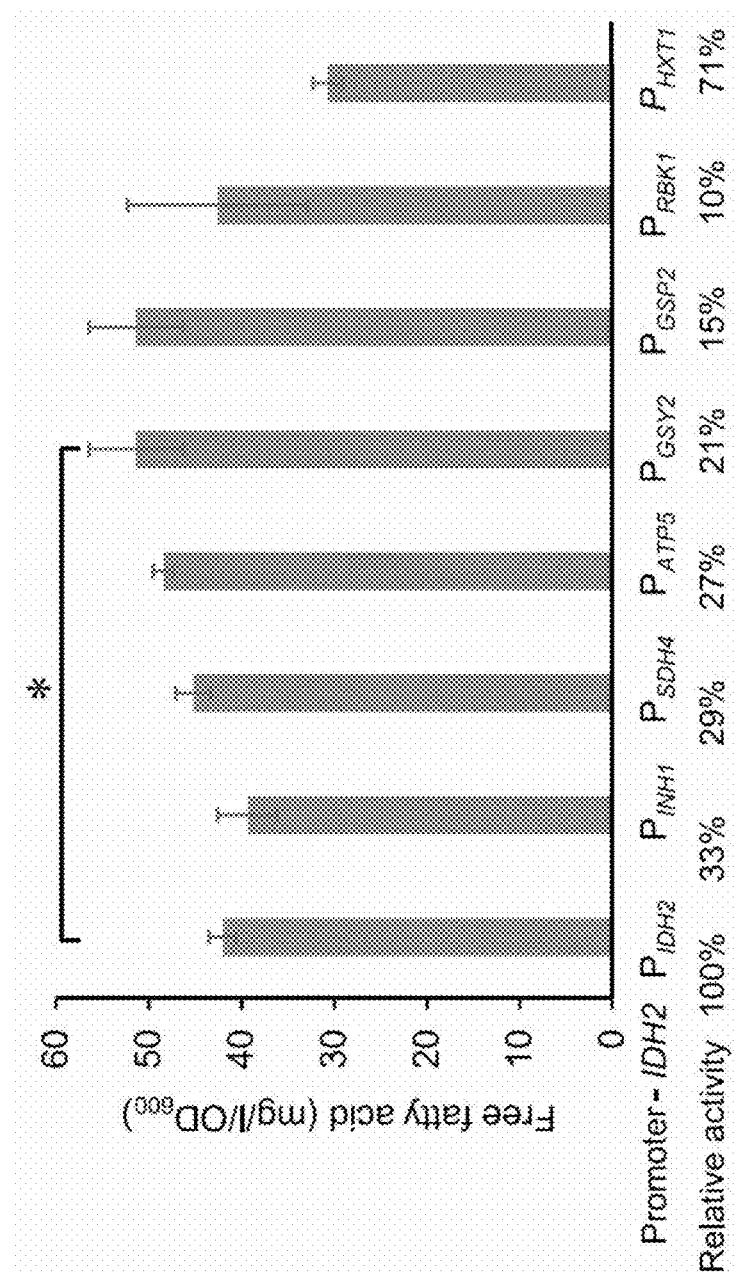

For IDH2, the promoter replacement was done through integration cassettes with the promoters of INH1 (SEQ ID NO: 21), SDH4 (SEQ ID NO: 22), ATP5 (SEQ ID NO: 23), GSY2 (SEQ ID NO: 24), GSP2 (SEQ ID NO: 25), RBK1 (SEQ ID NO: 26) and HXT1 (SEQ ID NO: 20), which were amplified from CEN.PK113-5D genomic DNA. Replacing the native promoter of IDH2 with a weaker promoter increased FFA production by up to 22%, with the GSY2 and GSP2 promoters displaying the best results (FIG. 3C).

The resulting strain TY36 having the following genetic background: MATa; MAL2-8c; SUC2; his3 Δ1; ura3-52; hfd1Δ; pox1Δ; faa1Δ; faa4Δ; ura3Δ::HIS3+MmACL+RtME+CTP1+'MDH3+tTesA+'tesA; URA3Δ::RtFAS1+RtFAS2+amdSym; acc1:: TEF1p-ACC1; pyc1::TEF1p-PYC1; X1-4:: MPC1+MPC3; gal80Δ; X1-2:: AnACL; gal1Δgal7Δgal10Δ:: RtCIT1+IDP2+YHM2; pgi1Δ:: COX9p-PGI1+GND1+TKL1+TAL1+ZWF1; idh2Δ:: GSY1p-IDH2, which combined all modifications was tested under fed-batch conditions (see Example 3).

Example 3: Growth-Production De-Coupling

Figure 4:
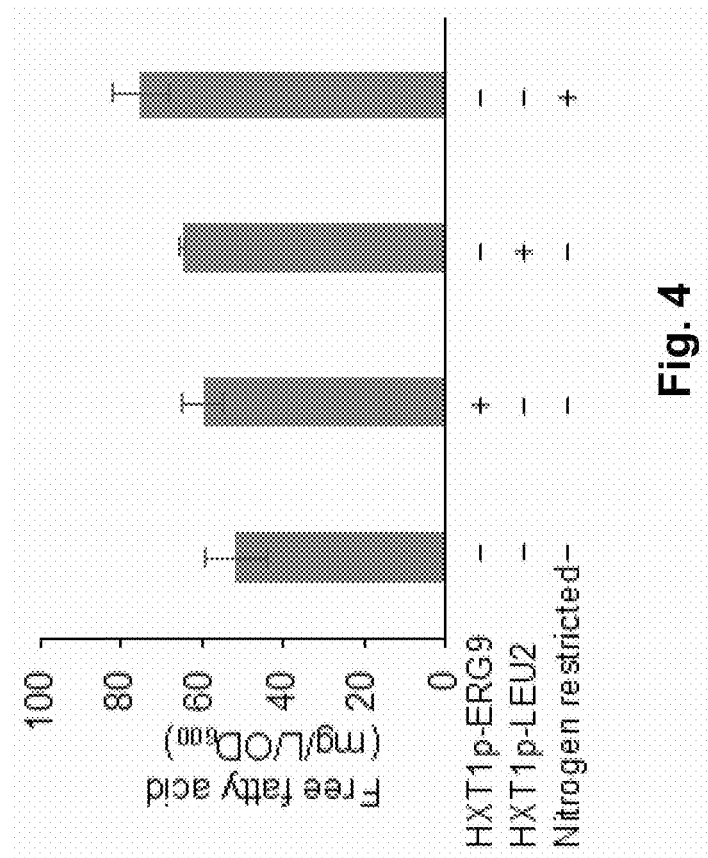
FIG. 4: FFA production was further improved by growth decoupling. Limited cell growth by downregulation of essential genes and nitrogen restriction improved FFA production. The strains were cultivated in shake flasks for 80 h at 200 rpm, 30° C. with glucose feed beads (corresponding to 30 g/L glucose). All data represent the mean±SD of biological triplicates.
Figure 5:
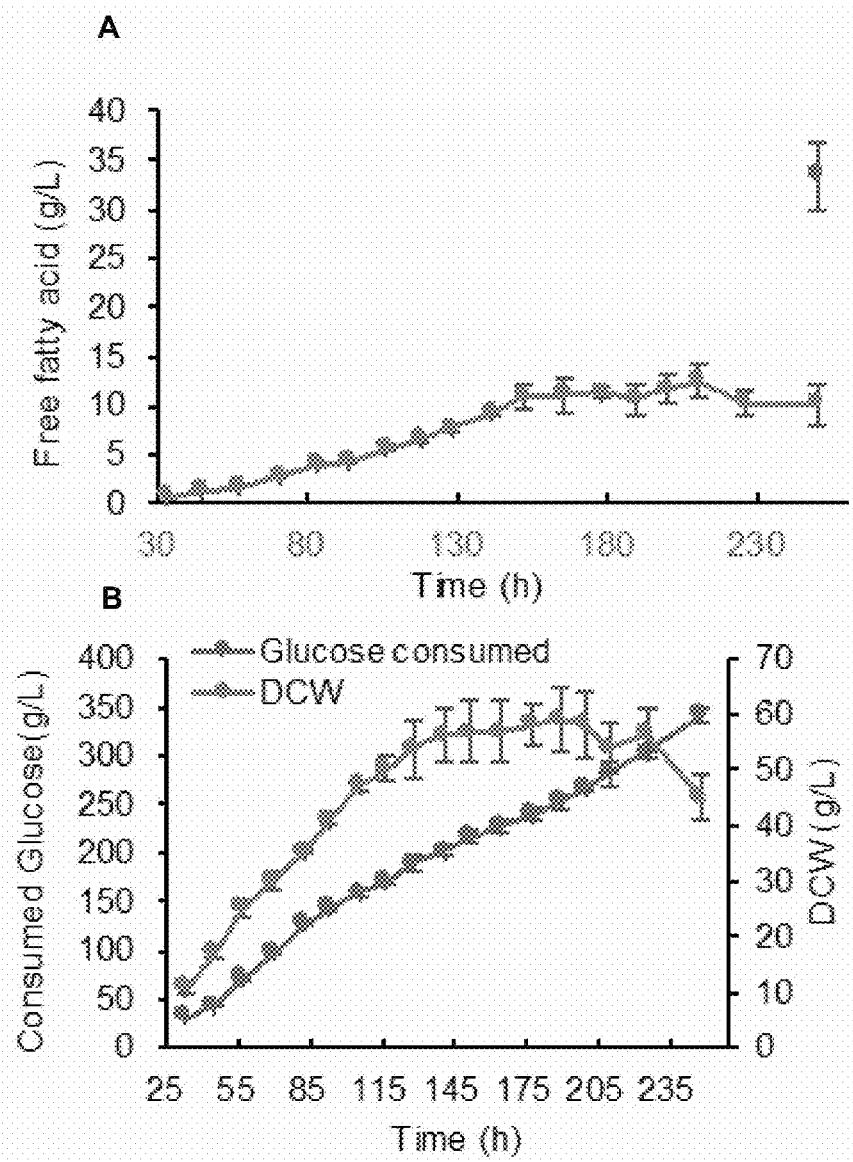
FIG. 5: FFA production was further improved by growth decoupling. (A) Fed-batch fermentation of strain TY36 with glucose limited and nitrogen restriction. Time courses of FFA titers and end point are shown. Overall FFA production at the end of fermentation is 35 g/L. (B) Time courses of DCW (upper curve) and consumed glucose (lower curve) during the fermentation are shown.

In oleaginous fungi, lipid overproduction is always initiated by growth stagnation that is triggered by limitation of nutrients such as nitrogen, which is due to the fact that biomass formation competes for carbon and energy. We therefore decoupled FFA production from cell growth through limiting cell growth by dynamically controlling the expression of essential genes under the HXT1 promoter, whereby we can tune cell growth by controlling the glucose concentration. The native promoter of LEU2 (from −195 bp to 0 bp) and ERG9 (from −138 bp to 0 bp) were replaced by the HXT1 promoter using standard techniques involving integration cassettes, marker selection and removal as previously described in Example 1. Genetic modifications, cultivation and analytics were carried out as described in Example 1. The promoter replacement lead to 15% increase in free fatty acid production in case of the ERG9 promoter and 25% for the LEU2 promoter (FIG. 4). Cultivation of this particular strain without any promoter replacement regarding LEU2 and ERG9 but under nitrogen limitation lead to 47% increase in free fatty acid production (FIG. 4). A fed-batch cultivation of strain TY36 under nitrogen limiting conditions was carried out leading to very high titers of free fatty acids of 35 g/L (FIG. 5). The batch and fed-batch fermentations for free fatty acid production were performed in 1.0 L bioreactors, with an initial working volume of 0.25 L, in a DasGip Parallel Bioreactors System (DasGip). The initial batch fermentation was carried out in minimal medium containing 5 g/L $(NH_4)_2SO_4$, 3 g/L $KH_2PO_4$, 0.5 g/L $MgSO_4·7H_2O$, 60 mg/L URA, 20 g/L glucose, trace metal and vitamin solutions. The temperature, agitation, aeration and pH were monitored and controlled using a DasGip Control 4.0 System. The temperature was kept at 30° C., initial agitation set to 800 rpm and increased to maximally 1,200 rpm depending on the dissolved oxygen level. Aeration was initially provided at 36 sl/h and increased to maximally 48 sl/h depending on the dissolved oxygen level. The dissolved oxygen level was maintained above 30%, the pH was kept at 5.6 by automatic addition of 4 M KOH and 2 M HCl. The aeration was controlled and provided by a DasGip MX4/4 module. The composition of the off-gas was monitored using a DasGip Off gas Analyzer GA4. Addition of the acid, base, and glucose feed was carried out with DasGip MP8 multi-pump modules (pump head tubing: 0.5 mm ID, 1.0 mm wall thickness). The pumps, pH and DO probes were calibrated before the experiment. During the fed-batch cultivation, the cells were initially fed with a 200 g/L glucose solution with a feed rate that was exponentially increased (p=0.05/h) to maintain a constant biomass-specific glucose consumption rate. The used minimal medium contained 15 g/L $(NH_4)_2SO_4$, 9 g/L $KH_2PO_4$, 1.5 g/L $MgSO_4 \cdot 7H_2O$, 180 mg/L uracil, 3× trace metal and 3× vitamin solution. When the volume of the fermentation broth reached 0.4-0.45 L, the feed solution was switched to the following composition: 25 g/L $(NH_4)_2SO_4$, 15 g/L $KH_2PO_4$, 2.5 g/L $MgSO_4 \cdot 7H_2O$, 300 mg/L uracil, 600 g/L glucose, 5× trace metal and 5× vitamin solution. The initial feed rate was calculated using the biomass yield and concentration that were obtained during prior duplicate batch cultivations with these strains. The feeding was started once the dissolved oxygen level was higher than 30%. Dry cell weight measurements were performed by filtrating 3-5 ml of broth through a weighed 0.45 mm filter membrane (Sartorius Biolab, Gottingen, Germany) and measuring the weight increase after drying for 48 h in a 65° C. oven. The filter was washed once before and three times after filtrating the broth with 5 ml deionized water. During fermentation, floating dead cells and fatty acid residues were found to stick to the inner wall or the bottom of the fermenter. After fermentation, all particles were resuspended in the fermentation culture to accurately measure the total FFA production. Measurements were performed three times.

Example 4: Abolishment of Ethanol Production

Ethanol is often a side-product of fermentation and might be undesired if production of fatty acids is the main goal. Pyruvate decarboxylases (PDC1, PDC5, and PDC6) catalyze the decarboxylation of pyruvate to acetaldehyde, which plays a key role in alcoholic fermentation in S. cerevisiae. Deletion of these genes leads to abolishment of ethanol production. However, a PDC-negative strain with a triple deletion of all PDC genes is unable to grow on glucose as the sole carbon source.

Figure 6B:
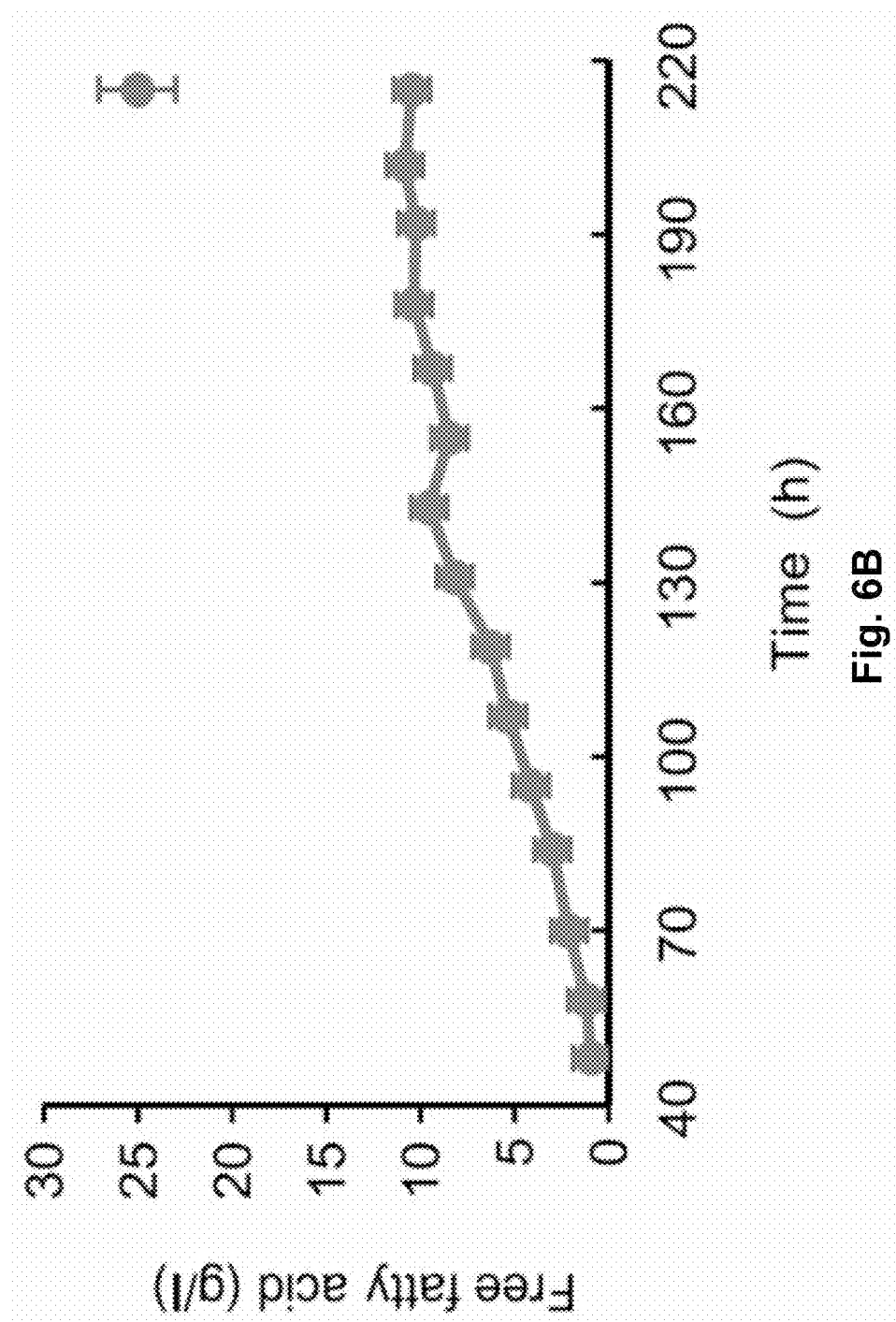
Figure 6C:
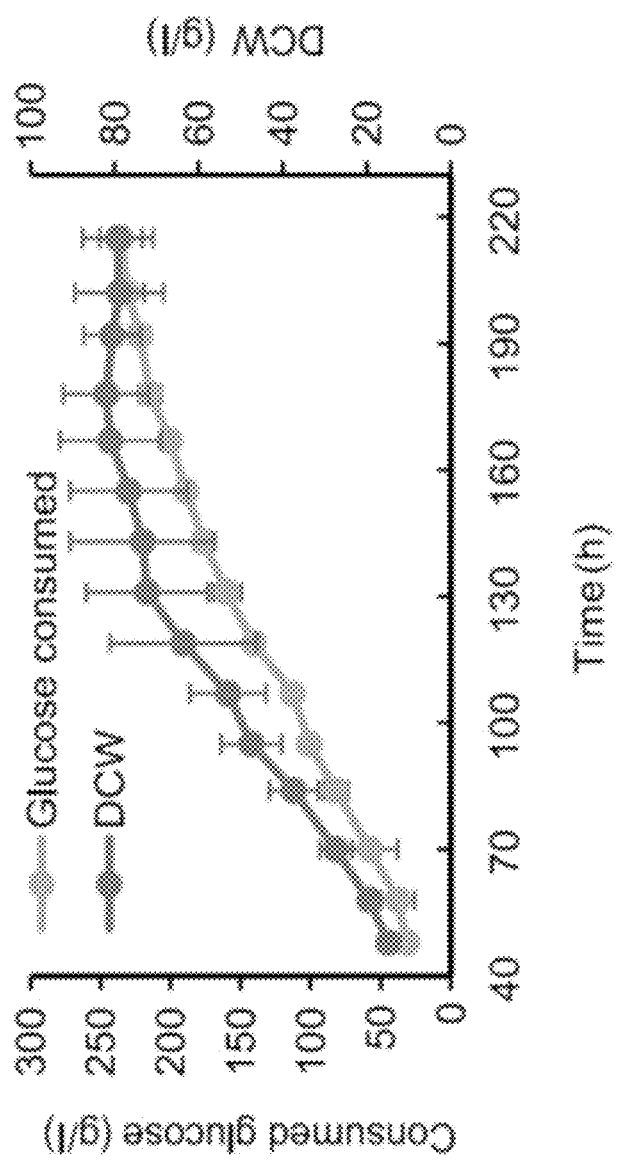

PDC1, PDC5 and PDC6 were deleted from the fatty acid-producing strain TY36 using the methodology outlined in Example 1, resulting in strain TY53. However, the resulting strain was unable to grow on glucose. In order to facilitate growth on glucose, the strain was evolved using Adaptive Laboratory Evolution. The adaptive evolution of TY53 (TY36 pdc1Δ, pdc5Δ, pdc6Δ) toward growth on glucose as the sole carbon source were performed in three independent culture lines in 100 mL shake flasks with 15 mL medium at 30° C., which involved two phases. In the first phase, strains were cultivated in minimal medium containing 0.5% glucose and 2% ethanol and then serially transferred every 48 or 72 h using minimal medium with a gradually decreased ethanol concentration and increased glucose concentration for 45 days. Subsequently, the strains were transferred into minimal medium containing 2% glucose as the sole carbon source and evolved for increased growth by serial transfer every 48 or 72 h for 50 days. Several strains were isolated from the evolved populations and tested. The evolved TY53 strains could grow on glucose. The performance of the evolved strains was compared to a wild-type strain (CEN.PK113-5D) and an evolved PDC-negative wild-type strain (evolved PDC-CEN.PK) (FIG. 6A). When cultured under shake-flask conditions (as described in Example 1), the evolved TY53 strains could produce fatty acids, produced less pyruvate than evolved PDC-CEN.PK and did not produce ethanol (FIG. 6A). When grown under fed-batch conditions (performed as described in Example 3) the strains produced up to 25 g/L of free fatty acids (FIG. 6B) and accumulated biomass (FIG. 6C)

To evaluate the underlying mechanisms, total genomic DNA of selected strains was extracted by using the Blood & Cell Culture DNA Kit (QIAGEN). Then DNA was prepared using the Illumina TruSeq Nano DNA HT 96 protocol, according to the manufacturer's instructions. The samples were sequenced using an Illumina NextSeq High kit, paired-end 300 cycles (2×150 bp). Each sample was represented by 2.2-6.4 million sequence reads. Breseq (Deatherage and Barrick, 2014) 0.30.2 with bowtie (Langmead and Salzberg, 2012) 2.2.8 was used to map the reads of each sample to the genome of S. cerevisiae CEN.PK 113-7D (Jenjaroenpun et al., 2018). The option junction-alignment-pair-limit set to 0 (no limit) to ensure all possible new junctions were evaluated. The sequencing data for the initial strain (TY36) was also processed with breseq and used as a reference for removing false-positives from the sample analysis.

Figure 7:
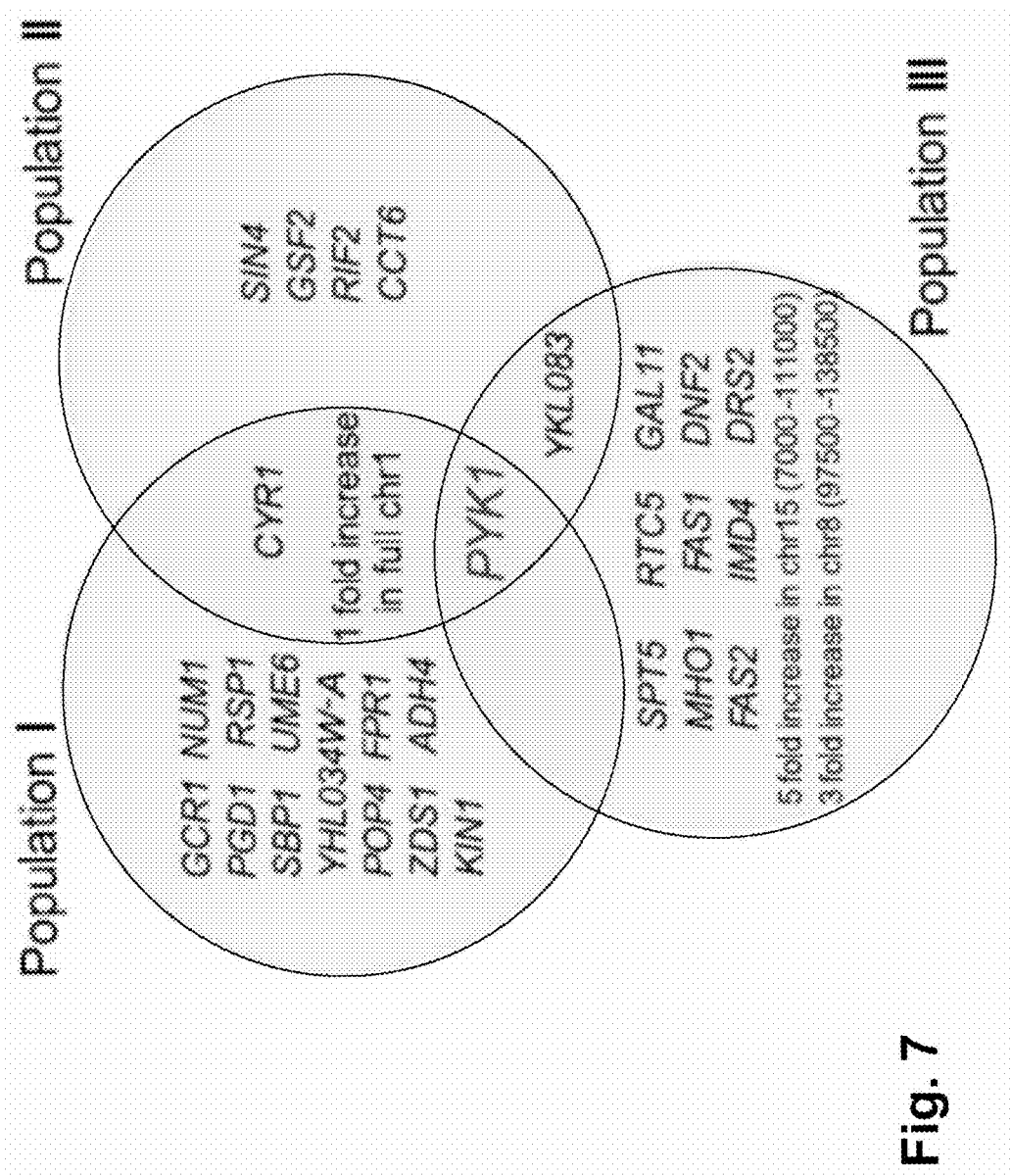
FIG. 7: Venn diagram summarizing the intersection among mutations accumulated in the evolved strains TY53 isolated from three distinct evolution experiments.
Figure 8:
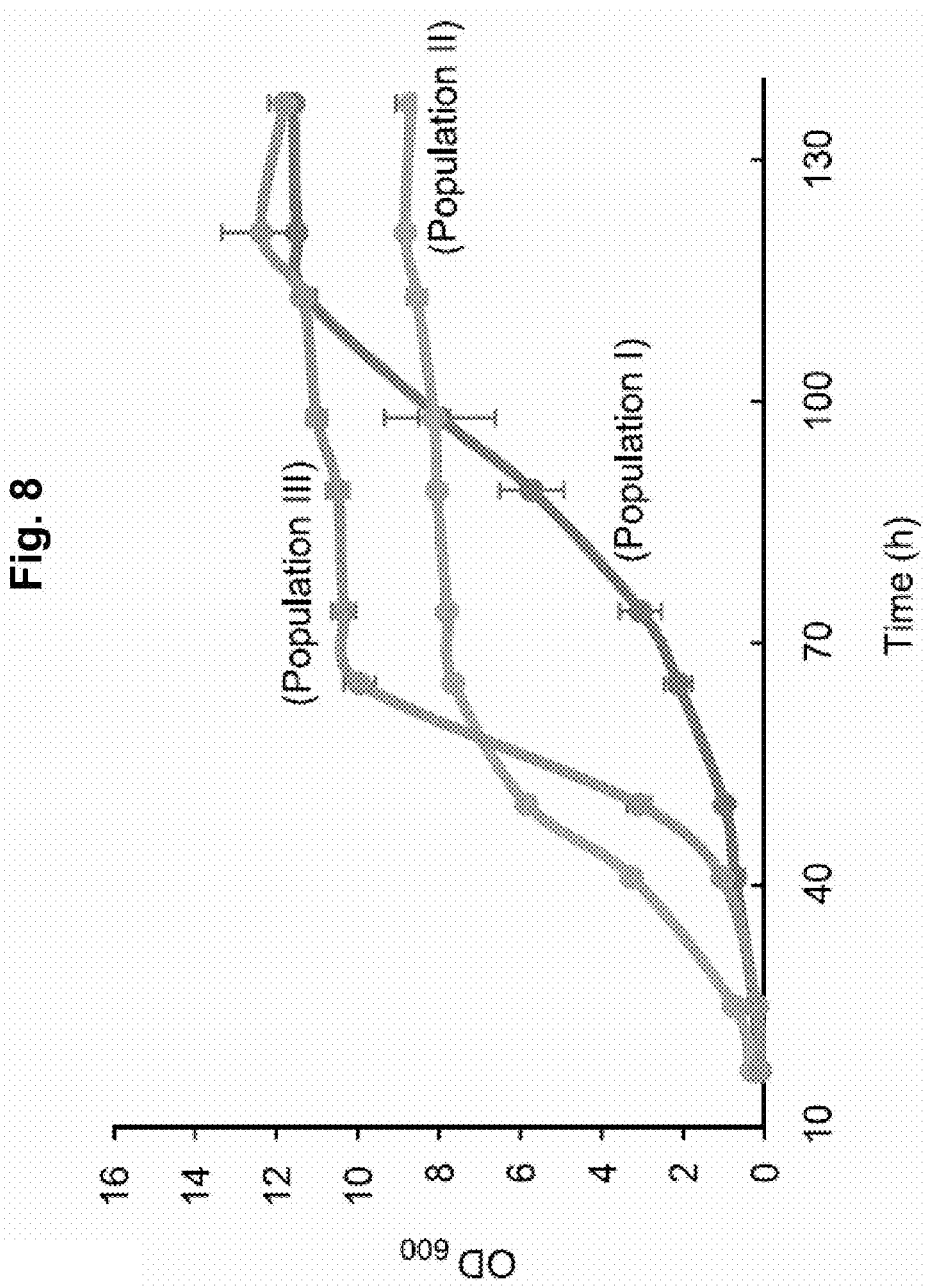
FIG. 8: Growth curves for the three evolved TY53 populations. The strains were cultured in shake flasks at 200 rpm, 30° C. with 20 g/L glucose. All data represent the mean±SD of biological triplicates.

The mutations found in the three clones are shown in FIG. 7. The growth of each clone (under shake-flask conditions, as described in Example 1) is shown in FIG. 8.

It was found that mutations in pyruvate kinase (PYK1), also known as CDC19 in S. cerevisiae, occurred in all three evolved clones: two nonsense mutations (R68* and K196*) and a missense mutation (R911). PYK1 (CDC19) is the major pyruvate kinase which converts phosphoenolpyruvate (PEP) and ADP to pyruvate and ATP. PYK1 is tightly regulated and activated by fructose-1,6-bisphosphate (FBP) and considered as a key control point of glycolytic flux. The mutations in PYK1 across the evolved mutants suggested that decease in PYK1 activity is important for growth on glucose.

Figure 9:
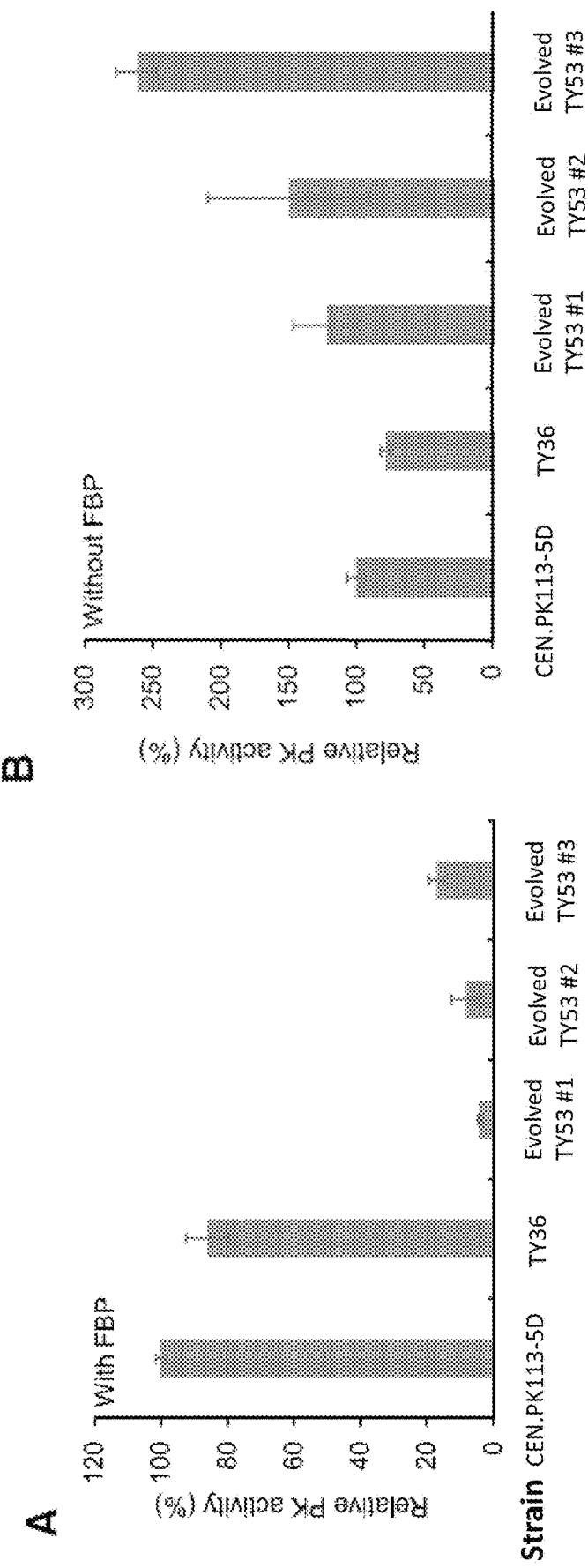
FIG. 9: Activity of pyruvate kinase (PK). (A) The overall activity of PK in the evolved strains was downregulated. Fructose-1,6-bisphosphate (FBP) was added as an activator of PYK1. (B) The activity of PYK2 in the evolved strains was increased. Here, no FBP was added as an activator.
Figure 10:
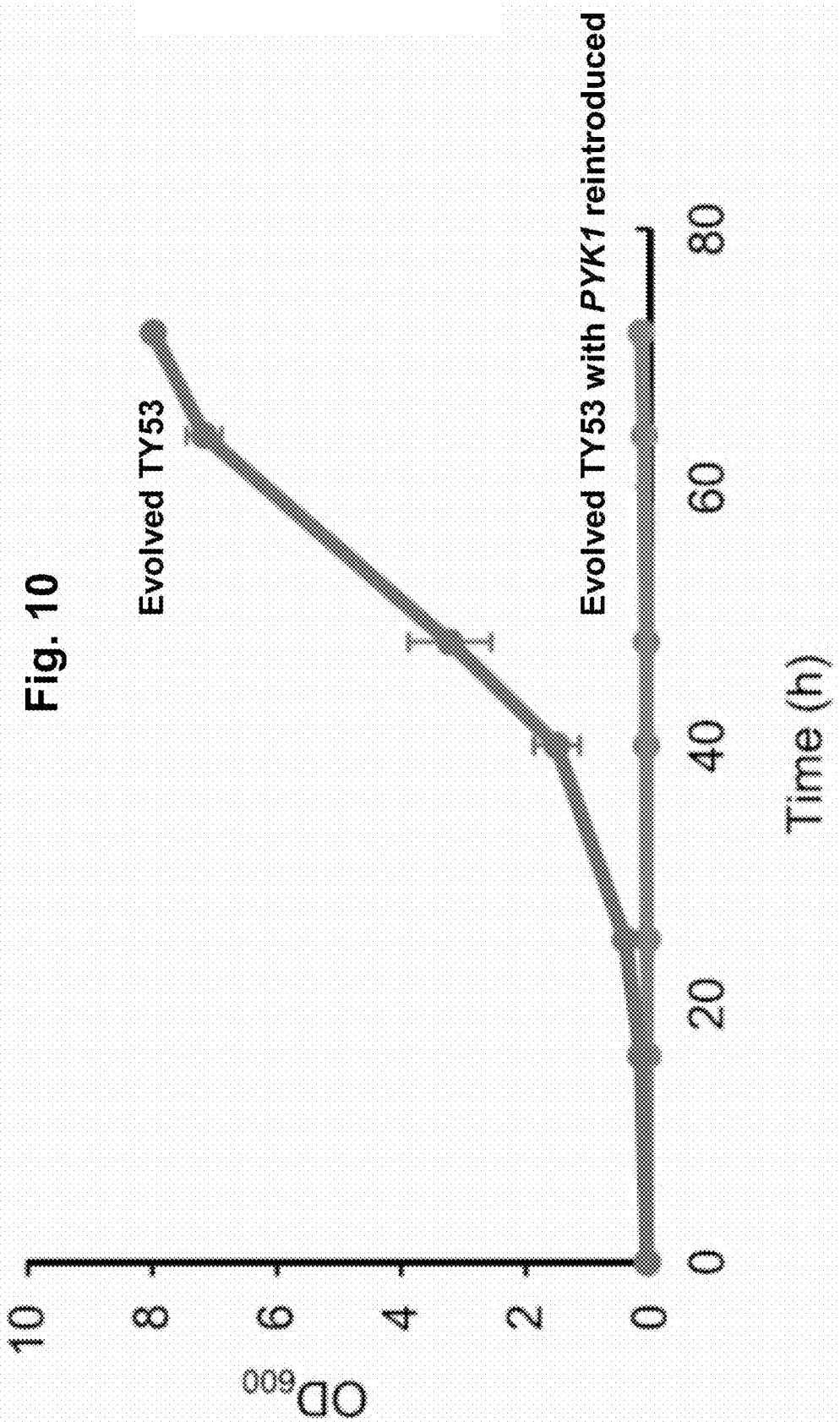
FIG. 10: The evolved phenotype was abolished by expression of PYK1. The strains were precultured in shake flasks at 200 rpm, 30° C. with 20 g/L glucose for 3 days to remove intracellular stores of C2 metabolites, then subcultured in shake flasks at 200 rpm, 30° C. with 20 g/L glucose for measurement of optical density at 600 nm ($OD_{600}$). All data represent the mean±SD of biological triplicates.
Figure 11:
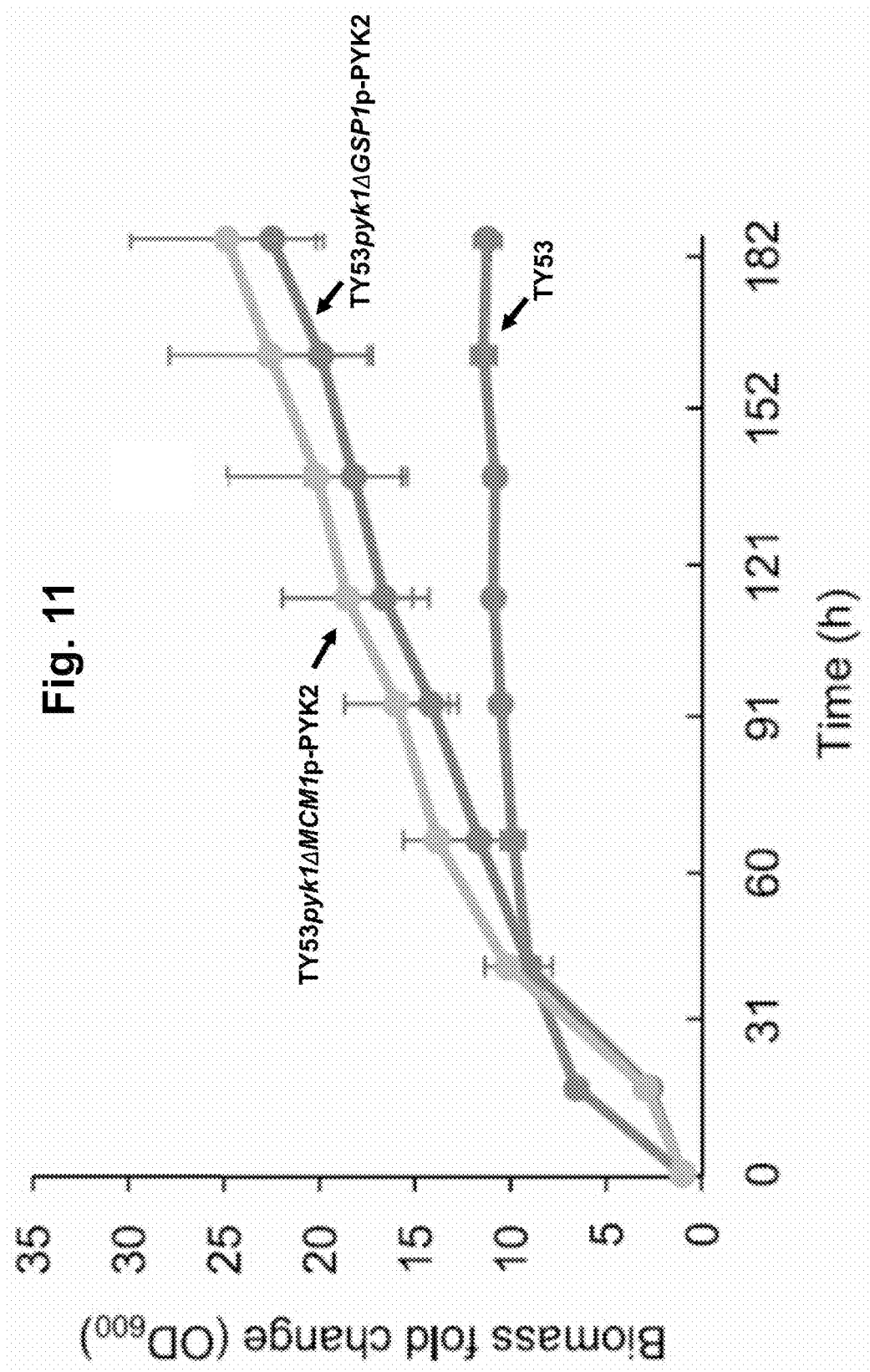
FIG. 11: Downregulation of FBP-sensitive and upregulation of FBP-insensitive pyruvate kinase enabled the growth of PDC-negative strain in high concentration of glucose. The strains were cultured in shake flasks at 200 rpm, 30° C. with 20 g/L glucose and 0.5% (v/v) ethanol. All data represent the mean±SD of biological triplicates. The activity of GSP1 promoter is 6-fold of native PYK2 promoter. The activity of MCM1 promoter is 3-fold of native PYK2 promoter. The PYK1 gene was deleted in TY53, then a PYK2 gene under the promoter of GSP1 or MCM1 in a low-copy plasmid was introduced into the cell to get the strain TY53 pyk1ΔGSP1p-PYK2 or TY53pyk1ΔMCM1p-PYK2.

In addition, it was found that while the evolved mutants had a much lower PYK activity in general, they had a higher PYK2 activity (FIG. 9) compared to the unevolved strain and PYK2 was found to be increased in copy number in the evolved strains. In order to confirm the role of PYK in growth on glucose, wild-type PYK1 was reintroduced into the evolved strain, which resulted in abolishment of growth in glucose medium (FIG. 10). In addition, we found that deletion of PYK1 and overexpression of PYK2 in the PDC-negative strain TY53 enabled growth on glucose (FIG. 11).

Overall, these results demonstrate that it is possible to abolish production of the by-product ethanol and maintain growth on glucose by deleting the PDC genes, down-regulating PYK1 and overexpressing PYK2.

Example 5: Overexpression of Endogenous Genes

This example demonstrates that increased production of fatty acids can be achieved through overexpression of selected endogenous genes.

The endogenous genes MPP6, ACP1, EPT1, FAA1, GEP4, GGA2, IDP3, INP54, LPP1, MCR1, ORM1, RTC3, SP07, TGL1 and YFT2 were amplified from the genomic DNA of S. cerevisiae strain IMX581 (derived from the strain CEN.PK113-5D Mans et al., 2015). The genes were integrated into the integration site X_3 (Jessop-Fabre et al., 2016) in the background strain IMX581. Promoter PTEF1 and terminator TCYC1 were used for controlling gene expression of the selected genes. Amplified genetic parts, including homologous regions and promoter-gene-terminator, were assembled into a cassette through a two-step fusion PCR procedure adapted from (Zhou et al., 2012) and transformed into strain IMX581. This resulted in 15 S. cerevisiae strains, each overexpressing one of the following genes: MPP6, ACP1, EPT1, FAA1, GEP4, GGA2, IDP3, INP54, LPP1, MCR1, ORM1, RTC3, SP07, TGL1 and YFT2.

The above strains, as well as a control strain (IMX581) not overexpressing any of the endogenous genes mentioned above, were inoculated from 48 h pre-cultures at an $OD_{600}$ of 0.1 in 25 mL minimal medium (described in Example 1) supplemented with 60 mg/L uracil in 100 mL shake flasks. Strains were cultivated at 30° C. at 200 rpm. Samples for fatty acid analysis were taken after 48 hours of cultivation and processed as described in Example 1.

Figure 12:
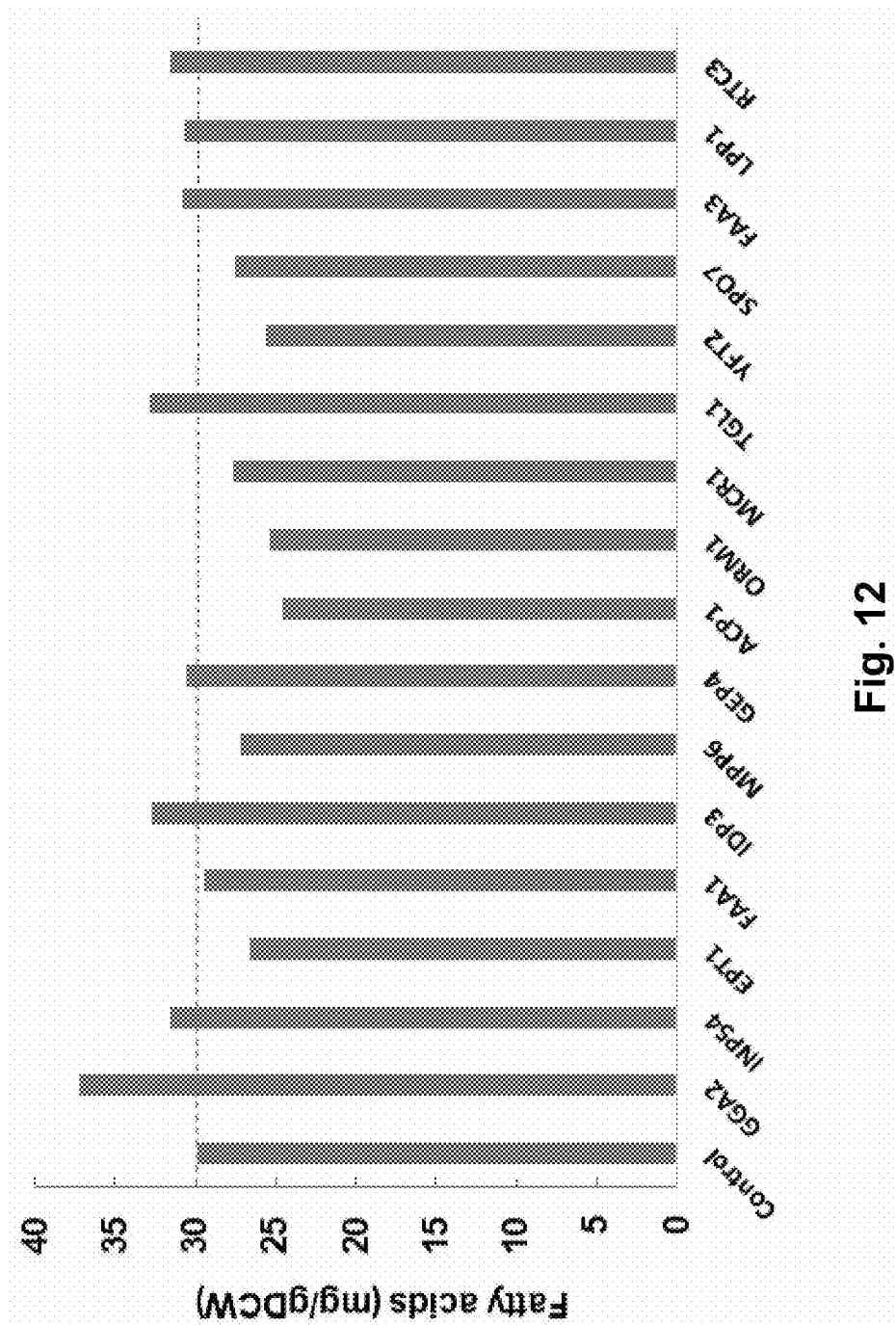
FIG. 12: Effect of individual overexpression of GGA2, INP54, EPT1, FAA1, IDP3, MPP6, GEP4, ACP1, ORM1, MCR1, TGL1, YFT2, SP07, FAA3, LPP1 and RTC3 on production of fatty acids. IMX581 is the control strain (not overexpressing any of the aforementioned genes). Strains were cultivated at 30° C. and 200 rpm and samples were taken after 48 hours. All numbers are an average of three replicates. Dashed horizontal line indicates production of control strain for easier comparison.

FIG. 12 shows the results for total fatty acid production as a consequence of overexpression of the genes described above. Individual overexpression of GGA2, INP54, IDP3, GEP4, TGL1, FAA3, LPP1 and RTC3 showed a beneficial effect on fatty acid production. Strains overexpressing these genes displayed improved fatty acid production of 24.4%, 5.5%, 9.3%, 2.1%, 9.8%, 2.8%, 2.5% and 5.6% compared to the control strain, respectively (FIG. 12). These results show that overexpression of these genes is a good strategy to improve production of fatty acids in yeast, with overexpression of GGA2 being the most promising strategy.

Figure 13:
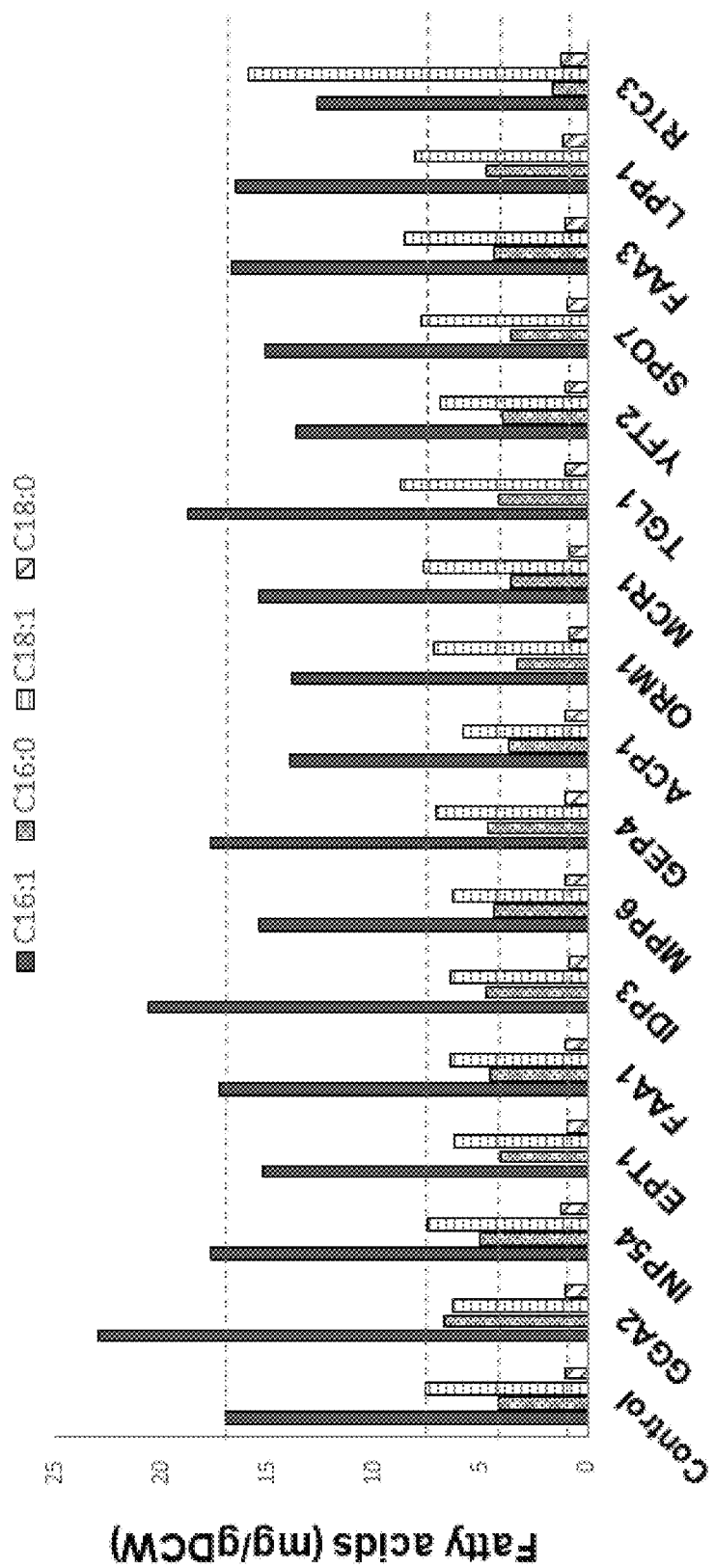
FIG. 13: Effect of individual overexpression of GGA2, INP54, EPT1, FAA1, IDP3, MPP6, GEP4, ACP1, ORM1, MCR1, TGL1, YFT2, SP07, FAA3, LPP1 and RTC3 on fatty acid composition. IMX581 is the control strain (not overexpressing any of the aforementioned genes). Strains were cultivated at 30° C. and 200 rpm. Samples were taken after 48 hours of cultivation. All numbers are an average of three replicates. C16:0 is palmitic acid, C16:1 is palmitoleic acid, C18:0 is stearic acid, C18:1 is oleic acid. Dashed horizontal lines indicate production of the respective fatty acid by the control strain for easier comparison.

While for some applications production of a mixture of different fatty acids is desirable, in some cases production of specific fatty acids is preferred. Therefore, in addition to measuring total fatty acids, the effects of the overexpression of the aforementioned endogenous genes on production of specific fatty acids, including palmitic acid (C16:0), palmitoleic acid (C16:1), stearic acid (C18:0) and oleic acid (C16:1) were quantified. These results are depicted in FIG. 13. It was found that individual overexpression of GGA2, INP54, FAA1, IDP3, GEP4, FAA3, and LPP1 increased production of palmitic acid (C16:0) by 60.6%, 21.4%, 8%, 13.5%, 10.4%, 3% and 13.3% compared to control, respectively (FIG. 13). It was also found that individual overexpression of GGA2, INP54, IDP3, GEP4 and TGL1 increased production of palmitoleic acid (C16:1) by 35.4%, 4.2%, 21.2%, 3.9% and 10.5% compared to control, respectively (FIG. 13). In addition, individual overexpression of TGL1, SPO7, FAA3, and RTC3 increased production of oleic acid (C18:1) by 14.5%, 2.2%, 12% and 107.8% compared to the control, respectively (FIG. 13). Finally, individual overexpression of GGA2, INP54, FAA1, MPP6, GEP4, TGL1, FAA3, LPP1 and RTC3 increased production of stearic acid (C18:0) by 6.6%, 19.5%, 2.8%, 4.8%, 3%, 2.7%, 4.7%, 14.1% and 24.6% compared to control, respectively. These results indicated that in addition to having beneficial effects on the production of fatty acids in general, several of these genes had beneficial effects on production of specific fatty acids. In particular, production of palmitic acid particularly benefited from overexpression of GGA2 or INP54, production of palmitoleic acid particularly benefited from overexpression of GGA2 or IDP3, production of oleic acid particularly benefited from overexpression of RTC3, and production of stearic acid particularly benefited from overexpression of INP54 or RTC3.

REFERENCES

David and Siewers, Advances in yeast genome engineering, *FEMS yeast research*, 2015, 15(1): 1-14

Deatherage and Barrick, Identification of mutations in laboratory—evolved microbes from next-generation sequencing data using breseq, *Methods Mo. Biol*, 2014, 1151: 165-188

Gietz and Schiestl, High-efficiency yeast transformation using the LiAc/SS carrier DNA/PEG method, *Nature Protocols*, 2007, 2(1): 31-34

Jenjaroenpun et al., Complete genomic and transcriptional landscape analysis using third-generation sequencing: a case study of *Saccharomyces cerevisiae* CEN.PK113-7D, *Nucleic Acids Res*, 2018, 46: e38

Jessop-Fabre, et al., EasyClone-MarkerFree: A vector toolkit for marker-less integration of genes into *Saccharomyces cerevisiae* via CRISPR-Cas9, *Biotechnol J*, 2016, 11(8): 1110-1117

Langmead and Salzberg, Fast gapped-read alignment with Bowtie 2, *Nat. Methods*, 2012, 9: 357-359

Mans et al., CRISPR/Cas9: a molecular Swiss army knife for simultaneous introduction of multiple genetic modifications in *Saccharomyces cerevisiae*, *FEMS Yeast Res*, 2015, 15(2): pii: fov004

Pfleger et al., Metabolic engineering strategies for microbial synthesis of oleochemicals, *Metabolic Engineering*, 2015, 29: 1-11

Zhang et al., Adaptive mutations in sugar metabolism restore growth on glucose in a pyruvate decarboxylase negative yeast strain, *Microbial cell factories*, 2015, 14: 116

Zhou et al., Modular pathway engineering of diterpenoid synthases and the mevalonic acid pathway for miltiradiene production, *J Am Chem Soc*, 2012, 134(6): 3234-3241

Zhou et al., Production of fatty acid-derived oleochemicals and biofuels by synthetic yeast cell factories, *Nature Communications*, 2016, 7: 11709

The invention claimed is:

1. A yeast cell, wherein
pyruvate decarboxylase activity in said yeast cell is downregulated by the deletion of at least one gene selected from the group consisting of PDC1, PDC5 and PDC6; and
said yeast cell is further genetically modified for
downregulation of an endogenous fructose-1,6-bisphosphate (FBP)-sensitive pyruvate kinase PYK1; and/or
overexpression of an endogenous fructose-1,6-bisphosphate (FBP)-insensitive pyruvate kinase PYK2, wherein
said yeast cell has reduced ethanol formation compared to an unmodified yeast cell by said deletion of at least one gene selected from the group consisting of PDC1, PDC5 and PDC6; and
said yeast cell is able to grow on glucose as a carbon source by said downregulation of said endogenous PYK1 and/or said overexpression of said endogenous PYK2.

2. The yeast cell according to claim 1, wherein said yeast cell is genetically modified for overexpression of an endogenous acetyl-CoA carboxylase.

3. The yeast cell according to claim 1, wherein said yeast cell is genetically modified for overexpression of an endogenous pyruvate carboxylase.

4. The yeast cell according to claim 1, wherein said yeast cell is further genetically modified for overexpression of at least one protein selected from the group consisting of a mitochondrial pyruvate carrier, a citrate synthase and a citrate and oxoglutarate carrier protein.

5. The yeast cell according to claim 4, wherein said mitochondrial pyruvate carrier is selected from the group consisting of MPC1 and MPC3.

6. The yeast cell according to claim 4, wherein said citrate synthase is selected from the group consisting of Rhodosporidium toruloides citrate synthase RtCIT1 and *Saccharomyces cerevisiae* citrate synthase ScCIT1.

7. The yeast cell according to claim 4, wherein said citrate and oxoglutarate carrier protein is YHM2.

8. The yeast cell according to claim 1, wherein said yeast cell is genetically modified for overexpression of a gene selected from the group consisting of MPP6, ACP1, EPT1, FAA1, GEP4, GGA2, IDP3, INP54, LPP1, MCR1, ORMI, RTC3, SPO7, TGL1 and YFT2.

9. The yeast cell according to claim 8, wherein said yeast cell is genetically modified for overexpression of GGA2.

10. The yeast cell according to claim 1, wherein said yeast cell is a yeast cell selected from the group consisting of *Saccharomyces, Kluyveromyces, Zygosaccharomyces, Candida, Hansenula, Torulopsis, Kloeckera, Pichia, Schizosaccharomyces*, Trigonopsis, Brettanomyces, Debaromyces, Nadsonia, Lipomyces, *Cryptococcus, Aureobasidium, Trichosporon, Lipomyces, Rhodotorula, Yarrowia*, Rhodosporidium, Phaffia, *Schwanniomyces, Aspergillus*, and Ashbya.

11. The yeast cell according to claim 10, wherein said yeast cell is a yeast cell selected from the group consisting of *Saccharomyces cerevisiae, Pichia pastoris, Ashbya gossypii, Saccharomyces boulardii, Zygosaccharomyces bailii, Kluyveromyces lactis*, Rhodosporidium toruloides and *Yarrowia lipolytica*.

12. A method for producing a fatty acid comprising:
culturing a yeast cell according to claim 1 in a culture medium and in culture conditions suitable for production of said fatty acid by said yeast cell, and
collecting said fatty acid from said culture medium and/or said yeast cell,
wherein the yeast cell according to claim 1 is genetically modified for overexpression of an endogenous acetyl-CoA carboxylase and genetically modified for overexpression of an endogenous pyruvate carboxylase.

13. A method for producing a fatty acid derived-product comprising:
culturing a yeast cell according claim 1 in a culture medium and in culture conditions suitable for production of said fatty acid-derived product by said yeast cell; and
collecting said fatty acid-derived product from said culture medium and/or said yeast cell,
wherein said fatty acid-derived product is selected from the group consisting of a hydrocarbon, a triacylglyceride, a phospholipid, a lactone, a fatty alcohol, a fatty aldehyde, a fatty acid ester, and a mixture thereof, and
wherein the yeast cell according to claim 1 is genetically modified for overexpression of an endogenous acetyl-CoA carboxylase and genetically modified for overexpression of an endogenous pyruvate carboxylase.

* * * * *

SEQUENCE LISTING

```
Sequence total quantity: 40
SEQ ID NO: 1          moltype = AA  length = 2233
FEATURE               Location/Qualifiers
source                1..2233
                      mol_type = protein
                      organism = Saccharomyces cerevisiae
SEQUENCE: 1
MSEESLFESS PQKMEYEITN YSERHTELPG HFIGLNTVDK LEESPLRDFV KSHGGHTVIS    60
KILIANNGIA AVKEIRSVRK WAYETFGDDR TVQFVAMATP EDLEANAEYI RMADQYIEVP   120
GGTNNNNYAN VDLIVDIAER ADVDAVWAGW GHASENPLLP EKLSQSKRKV IFIGPPGNAM   180
RSLGDKISST IVAQSAKVPC IPWSGTGVDT VHVDEKTGLV SVDDDIYQKG CCTSPEDGLQ   240
KAKRIGFPVM IKASEGGGGK GIRQVEREED FIALYHQAAN EIPGSPIFIM KLAGRARHLE   300
```

```
VQLLADQYGT NISLFGRDCS VQRRHQKIIE EAPVTIAKAE TFHEMEKAAV RLGKLVGYVS  360
AGTVEYLYSH DDGKFYFLEL NPRLQVEHPT TEMVSGVNLP AAQLQIAMGI PMHRISDIRT  420
LYGMNPHSAS EIDFEFKTQD ATKKQRRPIP KGHCTACRIT SEDPNDGFKP SGGTLHELNF  480
RSSSNVWGYF SVGNNGNIHS FSDSQFGHIF AFGENRQASR KHMVVALKEL SIRGDFRTTV  540
EYLIKLLETE DFEDNTITTG WLDDLITHKM TAEKPDPTLA VICGAATKAF LASEEARHKY  600
IESLQKGQVL SKDLLQTMFP VDFIHEGKRY KFTVAKSGND RYTLFINGSK CDIILRQLSD  660
GGLLIAIGGK SHTIYWKEEV AATRLSVDSM TTLLEVENDP TQLRTPSPGK LVKFLVENGE  720
HIIKGQPYAE IEVMKMQMPL VSQENGIVQL LKQPGSTIVA GDIMAIMTLD DPSKVKHALP  780
FEGMLPDFGS PVIEGTKPAY KFKSLVSTLE NILKGYDNQV IMNASLQQLI EVLRNPKLPY  840
SEWKLHISAL HSRLPAKLDE QMEELVARSL RRGAVFPARQ LSKLIDMAVK NPEYNPDKLL  900
GAVVEPLADI AHKYSNGLEA HEHSIFVHPL EEYYEVEKLF NGPNVREENI ILKLRDENPK  960
DLDKVALTVL SHSKVSAKNN LILAILKHYQ PLCKLSSKVS AIFSTPLQHI VELESKATAK 1020
VALQAREILI QGALPSVKER TEQIEHILKS SVVKVAYGSS NPKRSEPDLN ILKDLIDSNY 1080
VVFDVLLQFL THQDPVVTAA AAQVYIRRAY RAYTIGDIRV HEGVTVPIVE WKFQLPSAAF 1140
STFPTVKSKM GMNRAVSVSD LSYVANSQSS PLREGILMAV DHLDDVDEIL SQSLEVIPRH 1200
QSSSNGPAPD RSGSSASLSN VANVCVASTE GFESEEEILV RLREILDLNK QELINASIRR 1260
ITFMFGFKDG SYPKYYTFNG PNYNENETIR HIEPALAFQL ELGRLSNFNI KPIFTDNRNI 1320
HVYEAVSKTS PLDKRFFTRG IIRTGHIRDD ISIQEYLTSE ANRLMSDILD NLEVTDTSNS 1380
DLNHIFINFI AVFDISPEDV EAAFGGFLER FGKRLLRLRV SSAEIRIIIK DPQTGAPVPL 1440
RALINNVSGY VIKTEMYTEV KNAKGEWVFK SLGKPGSMHL RPIATPYPVK EWLQPKRYKA 1500
HLMGTTYVYD FPELFRQASS SQWKNFSADV KLTDDFFISN ELIEDENGEL TEVEREPGAN 1560
AIGMVAFKIT VKTPEYPRGR QFVVVANDIT FKIGSFGPQE DEFFNKVTEY ARKRGIPRIY 1620
LAANSGARIG MAEEIVPLFQ VAWNDAANPD KGFQYLYLTS EGMETLKKFD KENSVLTERT 1680
VINGEERFVI KTIIGSEDGL GVECLRGSGL IAGATSRAYH DIFTITLVTC RSVGIGAYLV 1740
RLGQRAIQVE GQPIILTGAP AINKMLGREV YTSNLQLGGT QIMYNNGVSH LTAVDDLAGV 1800
EKIVEWMSYV PAKRNMPVPI LETKDTWDRP VDFTPTNDET VDVRWMIEGR ETESGFEYGL 1860
FDKGSFFETL SGWAKGVVVG RARLGGIPLG VIGVETRTVE NLIPADPANP NSAETLIQEP 1920
GQVWHPNSAF KTAQAINDFN NGEQLPMMIL ANWRGFSGGQ RDMFNEVLKY GSFIVDALVD 1980
YKQPIIIYIP PTGELRGGSW VVVDPTINAD QMEMYADVNA RAGVLEPQGM VGIKFRREKL 2040
LDTMNRLDDK YRELRSQLSN KSLAPEVHQQ ISKQLADRER ELLPIYGQIS LQFADLHDRS 2100
SRMVAKGVIS KELEWTEARR FFFWRLRRRL NEEYLIKRLS HQVGEASRLE KIARIRSWYP 2160
ASVDHEDDRQ VATWIEENYK TLDDKLKGLK LESFAQDLAK KIRSDHDNAI DGLSEVIKML 2220
STDDKEKLLK TLK                                                    2233

SEQ ID NO: 2           moltype = AA   length = 1178
FEATURE                Location/Qualifiers
source                 1..1178
                       mol_type = protein
                       organism = Saccharomyces cerevisiae
SEQUENCE: 2
MSQRKFAGLR DNFNLLGEKN KILVANRGEI PIRIFRTAHE LSMQTVAIYS HEDRLSTHKQ   60
KADEAYVIGE VGQYTPVGAY LAIDEIISIA QKHQVDFIHP GYGFLSENSE FADKVVKAGI  120
TWIGPPAEVI DSVGDKVSAR NLAAKANVPT VPGTPGPIET VEEALDFVNE YGYPVIIKAA  180
FGGGGRGMRV VREGDDVADA FQRATSEART AFGNGTCFVE RFLDKPKHIE VQLLADNHGN  240
VVHLFERDCS VQRRHQKVVE VAPAKTLPRE VRDAILTDAV KLAKECGYRN AGTAEFLVDN  300
QNRHYFIEIN PRIQVEHTIT EEITGIDIVA AQIQIAAGAS LPQLGLFQDK ITTRGFAIQC  360
RITTEDPAKN FQPDTGRIEV YRSAGGNGVR LDGGANAYAGT IISPHYDSML VKCSCSGSTY  420
EIVRRKMIRA LIEFRIRGVK TNIPFLLTLL TNPVFIEGTG WTTFIDDTPQ LFQMVSSQNR  480
AQKLLHYLAD VAVNGSSIKG QIGLPKLKSN PSVPHLHDAQ GNVINVTKSA PPSGWRQVLL  540
EKGPAEFARQ VRQFNGTLLM DTTWRDAHQS LLATRVRTHD LATIAPTTAH ALAGRFALEC  600
WGGATFDVAM RFLHEDPWER LRKLRSLVPN IPFQMLLRGA NGVAYSSLPD NAIDHFVKGA  660
KDNGVDIFRV FDALNDLEQL KVGVDAVKKA GGVVEATVCF SGDMLQPGKK YNLDYYLEIA  720
EKIVQMGTHI LGIKDMAGTM KPAAAKLLIG SLRAKYPDLP IHVHTHDSAG TAVASMTACA  780
LAGADVVDVA INSMSGLTSQ PSINALLASL EGNIDTGINV EHVRELDAYW AEMRLLYSCF  840
EADLKGPDPE VYQHEIPGGQ LTNLLFQAQQ LGLGEQWAET KRAYREANYL LGDIVKVTPT  900
SKVVGDLAQF MVSNKLTSDD VRRLANSLDF PDSVMDFFEG LIGQPYGGFP EPFRSDVLRN  960
KRRKLTCRPG LELEPPFDLEK IREDLQNRFG DVDECDVASY NMYPRVYEDF QKMRETYGDL 1020
SVLPTRSFLS PLETDEEIEV VIEQGKTLII KLQAVGDLNK KTGEREVYFD LNGEMRKIRV 1080
ADRSQKVETV TKSKADMHDP LHIGAPMAGV IVEVKVHKGS LIKKGQPVAV LSAMKMEMII 1140
SSPSDGQVKE VFVSDGENVD SSDLLVLLED QVPVETKA                         1178

SEQ ID NO: 3           moltype = DNA   length = 1374
FEATURE                Location/Qualifiers
source                 1..1374
                       mol_type = other DNA
                       organism = Synthetic construct
SEQUENCE: 3
atgttctctg ctactagaac tgctgctaga acagcagctc aagctgctaa tagaagaaat   60
gtttccacca tcagagaaac cttgaaagaa atcatcccag aaagacaagc cttgttgaag  120
caaatcaaat ctgaacatgg tgctaagacc ttgggtaatg ttactgttga caagttgtt   180
ggtggtggta gaggtattaa gtttatgttt tgggatccat ccgttttgga tgctaagaa   240
ggtattgat tttggggtag atctatccct gaatgccaaa gagatttgcc aactgctcca  300
ggtggtcaag aaattttgcc agaagctatg tttggtact tgttgactgg taaagttcca  360
accgctgaac aaattaagca attccaagaa gaattgcctt ccagatctga attgccagct  420
catgttgaaa aggttttgga ttcttttgca aagaccttgc atccaatgac ccaatttgtt  480
attggtgttg ctgcttttgaa ccacgattct caatttgctg caagatacaa agctggtatg  540
aagaaagctg aatattggga accagcattg gaagattctt tggattgtgt tgctaagtcc  600
ttcactattg cagctagaat ctacttgcac tcttacaaag atggtgctgc aaatatggct  660
ccagttgata agacaaaaga tttgtctgct aacttcgcca ctcaaatcgg tttggtgat  720
```

```
tctgaaggtt tcgtcgaatt gatcagatta tacaactcct tgcataccga tcatgaaggt  780
ggtaatgttt ctgctcatac cactcatttg gttggttctg ctttgtctga tccattcttg  840
tcttattctg ctgctttagg tggtttggct ggtccattgc atggtttagc taatcaagaa  900
gtcttgagat tcatcttggg tatgcaaaaa gaattgggtg attccccatc tgatgaacaa  960
atcgttcaat atatctggaa aactttgaac tccggtcaag ttattccagg ttatggtcat 1020
gctgttttga gaaaaccaga tcctagattt gctgccttga gagaatttgg taacaaacat 1080
ccagaaaccg ctaacgatcc agttttcaga atggttgatt ccttgtttaa agttgcccca 1140
ggtgttttga cagaacatgg taaaactaag aacccattcc caaatgttga tgctgcttct 1200
ggttcttttgt tgtatcatta cggttttgact caattccctt actacactgt tactttcggt 1260
acttctagag ctattggtgc tttgtcacaa tacgtttggg atagagcttt gggtttgcca 1320
attgaaagac caaagtcttt gtccatggaa gccattttga agttggtcaa gtga         1374

SEQ ID NO: 4              moltype = DNA  length = 3651
FEATURE                   Location/Qualifiers
source                    1..3651
                          mol_type = other DNA
                          organism = Synthetic construct
SEQUENCE: 4
atgctttcac tacgtcaatc tataagattt ttcaagccag ccacaagaac tttgtgtagc   60
tctagatatc tgcttatgtc aggcggaggt ggcatgtcgc aaagaaaatt cgccatgtcg  120
caaagaaaat tcgccggctt gagagataac ttcaatctct gggtgaaaaa gaacaaaata  180
ttggtggcta atagaggaga aattccaatc agaatttttc gtaccgctca tgaactgtct  240
atgcagacgg tagctatata ttctcatgaa gatcgtcttt caacgcacaa acaaaaggct  300
gacgaagcat acgtcatagg tgaagtaggc aatataccc cgtcggcgc ttatttggcc   360
attgacgaaa tcatttccat tgcccaaaaa caccaggtag atttcatcca tccaggttat  420
gggttcttgt ctgaaaattc ggaatttgcc gacaaagtag tgaaggccgg tatcacttgg  480
attggccctc cagctgaagt tattgactcc gtgggtgata aggtctcagc tagaaacctg  540
gcagcaaaag ctaatgtgcc caccgttcct ggtacaccag gtcctataga aactgtagag  600
gaagcacttg acttcgtcaa tgaatacggc tacccggtga tcattaaggc cgccttttggt 660
ggtggtggta gaggtgatgag agtcgttaga gaaggtgaac acgtggcgaa tgcctttcaa  720
cgtgctacct ccgaagcccg tactgccttc ggtaatggta cctgctttgt ggaaagattc  780
ttggacaagc caaagcatat tgaagttcaa ttgttggccg ataaccacgg aaacgtggtt  840
catctttttcg aaagagactg ttccgtgcag agaagcacacc aaaaggttgt cgaagtggcc  900
ccagcaaaga ctttaccccg tgaagtccgt gacgccattt tgacagatgc agttaaattg  960
gccaaagagt gtggctacag aaatgcgggt actgctgaat tcttggttga taaccaaaat 1020
agacactatt tcattgaaat taatccaaga atccaagtgg aacataccat cacagaagaa 1080
attaccggta tagatattgt ggcggctcag atccaaattg cggcaggtgc ctctctaccc 1140
cagctgggcc tattccagga caaaattacg actcgtggct ttgccattca gtgccgtatt 1200
accacggaag accctgctaa gaacttccaa ccagataccg gtagaataga agtgtaccgt 1260
tctgcaggtg gtaatggtgt tagactggat ggtggtaacg cctatgcagg aacaataatc 1320
tcacctcatt acgactcaat gctggtcaaa tgctcatgct ccggttccac ctacgaaatc 1380
gttcgtagaa aaatgattcg tgcattaatc gagttcagaa ttagaggtgt caagaccaac 1440
attcccttcc tattgactct tttgaccaat ccagtattta ttgagggtac atactggacg 1500
acttttattg acgacacccc acaactgttc caaatggttt catcacaaaa cagagcccaa 1560
aaacttttac attacctcgc cgacgtggca gtcaatggtt catctatcaa gggtcaaatt 1620
ggcttgccaa aattaaaatc aaatccaagt gtcccccatt gcacgatgc tcagggcaat 1680
gtcatcaacg ttacaaagtc tgcaccacca tccggatgga ggcaagtgct actagaaaag 1740
gggccagctg aatttgccag acaagttaga cagttcaatg gtactttatt gatggacacc 1800
acctggagag acgctcatca atctctactt gcaacaagag tcagaaccca cgatttggct 1860
acaatcgctc aacaaccgc acatgccctt gcaggtcgtt tcgccttaga atgttggggt 1920
ggtgccacat tcgatgttgc aatgagattt ttgcatgagg atccatggga acgtttggga 1980
aaattaagat ctctggtgcc taatattcca ttccaaatgt tattgcgtgg tgccaatggt 2040
gtggcttatt cttcattgcc tgacaatgct attgaccatt cgtcaagca agccaaggat 2100
aatggtgttg atatatttag agtctttgat gccttaaatg acttgaaaca attgaaggtc 2160
ggtgtagatg ctgtgaagaa ggcaggtggt gttgtagaaa ccactgtttg ttttctcttg 2220
gatatgcttc agccaggcaa gaaatacaat ttggattac acttggaaat tgctgaaaaa 2280
attgtccaaa tggcactca tatcctgggg atcaaagata tggcaggtac catgaagcca 2340
gcagctgcca aactactgat tggatctttg agggctaagt accctgatct cccaatacat 2400
gttcacactc acgattctgc aggtactgtc gttgcatcaa tggctgcgtg tgctctggcg 2460
ggcgccgatg tcgttgatgt tgccatcaac tcaatgtctg gtttaacttc acaaccatca 2520
atcaatgctc tgttggcttc attagaaggt aatattgaca ctggtattaa cgttgagcat 2580
gtccgtgaac tagatgcata ttgggcagag atgagattgt tatactcttg tttcgaggct 2640
gacttgaagg gcccagatcc agaagtttat caacatgaaa tcccaggtgg tcaattgaca 2700
aacttgttgt ttcaagccca acaattgggt cttggagaac atgggccga aacaaaaaga 2760
gcttacagag aagccaatta tttattgggt gatattgtca agttaccccc aacttcgaag 2820
gtcgttggtg atctggcaca atttatggtc tccaataaat taacttccga tgatgtgaga 2880
cgcctggcta attctttgga tttccctgac tctgttatgg atttcttcga aggcttaatc 2940
ggccaaccat atggtgggtt ccagaaccaa tttagatcag acgttttaag gaacaagaga 3000
agaaagttga cttgtcgtcc aggcctggaa ctagagccat ttgatctcga aaaaattaga 3060
gaagacttgc agaatagatt tggtgatgtt gatgagtgcg acgttgcttc ttataacatg 3120
tacccaagag tttatgaaga cttccaaaag atgagagaaa cgtatggtga tttatctgta 3180
ttgccaacaa gaagctttt gtctccacta gagactgacg aagaaattga agttgtaatc 3240
gaacaaggta aaacgctaat tatcaagcta caggctgtgg gtgatttgaa caaaaagacc 3300
ggtgaaagga aagtttactt tgatttgaat ggtgaaatga tttgctgtgac 3360
agatcacaaa aagtggaaac tgttactaaa tccaaagcag acatgcatga tccattcac   3420
attggtgcac caatgcagg tgtcattgtt aagttaaag ttcataaagg atcactaata  3480
aagaagggcc aacctgtagc cgtattaagc gccatgaaaa tggaaatgat tatatcttct 3540
ccatccgatg gacaagttaa agaagtgttt gtctctgatg tgaaaatgt ggactcttct  3600
gatttattag ttctattaga agaccaagtt cctgttgaaa ctaaggcatg a            3651
```

```
SEQ ID NO: 5            moltype = AA  length = 655
FEATURE                 Location/Qualifiers
source                  1..655
                        mol_type = protein
                        organism = Aspergillus nidulans
SEQUENCE: 5
MPAAPLVSTA NGPNANDNIT RFEPPSRVRS PFADALFHNK TRCFVYGMQP RAVQGMLDFD    60
FICKRSTPSV AGIIYTFGGQ FVSKMYWGTS ETLLPVYQDT AKAMAKHPDV DTVVNFASSR   120
SVYSSTMELM QYPQIKCIAI IAEGVPERRA REILVTAKEK GITIIGPATV GGIKPGAFKI   180
GNTGGMMDNI VASKLYRKGS VGYVSKSGGM SNELNNIISQ TTDGVYEGVA IGGDRYPGTT   240
FIDHLLRYQA EPECKILVLL GEVGGVEEYR VIEAVKNGVI TKPIVAWAIG TCASMFKTEV   300
QPGHAGASAN SDLETAVAKN KAMREAGIYV PDTFEDMPAV LKKVYEEQVQ NGVIKPQPEP   360
VPPKIPIDYS WAQELGLIRK PAAFISTISD DRGQELLYAG MPISDVFKED IGIGGVMSLL   420
WFRRRLPSYA TKFLEMVLML TADHGPAVSG AMNTIITTRA GKDLISALVS GLLTIGSRFG   480
GALDGAAEEF TKAFDKGMSP RDFVDTMRKE NKLIPGIGHR IKSRNNPDLR VELVKEYVKK   540
HFPSTKLLDY AIAVETVTTS KKDNLILNVD GCIAVCFVDL MRNCGAFSAE ESEDYMKMGV   600
LNGLFVLGRS IGLIAHYLDQ KRLRTGLYRH PWDDITYLLP ALQKGGSEGR VEVNV        655

SEQ ID NO: 6            moltype = DNA  length = 1287
FEATURE                 Location/Qualifiers
source                  1..1287
                        mol_type = genomic DNA
                        organism = Saccharomyces cerevisiae
SEQUENCE: 6
atgagtatgt tatctagaag attattttcc acctctcgcc ttgctgcttt cagtaagatt    60
aaggtcaaac aacccgttgt cgagttggac ggtgatgaaa tgacccgtat catttgggat   120
aagatcaaga gaaaattgat tctaccctac ttggacgtag atttgaagta ctacgactta   180
tctgtcgaat ctcgtgacgc cacctccgac aagattactc aggatgctgc tgaggcgatc   240
aagaagtatg gtgttggtat caaatgtgcc accatcgctc ctgatgaagc tcgtgtgaag   300
gaattcaacc tgcacaagat gtggaaatct cctaatggta ccatcagaaa cattctcggc   360
ggtacagtgt tcagagagcc cattgtgatt cctagaattc ctagactggt cccacgttgg   420
gaaaaaccaa tcattattgg aagacacgcc acggtgatc aatataaagc tacggacaca   480
ctgatcccag gcccaggatc tttggaactg tctacaagc catccgaccc tacgactgta   540
caaccacaaa ctttgaaagt gtatgactac aagggcagtg gtgtggccat ggccatgtac   600
aatactgacg aatccatcga agggtttgct cattcgtctt tcaagctggc cattgacaaa   660
aagctaaatc ttttcttgtc aaccaagaac actattttga agaaatatga cggtcggttc   720
aaagacattt tccaagaagt ttatgaagct caatataaat ccaaattcga caactaggg   780
atccactatg aacaccgttt aattgatgat atggtcgctc aaatgataaa atctaaaggt   840
ggctttatca tggcgctaaa gaactatgac ggtgatgtcc aatctgacat cgtcgctcaa   900
ggatttggct ccttaggttt gatgacttct atccttagtta caccgacgg taaaactttc   960
gaaagtgaag ctgctcatgg taccgtgaca agacattata gaaagtacca aagggtgaa  1020
gaaacttcta caaactccat tgcatccatt ttcgcgtggt cgagaggtct attgaagaga  1080
ggtgaattgg acaatactcc tgctttgtgt aaatttgcca atattttgga atccgccact  1140
ttgaacacag ttcagcaaga cggtatcatg acgaaggact tggctttggc ttgcggtaac  1200
aacgaaagat ctgcttatgt taccacagaa gaattttgg atgccgttga aaaaagacta  1260
caaaagaaa tcaagtcgat cgagtaa                                     1287

SEQ ID NO: 7            moltype = AA  length = 563
FEATURE                 Location/Qualifiers
source                  1..563
                        mol_type = protein
                        organism = Saccharomyces cerevisiae
SEQUENCE: 7
MSEITLGKYL FERLKQVNVN TVFGLPGDFN LSLLDKIYEV EGMRWAGNAN ELNAAYAADG    60
YARIKGMSCI ITTFGVGELS ALNGIAGSYA EHVGVLHVVG VPSISAQAKQ LLLHHTLGNG   120
DFTVFHRMSA NISETTAMIT DIATAPAEID RCIRTTYVTQ RPVYLGLPAN LVDLNVPAKL   180
LQTPIDMSLK PNDAESEKEV IDTILALVKD AKNPVILADA CCSRHDVKAE TKKLIDLTQF   240
PAFVTPMGKG SIDEQHPRYG GVYVGTLSKP EVKEAVESAD LILSVGALLS DFNTGSFSYS   300
YKTKNIVEFH SDHMKIRNAT FPGVQMKFVL QKLLTTIADA AKGYKPVAVP ARTPANAAVP   360
ASTPLKQEWM WNQLGNFLQE GDVVIAETGT SAFGINQTTF PNNTYGISQV LWGSIGFTTG   420
ATLGAAFAAE EIDPKKRVIL FIGDGSLQLT VQEISTMIRW GLKPYLFVLN NDGYTIEKLI   480
HGPKAQYNEI QGWDHLSLLP TFGAKDYETH RVATTGEWDK LTQDKSFNDN SKIRMIEIML   540
PVFDAPQNLV EQAKLTAATN AKQ                                          563

SEQ ID NO: 8            moltype = AA  length = 563
FEATURE                 Location/Qualifiers
source                  1..563
                        mol_type = protein
                        organism = Saccharomyces cerevisiae
SEQUENCE: 8
MSEITLGKYL FERLSQVNCN TVFGLPGDFN LSLLDKLYEV KGMRWAGNAN ELNAAYAADG    60
YARIKGMSCI ITTFGVGELS ALNGIAGSYA EHVGVLHVVG VPSISSQAKQ LLLHHTLGNG   120
DFTVFHRMSA NISETTAMIT DIANAPAEID RCIRTTYTTQ RPVYLGLPAN LVDLNVPAKL   180
LETPIDLSLK PNDAEAEAEV VRTVVELIKD AKNPVILADA CASRHDVKAE TKKLMDLTQF   240
PVYVTPMGKG AIDEQHPRYG GVYVGTLSRP EVKKAVESAD LILSIGALLS DFNTGSFSYS   300
YKTKNIVEFH SDHIKIRNAT FPGVQMKFAL QKLLDAIPEV VKDYKPVAVP ARVPITKSTP   360
ANTPMKQEWM WNHLGNFLRE GDIVIAETGT SAFGINQTTF PTDVYAIVQV LWGSIGFTVG   420
ALLGATMAAE ELDPKKRVIL FIGDGSLQLT VQEISTMIRW GLKPYIFVLN NNGYTIEKLI   480
```

```
HGPHAEYNEI QGWDHLALLP TFGARNYETH RVATTGEWEK LTQDKDFQDN SKIRMIEVML    540
PVFDAPQNLV KQAQLTAATN AKQ                                           563

SEQ ID NO: 9            moltype = AA  length = 563
FEATURE                 Location/Qualifiers
source                  1..563
                        mol_type = protein
                        organism = Saccharomyces cerevisiae
SEQUENCE: 9
MSEITLGKYL FERLKQVNVN TIFGLPGDFN LSLLDKIYEV DGLRWAGNAN ELNAAYAADG    60
YARIKGLSVL VTTFGVGELS ALNGIAGSYA EHVGVLHVVG VPSISAQAKQ LLLHHTLGNG    120
DFTVPHRMSA NISETTSMIT DIATAPSEID RLIRTTFITQ RPSYLGLPAN LVDLKVPGSL    180
LEKPIDLSLK PNDPEAEKEV IDTVLELIQN SKNPVILSDA CASRHNVKKE TQKLIDLTQF    240
PAFVTPLGKG SIDEQHPRYG GVYVGTLSKQ DVKQAVESAD LILSVGALLS DFNTGSFSYS    300
YKTKNVVEFH SDYVKVKNAT FLGVQMKFAL QNLLKVIPDV VKGYKSVPVP TKTPANKGVP    360
ASTPLKQEWL WNELSKFLQE GDVIISETGT SAFGINQTIF PKDAYGISQV LWGSIGFTTG    420
ATLGAAFAAE EIDPNKRVIL FIGDGSLQLT VQEISTMIRW GLKPYLFVLN NDGYTIEKLI    480
HGPHAEYNEI QTWDHLALLP AFGAKKYENH KIATTGEWDA LTTDSEFQKN SVIRLIELKL    540
PVFDAPESLI KQAQLTAATN AKQ                                           563

SEQ ID NO: 10           moltype = DNA  length = 1077
FEATURE                 Location/Qualifiers
source                  1..1077
                        mol_type = genomic DNA
                        organism = Saccharomyces cerevisiae
SEQUENCE: 10
atgtttgttt caccaccacc agcaacttcg aaaaaccaag ttttacaacg acgtccatta    60
gaatcgacta acagtaatca tgggtttgca agctccctac aggccattcc ggaaaacacg    120
atgagtggca gtgataatgc ttcttttcaa agtttgccac tatcaatgtt ttctgccccc    180
tctactgtgc acacgcaact aactaatgac tcttcgttct ccgaatttcc taaccacaag    240
ttaatcacga gagtgagcct ggatgaagca ttcccaaaaa cgttttatga catgtattcg    300
ccagatattc tattagcaga cccatccaac attctctgta acgggcgtcc caagtttacc    360
aagagagagt tattggattg ggatttaaac gatataagat cgttattgat agtcgagaag    420
ttaaggcccg aatggggtaa tcaactaccg gaagtaataa cggtgggtga taatatgccc    480
cagtttaggt tacaattatt accactatat tctagcgatg agaccataat cgcaacgtta    540
gtccattcgg atctgtacat ggaggctaac ttagattatg aattcaaact aaccagcgcc    600
aaatatacag tagcgaccgc tagaaaaaga catgagcata taactggtag aaatgaagcc    660
gtcatgaatt tgtcgaaacc ggaatggaga atatcatcg aaaattacct cttaaatata    720
gcagtagagg cacaatgcag gtttgatttc aaacaaagat gctccgaata taagaaatgg    780
aagttacaac agtccaactt aaaaagaccg gacatgcccc caccaagcat aataccgcgg    840
aaaaacagca cagaaacaaa atcgcttctg aaaaaggctt tattgaagaa cattcagttg    900
aaaaacccca ataataacct tgatgaattg atgatgagat caagcgccgc aacaaatcaa    960
cagggaaaaa acaaagtcag cttatctaaa gaagaaaagg ctacgatatg gtcgcaatgt    1020
caggcacaag tttaccaaag attaggattg gattggcagc cggattcagt atcctga       1077

SEQ ID NO: 11           moltype = AA  length = 500
FEATURE                 Location/Qualifiers
source                  1..500
                        mol_type = protein
                        organism = Saccharomyces cerevisiae
SEQUENCE: 11
MSRLERLTSL NVVAGSDLRR TSIIGTIGPK TNNPETLVAL RKAGLNIVRM NFSHGSYEYH    60
KSVIDNARKS EELYPGRPLA IALDTKGPEI RTGTTTNDVD YPIPPNHEMI FTTDDKYAKA    120
CDDKIMYVDY KNITKVISAG RIIYVDDGVL SFQVLEVVDD KTLKVKALNA GKICSHKGVN    180
LPGTDVDLPA LSEKDKEDLR FGVKNGVHMV FASFIRTAND VLTIREVLGE QGKDVKIIVK    240
IENQQGVNNF DEILKVTDGV MVARGDLGIE IPAPEVLAVQ KKLIAKSNLA GKPVICATQM    300
LESMTYNPRP TRAEVSDVGN AILDGADCVM LSGETAKGNY PINAVTTMAE TAVIAEQAIA    360
YLPNYDDMRN CTPKPTSTTE TVAASAVAAV FEQKAKAIIV LSTSGTTPRL VSKYRPNCPI    420
ILVTRCPRAA RFSHLYRGVF PFVFEKEPVS DWTDDVEARI NFGIEKAKEF GILKKGDTYV    480
SIQGFKAGAG HSNTLQVSTV                                               500

SEQ ID NO: 12           moltype = AA  length = 506
FEATURE                 Location/Qualifiers
source                  1..506
                        mol_type = protein
                        organism = Saccharomyces cerevisiae
SEQUENCE: 12
MPESRLQRLA NLKIGTPQQL RRTSIIGTIG PKTNSCEAIT ALRKAGLNII RLNFSHGSYE    60
FHQSVIENAV KSEQQFPGRP LAIALDTKGP EIRTGRTLND QDLYIPVDHQ MIFTTDASFA    120
NTSNDKIMYI DYANLTKVIV PGRFIYVDDG ILSFKVLQII DESNLRVQAV NSGYIASHKG    180
VNLPNTDVDL PPLSAKDMKD LQFGVRNGIH IVFASFIRTS EDVLSIRKAL GSEGQDIKII    240
SKIENQQGLD NFDEILEVTD GVMIARGDLG IEILAPEVLA IQKKLIAKCN LAGKPVICAT    300
QMLDSMTHNP RPTRAEVSDV GNAVLDGADC VMLSGETAKG DYPVNAVMIN AATALIAEST    360
IAHLALYDDL RDATPKPTST TETVAAAATA AILEQDGKAI VVLSTTGNTA RLLSKYRPSC    420
PIILVTRHAR TARIAHLYRG VFPFLYEPKR LDDWGEDVHR RLKFGVEMAR SFGMVDNGDT    480
VVSIQGFKGG VGHSNTLRIS TVGQEF                                        506

SEQ ID NO: 13           moltype = AA  length = 585
FEATURE                 Location/Qualifiers
```

| source | 1..585 |
| --- | --- |
| | mol_type = protein |
| | organism = Saccharomyces cerevisiae |

SEQUENCE: 13

```
MSHPHSHSIY LSELPVRKPQ ALGNPLLRKI QRACRMSLAE PDLALNLDIA DYINEKQGAA    60
PRDAAIALAK LINNRESHVA IFALSLLDVL VKNCGYPFHL QISRKEFLNE LVKRFPGHPP   120
LRYSKIQRLI LTAIEEWYQT ICKHSSYKND MGYIRDMHRL LKYKGYAFPK ISESDLAVLK   180
PSNQLKTASE IQKEQEIAQA AKLEELIRRG KPEDLREANK LMKIMAGFKE DNAVQAKQAI   240
SSELNKLKRK ADLLNEMLES PDSQNWDNET TQELHSSALKV AQPKFQKIIE EEQEDDALVQ   300
DLLKFNDTVN QLLEKFNLLK NGDSNAASQI HPSHVSAPLQ QSSGALTNEI NLIDFNDLDE   360
APSQGNNNTN GTGTPAAAET SVNDLLGDLT DLSISNPSTA NQASFGLGGD IVLGSSQPAP   420
PVTTTNNSNN TLDLLGLSTP QSPTNSQAVN SSGFDLLMGF NPTTGTTTAP ARTLVNQSPN   480
LKIEFEISRE SNSVIRIKSF FTNLSSSPIS NLVFLLAVPK SMSLKLQPQS SNFMIGNAKD   540
GISQEGTIEN APANPSKALK VKWKVNYSVN STQAEETAVF TLPNV                  585
```

| SEQ ID NO: 14 | moltype = AA length = 369 |
| --- | --- |
| FEATURE | Location/Qualifiers |
| source | 1..369 |
| | mol_type = protein |
| | organism = Saccharomyces cerevisiae |

SEQUENCE: 14

```
MLRNTFFRNT SRRFLATVKQ PSIGRYTGKP NPSTGKYTVS FIEGDGIGPE ISKSVKKIFS    60
AANVPIEWES CDVSPIFVNG LTTIPDPAVQ SITKNLVALK GPLATPIGKG HRSLNLTLRK   120
TFGLFANVRP AKSIEGFKTT YENVDLVLIR ENTEGEYSGI EHIVCPGVVQ SIKLITRDAS   180
ERVIRYAFEY ARAIGRPRVI VVHKSTIQRL ADGLFVNVAK ELSKEYPDLT LETELIDNSV   240
LKVVTNPSAY TDAVSVCPNL YGDILSDLNS GLSAGSLGLT PSANIGHKIS IFEAVHGSAP   300
DIAGQDKANP TALLLSSVMM LNHMGLTNHA DQIQNAVLST IASGPENRTG DLAGTATTSS   360
FTEAVIKRL                                                          369
```

| SEQ ID NO: 15 | moltype = DNA length = 904 |
| --- | --- |
| FEATURE | Location/Qualifiers |
| source | 1..904 |
| | mol_type = genomic DNA |
| | organism = Saccharomyces cerevisiae |

SEQUENCE: 15

```
aacctagatt gctatctcca ctccctatgc ttgctttggt ggactattgt ttccgttatt    60
cgcaatttct ataggactac tatagattat ataaactgaa ttttagcttt atgctgtggt   120
gttatttccc aaaacacgct cttctttctt acgctttccg ttagcttatt tgctcacggt   180
atcaagatta cttttttttt ttcttctctt tcttttttct gcactacect cttcttcttg   240
ttcttccttg cgttttacc cctcttccct ttatttgca gcaaaagaa agatggaaag   300
gcaaagtga aggcatgatg atgacaaact tgaaaagaaa gagaacagcg aaaagagatg   360
aataatccta ggcaatgact gcacgctcat gggtatcaat tggctaggtc taatattgtt   420
attgtttgga gtatggcgta gagaagtggt tccttaacct taattaatgc ccgtgccatg   480
atgattgcat cactgagacg taatgtgaaa acaccactttc tcggtccgcg gacatcaacc   540
gaaggaaaaa tgacaagcta tttccgtgta tatccgcgcc aatcccttcg gggccgaagt   600
tcggaggctt tatctccgct tagccaaggc cgtcaaaggc gataaggtgc gttgcacccc   660
aattagccat ggagaaggaa aaaaaaagca tgtatgatca aaaattgaga   720
ggaaaaatga ctcaggctat ttatataagt aaatgaaagg gtttcgttgt agccttttct   780
gctctcttcc ttcgctcttc cgcatatata tttgtgttca gagattattc ttaaatccat   840
aagaacatcc cttcatataa caattgaata aggaaaacac aacacataac acatatttaa   900
cctg                                                               904
```

| SEQ ID NO: 16 | moltype = DNA length = 999 |
| --- | --- |
| FEATURE | Location/Qualifiers |
| source | 1..999 |
| | mol_type = genomic DNA |
| | organism = Saccharomyces cerevisiae |

SEQUENCE: 16

```
tttgtcgccc ttgagtaaaa gaaagcgaca aggtgtgcaa ttgttatgag taggattcag    60
ttataattat cacttagcat ttgttctaaa catgaacaca caacgaatgc ctgtaaacac   120
gcttgccgcg ctagacatgc aaacgatcct caaaaaaaaa aaaacgctcg tatgaagacc   180
taatttacgt atttttttt ttttgttttt cgtttacgcg ttaattgatc gattatgagc   240
ttttggggaa aagtaattgc cgcagcggct gtcgtaccgg aagagtgttg ttttttcatta   300
ccaaaaaggg ataattagtgg ttcctttatg tgacattgat aagctgattg ggcataatta   360
cttgcctgat gacgaataac gcgagaactg cccatataga atctgacgac gtaaggagaa   420
gaaaaagcgg gaaacggatt tctcgttcta ggcctcggcg gctcttaaaa ttgtaaaatg   480
aaaatgagaa taaattaaa ctatacacag ctgatcagcg ttcaatgaa aaaaaaatgc   540
attggaagga aaagccgaaa tacttcattt tctgggcatt gacgttctgt tgcctcttgt   600
gcatacacac ttgttttat tgaaatcgag cttattgtaa gagaacttgc gcttatcttc   660
aaatgccgct ttcctcgaaa aagcatttaa acatcattca agattattag tctatcaagc   720
ttgtccgac tgcttgttat tatgtaaaac aagtatgttg gtattgtatt tgattgccga   780
ttctcatatc gccatacacg aaccaattat gcatcataaa aaagcgtag ttctttacc   840
cgaccaacca acttcttcct ttgtcctcaa tatcaaagaa aaaaaaaaa acccactgct   900
cagatgttat aaggaagggg tgttaactta tatacaggtt catctaccag tcaccagtcc   960
atacaaactt gaaccgtctg cgtaccagtc ctaatcaaa                          999
```

| SEQ ID NO: 17 | moltype = DNA length = 457 |
| --- | --- |
| FEATURE | Location/Qualifiers |
| source | 1..457 |

```
                        mol_type = genomic DNA
                        organism = Saccharomyces cerevisiae
SEQUENCE: 17
gcttctcatt ctattttaat tatactagta cgatttctca ctctgtaatt taatatcagt    60
gtaatatgca cctagttatg ggtagttttt gctaacgtta cgagccgcga aactgtcctc   120
aatcttcacc actacctcta atgactgaag aatgctatgc gatataacgc tgtcgcactt   180
tgaatatata cttatattta catagttttc aagtgcgtat tactattgca aagtagtatt   240
ttgtcacgtg attttgatcc aattaaaact aaatatggtt caacccgttg tttccgcatc   300
aaaaaaccat accatttatc aaggggacgg gatatatcac ataacagttt gaatgcataa   360
tttgttatag atatcttctg gaataatctt cacagcaaaa gcgcaagtcg aataatatat   420
cgataaatac aatccataag acttaaaact aacctca                            457

SEQ ID NO: 18           moltype = DNA   length = 438
FEATURE                 Location/Qualifiers
source                  1..438
                        mol_type = genomic DNA
                        organism = Saccharomyces cerevisiae
SEQUENCE: 18
gctgggcgat cttccttgtg cgtctgttgt ctcacaattg cttgaaggaa gatttcataa    60
gatcatatga gtccctcttt atatgggcaa gtggaattat gtgagtcaaa atccgcgcgt   120
gacccgtaaa gcgttatcag aaggtgcaaa cggtgctatt tagctcataa aaggaatgat   180
tcaagctctt ttggattgta agacaccttt atttagtcca agatcattgc agaccccttgt   240
tatggtcttt agcagagtcc tcctctatat ctcttcattt actgcaacct gattggcccg   300
ctaccacgat gcccgctttg ttcctgtggt attaaaagaa tcgatgaaag agactcttat   360
cttcaggaa aattaggacc gagaattaga gcaagcaaga tatttgcaaa ctactaacta    420
caagcgactt acacagac                                                 438

SEQ ID NO: 19           moltype = DNA   length = 546
FEATURE                 Location/Qualifiers
source                  1..546
                        mol_type = genomic DNA
                        organism = Saccharomyces cerevisiae
SEQUENCE: 19
tcattctacc atctttcatg tccctacgcc attctcgttc gtataccata taaaccaatt    60
atagatttta catagaataa tagttaaatt tgattataga atatcttcgg attcaataaa   120
aaattattat tatcagactc tttctgtcca ctccttgaag tatgcaaagt gcttcgagaa   180
cgccatgaca ttcgacaatt caaaattgag agaggactgc taaggaaact ctttgagttg   240
attatataat cgctatttaa tcttttaaag ggggaatact gctaaatttt cattattgta   300
caactggaaa catgatagg ctgaaatgtg ccaccaaatt gcatgacctt gctaatgagg    360
tcgctgggtt gcgtatgcac ttttttaccct gctccgcgtc gaaacagaac ataatacaga   420
gtaaagagga aagagcgaaa atgaaaaagt ttctacactc aaaagtcaaa ccttttttaaa   480
aagtgatgtt cagattcctt gtttaagaca aataccattg aggaaggcga ttgaccctaa   540
cgaagt                                                              546

SEQ ID NO: 20           moltype = DNA   length = 1000
FEATURE                 Location/Qualifiers
source                  1..1000
                        mol_type = genomic DNA
                        organism = Saccharomyces cerevisiae
SEQUENCE: 20
ggccacaatg aaacttcaat tcatatcgac cgactatttt tctccgaacc aaaaaaatag    60
cagggcgaga ttgagctgc ggaaaaaaga ggaaaaaatt ttttcgtagt tttcttgtgc    120
aaattagggt gtaaggtttc tagggcttat tggttcaagc agaagagaca acaattgtag   180
gtcctaaatt caaggcggat gtaaggagta ttggtttcga agttttttcc gaagcggcat   240
ggcagggact acttgcgcat gcgctcggat tatcttcatt tttgcttgca aaaacgtaga   300
atcatggtaa attacatgaa gaattctctt tttttttttt ttttttttttt ttttaccctct   360
aaagagtgtt gaccaactga aaaaacccctt cttcaagaga gttaaactaa gactaaccat   420
cataacttcc aaggaattaa tcgatatctt gcactcctga ttttttcttca aagagacagc   480
gcaaaggatt atgacagtgt tgcattgagt caaaagtttt tccgaagtga cccagtgctc   540
ttttttttttt ccgtgaagga ctgacaaata tgcgcacaag atccaatacg taatggaaat   600
tcggaaaaac taggaagaaa tgctgcaggg cattgccgtg ccgatctttt gtctttcaga   660
tatatgagaa aaagaatatt catcaagtgc tgatagaaga ataccactca tatgacgtgg   720
gcagaagaca gcaaacgtaa acatgagctg ctgcgacatt tgatggcttt tatccgacaa   780
gccaggaaac tccaccatta tctaatgtag caaaatattt cttaacaccc gaagttgcgt   840
gtcccctca cgttttaat catttgaatt agtatattga aattatatat aaaggcaaca    900
atgtccccat aatcaattcc atctggggtc tcatgttctt tccccacctt aaaatctata   960
aagatatcat aatcgtcaac tagttgatat acgtaaaatc                        1000

SEQ ID NO: 21           moltype = DNA   length = 455
FEATURE                 Location/Qualifiers
source                  1..455
                        mol_type = genomic DNA
                        organism = Saccharomyces cerevisiae
SEQUENCE: 21
cgttcccaaa ccattacatt atgttctttc acttattaca tacgatatat agcatctaca    60
tctacatatc taaatgatgt ttttttccat ctactttgtc cgatacgcat taaaagaaga   120
agatttactc tcccgtgatg ccgggccaat cagacgcgcg cattcgcggc agaataaggg   180
gaggctgctg cgggtaccaa atatccagat attcacaatt atgccaatca actgtctagt   240
tgctgacacc catcgttttc cactgcaacg aggttttggg gctagaaaag gcgttaacaa   300
```

```
tcgttagaga aggagggggtt cataacttga cttgttgtat cttgtttaaa acttctcttg    360
aatttgttcg tggttgaatt tgttttgct atcccaaagg agtgcatttt acacgcatta     420
ctacagcaca cttttataca gttccacaat agaat                                455

SEQ ID NO: 22           moltype = DNA   length = 424
FEATURE                 Location/Qualifiers
source                  1..424
                        mol_type = genomic DNA
                        organism = Saccharomyces cerevisiae
SEQUENCE: 22
atagataaaa aaaaaacgca ccaagtaagt aagtaaataa agaataaata aactatatga    60
gtaaaacacc aagcgaggat gtttcattgt gcatccgtgt tcttgatgat cacataactg    120
taaagaata atacggcacg ttaaatgtta ttttagaata tataaacacc ttatgtgcca     180
taagcattga gccaatcgct gctgtttttt ttattccgag gcaccttcgg aagaacacag   240
gcgcaattta gttatataag gagaagcccc cgagcgatca ggggaccgac tgcggatcgc    300
tttaaggcaa agatagaagg ataaatatct gctttggaag atagtcgtat ctaatttccc   360
attctgttgt tttcttgatc tttcctacgc ttcgactttt cttcctacgc gctttataat   420
agct                                                                 424

SEQ ID NO: 23           moltype = DNA   length = 812
FEATURE                 Location/Qualifiers
source                  1..812
                        mol_type = genomic DNA
                        organism = Saccharomyces cerevisiae
SEQUENCE: 23
cttttttgc tctatatta ttggtaacag tgcttattgt tactcaatgt atggtacgct      60
gcatacctat caagatgcga ctacatatat acaattatct catctcatcg cgtattgaaa    120
aatttttccat cttctaattt ttcagaaccc ataaattcgg gtaacgatca gtggaaaaaa  180
cttaaatccg cagtaatagg cttgcaaagg accaaagaca gcatatgcag cagttaagaa   240
atctaagaat gcattgtata ttagatagt atatggaaaa gctcggactg ggagccgtaa    300
aatctctttc ccgtaagatc tggctgcaaa cctggtctac ataaatgtag tacattataa   360
gggactacca agaaatacga agcgctcaga tatctcttaa agttcatttt tttgccggaa   420
taatcttggt ttagtaactt ataaaactac ttacgtccaa taaatcgtta tatttatgc    480
cgtcgtcata aagtggacac tttgagaga cggtgctggc cataagatg ctgatatttg     540
aaatatcatt tacccgggcc cgggtgggaa aaacaaggaa ttaaagataa tgaagtgatc   600
ttttggcgag atagtaaaac tttcaattat ctaggaacaa tttcaaacgc caattgttaa   660
ctttgtgtac agtatttcta gttttatct cattgaaaac aaaattcagt caacttgaa     720
atttaagcag gctactgtgg cattgagata ttttccgca gagtaagaac cgattagcaa    780
gttaccgcat tatttttaaa ccgtggacaa tc                                  812

SEQ ID NO: 24           moltype = DNA   length = 1000
FEATURE                 Location/Qualifiers
source                  1..1000
                        mol_type = genomic DNA
                        organism = Saccharomyces cerevisiae
SEQUENCE: 24
tttgatggaa gacgagggta atgaagaata caccaaagat ttggaagaag cagctaacaa    60
agctcaacca cagtagaatg gaatattgaa actggagtga cttctgatga agttccaat    120
tatttatatg tatacattat ttatttgtct atcattaaaa tttctgtcaa gtaatggctt   180
tttatgttta tttcatggat tacgaaattt gctggctttt tagagtgacc gatgagttgc   240
atgtacatat gtgcgaaata aaacaatacg gtagtaaaac gtaatactt cgagaagtaa    300
attcaagatt gcaggcgtag cacaagaatg tccttccgcc tgctagtgtg ttgagcaaag  360
cacgccatca ctaatggaac cctacaaaa tctcgcatgg agcagcaaac cttaaatcca    420
ttttctatca ttcgttcctg aggacccgga tatcgtttta gagacaaaaa tagatactac   480
aagaggaata gggatatctg cacatggggc ctcgagcatg gctcattttc gattttccgg  540
cacgatgctg acttagtact atcatgccag gcaggacagg ccttatgggg ttcttgcagc   600
ttaccaattc tgcacactgga ctgccctg attagcgacc ccgcgacccc gcgaccagac   660
tccctgaaaa tggtaattgg tgatgatata tgtgactgag ttcagcctgg gcatacaatg  720
tttaacccttt ttggacatgg aattaggcca gcaaagggag cagcttttcc cgaaagcgta 780
gttttttctcc aggaacgcaa ttcacccctt tcttcttat gcaagctcct cgtacatata  840
taaaaatata tgagtatata tagtgcttct acagcataat caatttaagg ttccttgcct  900
ttcctttaaat atgttagcta tctctaaagc atcactgaga agtggtagtt tttttgataa 960
ctgtgattga agttttgact acctcagaga aaaatttga                         1000

SEQ ID NO: 25           moltype = DNA   length = 1000
FEATURE                 Location/Qualifiers
source                  1..1000
                        mol_type = genomic DNA
                        organism = Saccharomyces cerevisiae
SEQUENCE: 25
aagatctgtt acgtagtatt tgagagaagg agtaaactaa ccttgaattg aggtcttgat    60
tacaagttgc ttgcttagtg acacatttga caagaaaaaa cagtaatacg ccagaacatt   120
tgcggccccct ttttatatca aaagtgctaa acatgctatt taagtatttc ttttgctgtt  180
gatacgcaat tttcattgcg ctgctgcaga tgtggtaccc tttaccgcac aaaaatactt   240
ctatctggat attattccgt gtacttggcg aagaagccat cccgttttga acgccattgc   300
cgctaacctc cgcgctttcg cttgcagcaa tggctacatc cgcacggttc cgctattgcc  360
acgacattgt ggtggtaata gccaaggcaa tggtgtgtac aacttacgat ccctctgctt   420
gcggaagcag tcaaaaggca agtgagatct actctataaa ctgacacttt atccaggaa   480
ttatcgagaa aattctgtct tgtcaattag agaagtaagg ggccacaggg aaataatact   540
```

```
ttcgaaggga gtttctttcc ttaaggaggt gcaaaatgca aaagatatac agtttatagg    600
ttgatacaca tagagcaagt ggtctcaagt ggtcttaatg agtcacggga ggtcaagatg    660
ctcttttttt cttcatcgtt tcagttttgt atcttgagcg gagtgaactt gcccttttaag   720
cgggccatac cctacatgg cgttagcact tattttcaag gtgaatatat acaatgtcag     780
ttacccgttt ttttgtcttc cgctgtataa gcttgctatc attaaaagcc gcatgtggca    840
tcctgaattc tgccacccct taaatacaaa aaatagtgta aatggtactt gatctcttct    900
ggaggaataa acaataattc ttgatggaat ttgagagaaa gtaagtgttc ggctaagcac    960
aataaagata taaacctgtg actacctata aagttcgta                          1000
```

```
SEQ ID NO: 26          moltype = DNA  length = 278
FEATURE                Location/Qualifiers
source                 1..278
                       mol_type = genomic DNA
                       organism = Saccharomyces cerevisiae
SEQUENCE: 26
ttccaatatt agatgcctgt gaaactactg tcaaacttat ttgtgtaaca atactcatcg     60
tctaatttgt ccattattgt tatatactct gtcataaaaa aagaaagaaa aatcttatac    120
tttcgtcgac tgtgatttga aaatctctcg agatcataac ggaataaaag ggtttatatc    180
cgaaggtggc cagaacaatc atgaagcaaa taggataaaa atagccaata agatgtttgt    240
tgtctttcat cccaaagttc caacagcata tttcaaag                            278
```

```
SEQ ID NO: 27          moltype = AA  length = 186
FEATURE                Location/Qualifiers
source                 1..186
                       mol_type = protein
                       organism = Saccharomyces cerevisiae
SEQUENCE: 27
MSANNGVTGK LSSRVMNMKF MKFGKTDDEE SSNSNTPSNI NSDVEPIEQK GKLFGLDDSA     60
WDLNSYKDDL KKISGKEKKK VKRVVYKKRP NLIISNVGYS ELRKPEGVIS GRKTFGDNSD    120
DSGSRKRKFD EGEQNEDEKR DAKDKEFTGS QDDGEDEYDL DKLFKDSIKK KKTNHNGKNK    180
NRNSKK                                                               186
```

```
SEQ ID NO: 28          moltype = AA  length = 125
FEATURE                Location/Qualifiers
source                 1..125
                       mol_type = protein
                       organism = Saccharomyces cerevisiae
SEQUENCE: 28
MFRSVCRISS RVAPSAYRTI MGRSVMSNTI LAQRFYSANL SKDQVSQRVI DVIKAFDKNS     60
PNIANKQISS DTQFHKDLGL DSLDTVELLV AIEEEFDIEI PDKVADELRS VGETVDYIAS    120
NPDAN                                                                125
```

```
SEQ ID NO: 29          moltype = AA  length = 391
FEATURE                Location/Qualifiers
source                 1..391
                       mol_type = protein
                       organism = Saccharomyces cerevisiae
SEQUENCE: 29
MGYFVPDSHI ENLKSYKYQS EDRSLVSKYF LKPFWQRFCH IFPTWMAPNI ITLSGFAFIV     60
INVLTVFYYD PNLNTDTPRW TYFSYALGVF LYQTFDGCDG VHARRINQSG PLGELFDHSI    120
DAINSTLSIF IFASETGMGF SYNLMLSQFA MLTNFYLSTW EEYHTHTLYL SEFSGPVEGI    180
LIVCVSLILT GIYGKQVIWH TYLFTITVGD KVIDVTLDI VFSLAVFGLV MNALSAKRNV     240
DKYYRNSTSS ANNITQIEQD SAIKGLLPFF AYYASIALLV WMQPSFITLS FILSVGFTGA    300
FTVGRIIVCH LTKQSFPMFN APMLIPLCQI VLYKICLSLW GIESNKIVFA LSWLGFGLSL    360
GVHIMFMNDI IHEFTEYLDV YALSIKRSKL T                                   391
```

```
SEQ ID NO: 30          moltype = AA  length = 700
FEATURE                Location/Qualifiers
source                 1..700
                       mol_type = protein
                       organism = Saccharomyces cerevisiae
SEQUENCE: 30
MVAQYTVPVG KAANEHETAP RRNYQCREKP LVRPPNTKCS TVYEFVLECF QKNKNSNAMG     60
WRDVKEIHEE SKSVMKKVDG KETSVEKKWM YYELSHYHYN SFDQLTDIMH EIGRGLVKIG    120
LKPNDDDKLH LYAATSHKWM KMFLGAQSQG IPVVTAYDTL GEKGLIHSLV QTGSKAIFTD    180
NSLLPSLIKP VQAAQDVKYI IHFDSISSED RRQSGKIYQS AHDAINRIKE VRPDIKTFSF    240
DDILKLGKES CNEIDVHPPG KDDLCCIMYT SGSTGEPKGV VLKHSNVVAG VGGASLNVLK    300
FVGNTDRVIC FLPLAHIFEL VFELLSFYWG ACIGYATVKT LTSSSVRNCQ GDLQEFKPTI    360
MVGVAAVWET VRKGILNQID NLPFLTKKIF WTAYNTKLNM QRLHIPGGGA LGNLVFKKIR    420
TATGGQLRYL LNGGSPISRD AQEFITNLIC PMLIGYGLTE TCASTTILDP ANFELGVAGD    480
LTGCVTVKLV DVEELGYFAK NNQGEVWITG ANVTPEYYKN EEETSQALTS DGWFKTGDIG    540
EWEANGHLKI IDRKKNLVKT MNGEYIALEK LESVYRSNEY VANICVYADQ SKTKPVGIIV    600
PNHAPLTKLA KKLGIMEQKD SSINIENYLE DAKLIKAVYS DLLKTGKDQG LVGIELLAGI    660
VFFDGEWTPQ NGFVTSAQKL KRKDILNAVK DKVDAVYSSS                          700
```

```
SEQ ID NO: 31          moltype = AA  length = 185
FEATURE                Location/Qualifiers
source                 1..185
                       mol_type = protein
```

```
                       organism = Saccharomyces cerevisiae
SEQUENCE: 31
MNISGTLNTL RLLYNPSLCK PSLVVPTFND LPIPIHDSIK AVVLDKDNCI AFPHDDKIWP    60
DYLQHWETLR SKYSNKALLI VSNTAGSNSD KDYSQAKLLE DKTGIPVLRH STKKPGCHNE   120
ILDYFYRNKT ITNPKEVAVV GDRLFTDILM ANLMGSYGVW IRDGVKVSAN PLSKFEKKLY   180
NFLGF                                                               185

SEQ ID NO: 32          moltype = AA  length = 420
FEATURE                Location/Qualifiers
source                 1..420
                       mol_type = protein
                       organism = Saccharomyces cerevisiae
SEQUENCE: 32
MSKIKVVHPI VEMDGDEQTR VIWKLIKEKL ILPYLDVDLK YDLSIQERD RTNDQVTKDS    60
SYATLKYGVA VKCATITPDE ARMKEFNLKE MWKSPNGTIR NILGGTVFRE PIIIPKIPRL   120
VPHWEKPIII GRHAFGDQYR ATDIKIKKAG KLRLQFSSDD GKENIDLKVY EFPKSGGIAM   180
AMFNTNDSIK GFAKASFELA LKRKLPLFFT TKNTILKNYD NQFKQIFDNL FDKEYKEKFQ   240
ALKITYEHRL IDDMVAQMLK SKGGFIIAMK NYDGDVQSDI VAQGFGSLGL MTSILITPDG   300
KTFESEAAHG TVTRHFRKHQ RGEETSTNSI ASIFAWTRAI IQRGKLDNTD DVIKFGNLLE   360
KATLDTVQVG GKMTKDLALM LGKTNRSSYV TTEEFIDEVA KRLQNMMLSS NEDKKGMCKL   420

SEQ ID NO: 33          moltype = AA  length = 384
FEATURE                Location/Qualifiers
source                 1..384
                       mol_type = protein
                       organism = Saccharomyces cerevisiae
SEQUENCE: 33
MNKTNWKVSV TTFNCGKEFP VENSKAIVKQ LLFPYDDGIS QLELQDLYVL GFQEVVPIWQ    60
GSFPAVNRDL IDRITTTAVN CLNEKVSATQ GDEQYSCLGV NSLGAITIIV LYNNNALKVK   120
DDILKRNGKC GWFGTHLKGG TLISPQMTRN GEENWERFSY ICAHLNANEG VNNRNQRIDD   180
YKRIMSEVCD SEVAKSDHFF FLGDLNFRVT STYDPTTNYS STTTLRRLLE NHEELNLLRK   240
GEDEPLCKGF QELKITFPPT YKFKLFEKET YNTKRIPSWC DRILYKSYAV PTFAQEGTYH   300
SVPRSNALLF SDHQPVNLTV RLPRSTGTPV PLSLHIEKYP LSWSSGLIGQ IGDAVIGYCG   360
WLVTKNVHYW ILGSLLLYLL LKIL                                          384

SEQ ID NO: 34          moltype = AA  length = 274
FEATURE                Location/Qualifiers
source                 1..274
                       mol_type = protein
                       organism = Saccharomyces cerevisiae
SEQUENCE: 34
MISVMADEKH KEYFKLYYFQ YMIIGLCTIL FLYSEISLVP RGQNIEFSLD DPSISKRYVP    60
NELVGPLECL ILSVGLSNMV VFWTCMFDKD LLKKNRVKRL RERPDGISND FHFMHTSILC   120
LMLIISINAA LTGALKLIIG NLRPDFVDRC IPDLQKMSDS DSLVFGLDIC KQTNKWILYE   180
GLKSTPSGHS SFIVSTMGFT YLWQRVFTTR NTRSCIWCPL LALVVMVSRV IDHRHHWYDV   240
VSGAVLAFLV IYCCWKWTFT NLAKRDILPS PVSV                               274

SEQ ID NO: 35          moltype = AA  length = 302
FEATURE                Location/Qualifiers
source                 1..302
                       mol_type = protein
                       organism = Saccharomyces cerevisiae
SEQUENCE: 35
MFSRLSRSHS KALPIALGTV AIAAATAFYF ANRNQHSFVF NESNKVFKGD DKWIDLPISK    60
IEEESHDTRR FTFKLPTEDS EMGLVLASAL FAKFVTPKGS NVVRPYTPVS DLSQKGHFQL   120
VVKHYEGGKM TSHLFGLKPN DTVSFKGPIM KWKWQPNQFK SITLLGAGTG INPLYQLAHH   180
IVENPNDKTK VNLLYGNKTP QDILLRKELD ALKEKYPDKF NVTYFVDDKQ DDQDFDGEIS   240
FISKDFIQEH VPGPKESTHL FVCGPPPFMN AYSGEKKSPK DQGELIGILN NLGYSKDQVF   300
KF                                                                  302

SEQ ID NO: 36          moltype = AA  length = 222
FEATURE                Location/Qualifiers
source                 1..222
                       mol_type = protein
                       organism = Saccharomyces cerevisiae
SEQUENCE: 36
MTELDYQGTA EAASTSYSRN QTDLKPFPSA GSASSSIKTT EPVKDHRRRR SSSIISHVEP    60
ETFEDENDQQ LLPNMNATWV DQRGAWIIHV VIIILLKLFY NLFPGVTTEW SWTLTNMTYV   120
IGSYVMFHLI KGTPFDFNGG AYDNLTMWEQ IDDETLYTPS RKFLISVPIA LFLVSTHYAH   180
YDLKLFSWNC FLTTFGAVVP KLPVTHRLRI SIPGITGRAQ IS                      222

SEQ ID NO: 37          moltype = AA  length = 111
FEATURE                Location/Qualifiers
source                 1..111
                       mol_type = protein
                       organism = Saccharomyces cerevisiae
SEQUENCE: 37
MSTVTKYFYK GENTDLIVFA ASEELVDEYL KNPSIGKLSE VVELFEVFTP QDGRGAEGEL    60
GAASKAQVEN EFGKGKKIEE VIDLILRNGK PNSTTSSLKT KGGNAGTKAY N            111
```

```
SEQ ID NO: 38          moltype = AA  length = 259
FEATURE                Location/Qualifiers
source                 1..259
                       mol_type = protein
                       organism = Saccharomyces cerevisiae
SEQUENCE: 38
MEPESIGDVG NHAQDDSASI VSGPRRRSTS KTSSAKNIRN SSNISPASMI FRNLLILEDD   60
LRRQAHEQKI LKWQFTLFLA SMAGVGAFTF YELYFTSDYV KGLHRVILQF TLSFISITVV  120
LFHISGQYRR TIVIPRRFFT STNKGIRQFN VKLVKVQSTW DEKYTDSVRF VSRTIAYCNI  180
YCLKKFLWLK DDNAIVKFWK SVTIQSQPRI GAVDVKLVLN PRAFSAEIRE GWEIYRDEFW  240
AREGARRRKQ AHELRPKSE                                               259

SEQ ID NO: 39          moltype = AA  length = 548
FEATURE                Location/Qualifiers
source                 1..548
                       mol_type = protein
                       organism = Saccharomyces cerevisiae
SEQUENCE: 39
MYFPFLGRLS ITDYIIVVLV YIESIISSVL KLIPQPMINL FEWLINFSTS SDDNTIEEKL   60
RSAPTIHEMC AIFDISVEDH LVRTEDNYIL TLHRIPPISK NRFNNKVVYL HHGLLMCSDV  120
WCCNIERHKN LPFVLHDLGY DVWMGNNRGN KYSTAHLNKP PKSNKFWDFS IDEFAFFDIP  180
NSIEFILDIT KVDKVICIGF SQGSAQMFAA FSLSEKLNRK VSHFIAIAPA MTPKGLHNRI  240
VDTLAKSSPG FMYLFFGRKI VLPSAVIWQR TLHPTLFNLC IDIANKILFN WKSFNILPRQ  300
KIASYAKLYS TTSVKSIVHW FQILRSQKFQ MFEESDNMLN SLTRPYQIAN FPTRTNIKIP  360
ILLIYGGIDS LVDIDVMKKN LPFNSVFDVK VDNYEHLDLI WGKDADTLVI AKVLRFIEFF  420
NPGNVSVKTN QLLPSASLVE ELPSTTWKTT HPTHGLSYRT HSADRSPLSV QADEADEVHN  480
ADNSRFLRRV FSTSAIDEDN ENEHQDDTED QIHKEQQRRL SAYLESSKDL RQLDANSSTT  540
ALDALNKE                                                           548

SEQ ID NO: 40          moltype = AA  length = 274
FEATURE                Location/Qualifiers
source                 1..274
                       mol_type = protein
                       organism = Saccharomyces cerevisiae
SEQUENCE: 40
MIRQLNYWSR KAYLIYPFQV FVGALLSIVV SSETLNHQKE TCALLKSSNI FNVIFAYKAN   60
QLWPFLFFSL AFLQIYFHYL ARMDILPLPI SSTETSSSYL TYTNHWPLLK NRIISIMITQ  120
YACKFVLKYL LLFLNFQFID HVFIWTGGEC SSGSKTTSAE KCRLENGKWD GGFDISGHFC  180
FLVSISMILW MELHLFSRFV QAEDMFWVVN KWVRACLAIV CAVLVIWICI LWVTAIYYHT  240
ILEKVLGCLM GFICPVFIYH ILPKIGILHN YLYL                              274
```